US011369764B2

(12) United States Patent
Bornholdt et al.

(10) Patent No.: US 11,369,764 B2
(45) Date of Patent: Jun. 28, 2022

(54) OVERMOLDED TEXTILE CUSHION

(71) Applicant: Fisher & Paykel Healthcare Limited, Auckland (NZ)

(72) Inventors: Melissa Catherine Bornholdt, Auckland (NZ); Bruce Michael Walls, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 325 days.

(21) Appl. No.: 16/490,306

(22) PCT Filed: Mar. 2, 2018

(86) PCT No.: PCT/NZ2018/050023
§ 371 (c)(1),
(2) Date: Aug. 30, 2019

(87) PCT Pub. No.: WO2018/160077
PCT Pub. Date: Sep. 7, 2018

(65) Prior Publication Data
US 2020/0016358 A1  Jan. 16, 2020

Related U.S. Application Data

(60) Provisional application No. 62/466,608, filed on Mar. 3, 2017.

(51) Int. Cl.
*A61M 16/06* (2006.01)
(52) U.S. Cl.
CPC ..... *A61M 16/0622* (2014.02); *A61M 16/0683* (2013.01); *A61M 2207/10* (2013.01)

(58) Field of Classification Search
CPC .............. A61M 16/06; A61M 16/0605; A61M 16/0611; A61M 16/0616; A61M 16/0622; A62B 18/02; A62B 18/025
See application file for complete search history.

(56) References Cited

U.S. PATENT DOCUMENTS 9,981,104 B1 * 5/2018 Groll ................... A61M 16/125
2008/0047560 A1 2/2008 Mertens
(Continued)

FOREIGN PATENT DOCUMENTS

WO  WO 2009/026627  3/2009
WO  WO 2016/082001  6/2016

OTHER PUBLICATIONS

Patent Cooperation Treaty, International Search Report and Written Opinion, Application No. PCT/NZ2018/050023, dated Jun. 22, 2018, in 20 pages.

*Primary Examiner* — Joseph D. Boecker
(74) *Attorney, Agent, or Firm* — Knobbe Martens Olson and Bear, LLP

(57) ABSTRACT

A cushion for a respiratory mask is provided. The cushion includes a face contacting portion, a non-face contacting portion and an intermediate region. The face contacting portion is formed from an open cell foam material and includes an opening to provide, in use, a source of breathing gas to a user's airways. The non-face contacting portion is formed from an elastomeric material. The intermediate region is formed between the face contacting portion and the non-face contacting portion. Open cells of the open cell foam material in the intermediate region are filled with the elastomeric material.

17 Claims, 63 Drawing Sheets

(56) References Cited

U.S. PATENT DOCUMENTS

| | | | | |
|---|---|---|---|---|
| 2008/0142015 | A1* | 6/2008 | Groll | A61M 16/125 |
| | | | | 128/206.24 |
| 2012/0204881 | A1* | 8/2012 | Davidson | A61M 16/0683 |
| | | | | 128/206.25 |
| 2012/0285469 | A1* | 11/2012 | Ho | A61M 16/0057 |
| | | | | 128/206.24 |
| 2014/0158136 | A1* | 6/2014 | Romagnoli | A61M 16/0666 |
| | | | | 128/206.24 |
| 2015/0352307 | A1* | 12/2015 | Rutan | A61M 16/0622 |
| | | | | 128/206.24 |
| 2015/0374945 | A1* | 12/2015 | Anthony | B29C 51/00 |
| | | | | 604/179 |
| 2016/0001029 | A1* | 1/2016 | Bayer | A61M 16/0611 |
| | | | | 128/206.24 |
| 2017/0049983 | A1* | 2/2017 | Ellis | B32B 25/10 |
| 2017/0281889 | A1* | 10/2017 | Voncken | A61M 16/0622 |
| 2017/0326320 | A1* | 11/2017 | Baigent | A61M 16/0616 |
| 2019/0070379 | A1* | 3/2019 | Lockhart | A61M 16/0616 |
| 2021/0220597 | A1* | 7/2021 | Steed | A61M 16/0622 |
| 2021/0260324 | A1* | 8/2021 | Hammer | A61M 16/0622 |

* cited by examiner

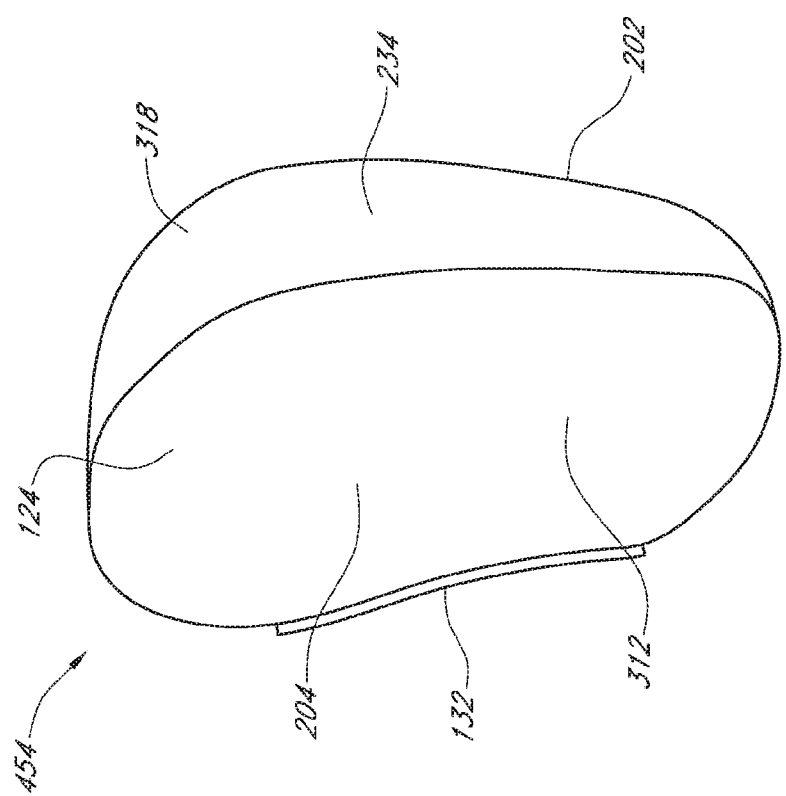

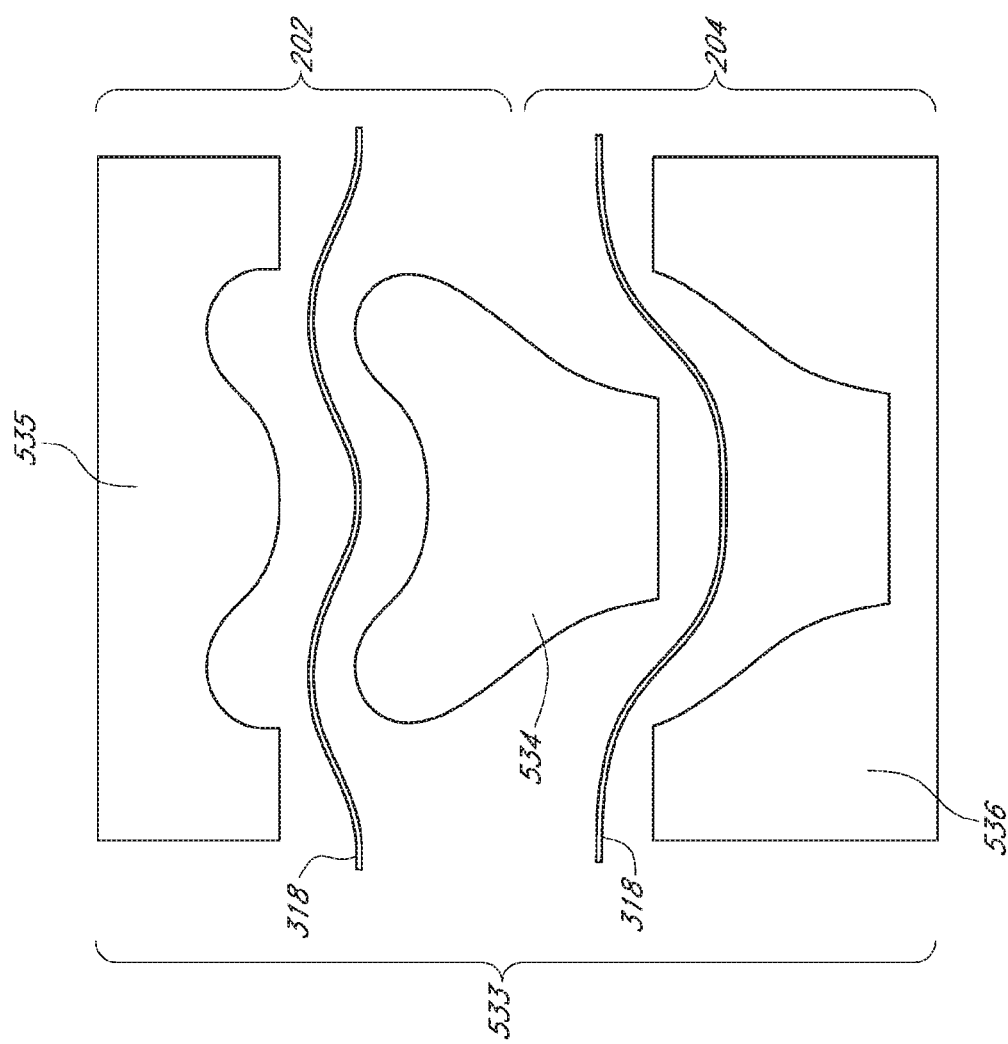

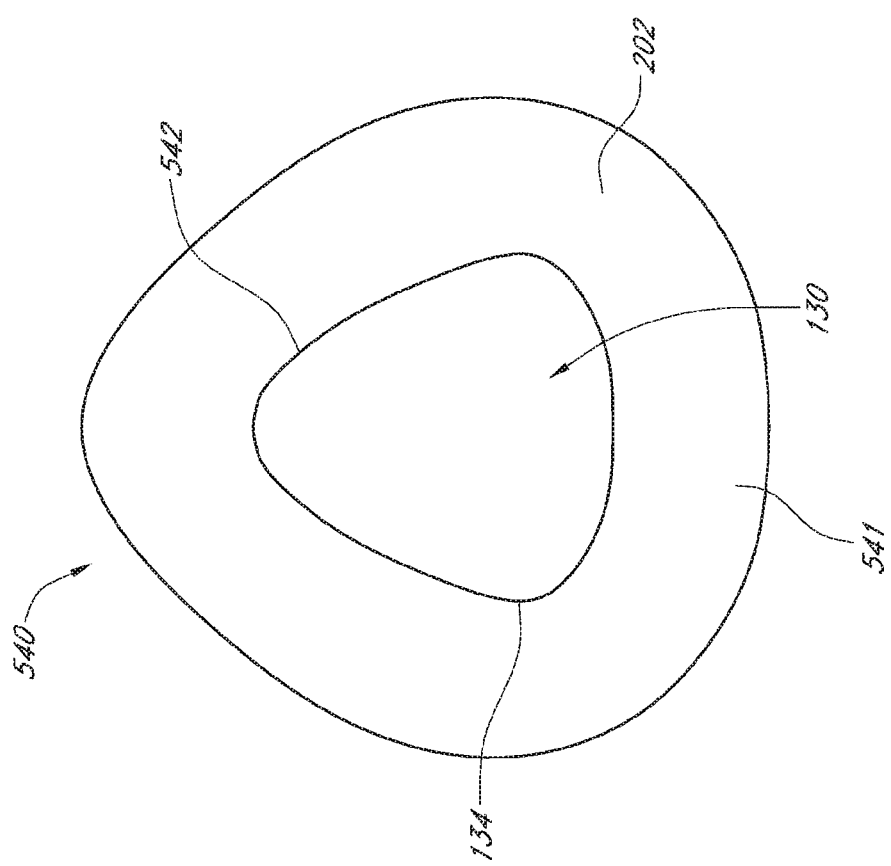

OVERMOLDED TEXTILE CUSHION

FIELD OF INVENTION

The disclosure generally relates to a seal for a respiratory interface, and to an interface including the seal, comprising either a mask or a mask and headgear. More particularly, certain aspects of the present disclosure relate to a cushion having a textile portion and an elastomeric portion.

BACKGROUND

Respiratory interfaces are used to provide respiratory gas or gases, such as air in CPAP (or other positive pressure) therapy, to a user under positive pressure. A respiratory interface delivers the gases to the nose and mouth of a user. The respiratory interface provides a substantially airtight seal against the user's face such that pressurized gases are received by the user through the respiratory interface.

SUMMARY OF THE INVENTION

Preferably, the respiratory interface is constructed to be soft, comfortable and lightweight when donned by the user and having an aesthetic that fits in the bedroom. The respiratory interface may be formed from a plurality of materials such that certain portions of the respiratory interface provide sufficient rigidity to inhibit collapsing due to over-tightening of the respiratory interface during fitting. Other portions may provide a soft touch and appearance that has an aesthetic that fits in the bedroom.

The systems, methods and devices described herein have innovative aspects, no single one of which is indispensable or solely responsible for their desirable attributes. Without limiting the scope of the claims, some of the advantageous features will now be summarized.

In accordance with at least one of the embodiments disclosed herein, a cushion for a respiratory mask is provided. The cushion comprises an open cell foam material, the face contacting portion including an opening to provide, in use, a source of breathing gas to a user's airways; a non-face contacting portion comprising an elastomeric material; and an intermediate region formed between the face contacting portion and the non-face contacting portion. The elastomeric material of the non-face contacting portion is received in open cells of the open cell foam material in the intermediate region.

According to a further aspect, the intermediate region extends at least partially around a periphery of the cushion.

According to a further aspect, the intermediate region extends around a periphery of the cushion.

According to a further aspect, the intermediate region extends entirely around a periphery of the cushion.

According to a further aspect, the face contacting portion comprises a mouth region and a nasal region.

According to a further aspect, the nasal region is comprised of open cell foam material.

According to a further aspect, the nasal region is comprised of a textile material.

According to a further aspect, the mouth region comprises the same material as the non-face contacting portion.

According to a further aspect, the intermediate region extends from the periphery to the opening along the face contacting portion.

According to a further aspect, the face contacting portion comprises a laminate material.

According to a further aspect, the open cell foam material forms part of a foam and fabric laminate material.

In accordance with at least one of the embodiments disclosed herein, a cushion for a respiratory mask is provided. The cushion comprises a face contacting portion comprising a locating region for locating a user's face relative to the mask and a sealing region for providing a seal against a user's face; and a non-face contacting portion. The sealing region surrounds the locating region, and the locating region comprises a textile material.

According to a further aspect, the sealing region comprises an elastomeric material.

According to a further aspect, the non-face contacting portion and the sealing region comprise the same material.

According to a further aspect, the non-face contacting material comprises a silicone material.

According to a further aspect, the sealing region comprises a transition region that extends between the sealing region and the locating region.

According to a further aspect, the transition region comprises a composite material.

According to a further aspect, the transition region comprises the textile material that is impregnated with the elastomeric material of the sealing region.

According to a further aspect, in use, the transition region and sealing region are configured to form a seal against a user's face.

According to a further aspect, the locating region comprises a continuous surface that is breathable such that, in use, a supply of breathing gas can be provided to a user's airways through the locating region.

According to a further aspect, the locating region comprises a first opening configured, in use, to supply a breathing gas to at least a patient's nose.

According to a further aspect, the first opening is a nasal opening configured to deliver a supply of breathing gas to a patient's nose.

According to a further aspect, the first opening is an oro-nasal opening configured to deliver a supply of breathing gas to a patient's mouth and nose.

According to a further aspect, the locating region further comprises an oral opening located, in use, below the nasal opening.

According to a further aspect, the textile material of the locating region comprises more than one layer.

According to a further aspect, the transition region has a greater thickness than the locating region.

According to a further aspect, the transition region protrudes in a thickness direction towards an interior of the cushion.

According to a further aspect, the transition region protrudes from an inner surface of the face contacting portions, and wherein an outer surface of the face contacting portion is a smooth continuous surface.

In accordance with at least one of the embodiments disclosed herein, a cushion for a respiratory mask is provided. The cushion comprises a face contacting portion including a locating region for locating a user's face relative to the mask and a sealing region for providing a seal against a user's face; and a non-face contacting portion comprising an elastomeric material. The locating region is formed from a textile material and the textile material is configured to have a predetermined three-dimensional contoured shape. The sealing region is positioned around the locating region such that the sealing region surrounds the locating region and at least partially defines the predetermined three-dimensional contoured shape of the textile material.

According to a further aspect, the textile material is supported under tension by the sealing region to form the predetermined three-dimensional contoured shape of the textile material.

According to a further aspect, the textile material is stretchable in a single axis.

According to a further aspect, the textile material is stretchable in multiple axes.

According to a further aspect, the textile material is stretchable in two axes.

According to a further aspect, the sealing region comprises a composite material.

According to a further aspect, the composite material comprises an outer perimeter of the stretchable textile material of the locating region that is over-molded with the same elastomeric material as the non-face contacting portion, such that the textile is impregnated with the elastomeric material.

According to a further aspect, the cushion further comprises a stabilizing layer, wherein the stabilizing layer comprises a layer of elastomeric material that supports at least a portion of the locating region.

According to a further aspect, the stabilizing layer is located in an upper half of the face contacting portion and is configured, in use, to apply a force to a patient's nose to stabilize the cushion on the patient's face.

According to a further aspect, the stabilizing layer extends across a nasal bridge portion of the face contacting portion.

According to a further aspect, the stabilizing layer is separated from the textile layer.

According to a further aspect, the stabilizing layer is positioned in a nasal bridge portion.

According to a further aspect, the stabilizing layer has an outer edge that is attached to an inner perimeter of the sealing region, and an inner edge that is free.

According to a further aspect, the stabilizing layer comprises a pair of stabilizing layers, each positioned on respective sides of the user's nose, in use.

According to a further aspect, the sealing region comprises a composite material and extends into the non-face contacting portion.

In accordance with at least one of the embodiments disclosed herein, a cushion for a respiratory mask is provided. The cushion comprises a face contacting portion; and a non-face contacting portion. At least part of the face contacting portion comprises a permeable material and the non-face contacting portion comprises an elastomeric material. The permeable material part of the face contacting portion is joined to the non-face contacting portion by permeation of elastomeric material into at least part of the permeable material.

According to a further aspect, at least part of the face contacting portion comprises an elastomeric material and the permeable material part of the face contacting portion is joined to the non-face contacting portion by permeation of the elastomeric material of the face contacting portion into the permeable material.

According to a further aspect, an elastomeric material part of the face contacting portion is unitary with the non-face contacting portion.

According to a further aspect, the face contacting portion comprises a locating region and a sealing region, the sealing region surrounding the locating region, and wherein the locating region incorporates the permeable material part of the face contacting portion.

According to a further aspect, the face contacting portion comprises a locating region and a sealing region, the sealing region surrounding the locating region, and wherein the sealing region incorporates the elastomeric material part of the face contacting portion.

According to a further aspect, an entirety of the face contacting portion comprises a permeable material and the face contacting portion is joined to the non-face contacting portion by permeation of elastomeric material of the non-face contacting portion into the permeable material of the face contacting portion.

In accordance with at least one of the embodiments disclosed herein, a cushion for a respiratory mask is provided. The cushion comprises an elastomeric sealing structure having a face contacting portion and a non-face contacting portion; and a textile layer. The textile layer is permanently secured to an outer surface of the non-face contacting portion of the elastomeric sealing structure.

According to a further aspect, the face contacting portion comprises an elastomeric material.

According to a further aspect, the textile layer comprises a non-stretch textile.

According to a further aspect, the textile layer further comprises a split configured to allow the textile layer to conform to the outer surface of the non-face contacting portion of the cushion.

According to a further aspect, the face contacting portion further comprises a locating region for locating a user's face relative to the mask and a sealing region for providing a seal against a user's face.

According to a further aspect, the locating region comprises a continuous surface that is breathable such that, in use, a supply of breathing gas can be provided to a user's airways through the locating region.

According to a further aspect, the textile layer extends from a locating region of the face contacting portion to a periphery of the non-face contacting portion that is a spaced distance from an opening defining an inlet to a breathing chamber of the cushion.

According to a further aspect, the textile layer extends from a locating region of the face contacting portion to an exposed periphery that extends outwardly past an inlet of the non-face contacting portion of the cushion.

According to a further aspect, the locating region comprises a three-dimensional knitted textile material.

According to a further aspect, the three-dimensional knitted textile material of the locating region comprises more than one layer.

In accordance with at least one of the embodiments disclosed herein, a cushion for a respiratory mask is provided. The cushion comprises a flexible sealing structure having at least one wall configured to seal against the face of a user; and a textile layer. The textile layer is encased within the at least one wall of the flexible sealing structure.

According to a further aspect, the textile layer is visible from the outside of the cushion through an elastomeric material that comprises the flexible sealing structure.

According to a further aspect, the flexible sealing structure further comprises a second wall such that the at least one wall and the second wall define a breathing chamber.

According to a further aspect, the textile layer extends continuously from the at least one wall to the second wall, and wherein the textile layer is encased within the second wall of the flexible sealing structure.

According to a further aspect, the at least one wall further comprises a locating region for locating a user's face relative to the mask and a sealing region for providing a seal against a user's face.

According to a further aspect, the locating region comprises a continuous surface that is breathable such that, in use, a supply of breathing gas can be provided to at least one of a user's airways through the locating region.

According to a further aspect, the locating region comprises a three-dimensional knitted textile material.

According to a further aspect, the three-dimensional knitted textile material of the locating region comprises more than one layer.

In accordance with at least one of the embodiments disclosed herein, a cushion for a respiratory mask is provided. The cushion comprises a flexible sealing structure having a face contacting portion configured to seal against a user's face and a non-face contacting portion, the sealing structure comprising an elastomeric layer, a first textile layer, and a second textile layer. The first textile layer forms at least part of the face contacting portion, the second textile layer forms at least part of the non-face contacting portion, and the elastomeric layer forms at least an internal portion of the face contacting portion and the non-face contacting portion.

According to a further aspect, the first textile layer and the second textile layer are formed of a stretchable textile material.

According to a further aspect, the stretchable textile material comprises a laminate of one or more textile sheet layers.

According to a further aspect, at least one of the first textile layer and the second textile layer is formed of a three-dimensional knitted textile material.

According to a further aspect, the face contacting portion comprises an oro-nasal opening configured to receive a nose and a mouth of a user.

According to a further aspect, the face contacting portion comprises a breathable locating region.

According to a further aspect, the first textile layer is formed of a first stretchable textile material and the second textile layer is formed of a second stretchable textile material that is distinct from the first stretchable textile material.

According to a further aspect, the elastomeric layer joins the first textile layer and the second textile layer at a seam.

According to a further aspect, the cushion further comprises a bonding material interposed between an inner side of the first textile layer and an inner side of the second textile layer, wherein the bonding material joins the face contacting portion and the non-face contacting portion to define a breathing chamber of the cushion.

According to a further aspect, the face contacting portion and the non-face contacting portion define a flush outer surface of the non-face contacting portion of the cushion.

According to a further aspect, the bonding material is an elastomeric material.

In accordance with at least one of the embodiments disclosed herein, a cushion for a respiratory mask is provided. The cushion comprises a flexible sealing structure having a first portion configured to be disposed toward a user's face and a second portion configured to be disposed away from the user's face; and a textile cover configured to be selectively positioned in a covering state in which the textile cover covers at least part of the first portion or an uncovering state in which the textile cover does not cover the first portion. The textile cover is permanently secured to the cushion.

According to a further aspect, the first portion defines a face contacting portion and the second portion defines a non-face contacting portion of the cushion.

According to a further aspect, the textile cover further comprises a first end secured to the cushion and a free end opposite the first end.

According to a further aspect, the first end of the textile cover is permanently secured to an outer surface of the second portion of the cushion.

According to a further aspect, the first end of the textile cover is removably secured to an outer surface of the second portion of the cushion.

According to a further aspect, the first portion and the second portion of the cushion define a breathing chamber.

According to a further aspect, the textile cover is secured to at least a portion of the breathing chamber of the cushion.

According to a further aspect, the textile cover further comprises a height that is less than a height and a width of the cushion.

According to a further aspect, the first portion of the cushion further comprises a sealing region configured to engage the user's face, and the textile cover further comprises a length sufficient to allow the free end to at least partially cover the sealing region when in the covering state.

According to a further aspect, the cushion further comprises an oro-nasal opening on the first portion of the cushion, wherein the free end of the textile cover is configured to secure against the oro-nasal opening when in the covering state.

According to a further aspect, the textile cover is formed of a stretchable textile material.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

FIG. 10D is a side view of the cushion of FIG. 10A.

FIG. 16A is a cross-sectional view of a forming tool during a step in the forming process of the cushion of FIGS. 16B and 16C.

FIG. 18C is a rear view of the cushion of FIG. 18A with the textile cover in a covered state.

DETAILED DESCRIPTION

Figure 1:
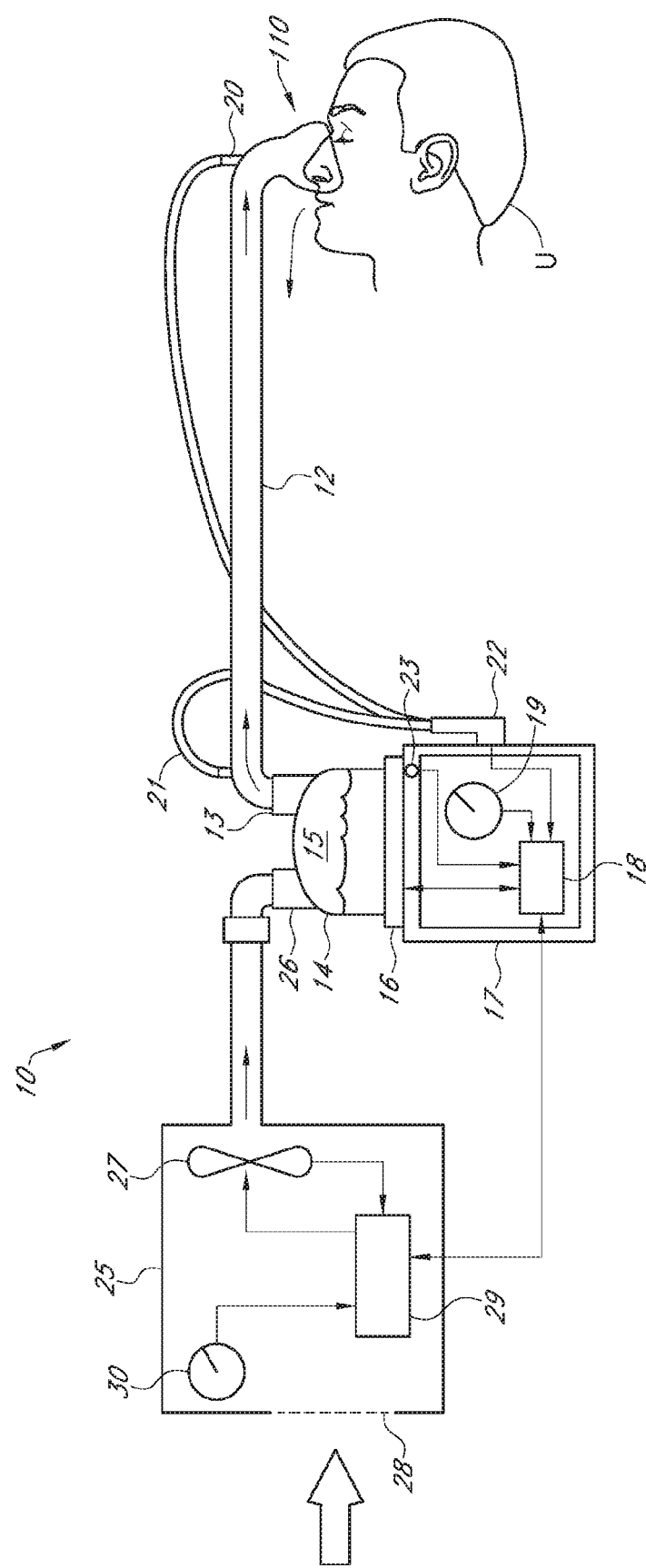
FIG. 1 is a view of a respiratory system comprising a flow generator, a humidifier and a user interface.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The example embodiments and/or individual features of different embodiments may be combined, other embodiments may be utilized or structural changes may be made, without departing from the scope of the claimed subject matter. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. As used herein the terms 'front', 'rear', 'upper' and 'lower' shall refer to the location of a part or portion of a respiratory mask in relation to a user. Wherein, 'front' refers to a location that is distal to the user (when the mask is in use) and 'rear' refers to a location that is proximal to the user by comparison. The terms 'upper' and 'lower' refer to the location of a part or component of a mask relative to the rest of the mask when the mask is in use and the user is sitting in an upright position. Moreover, terms such as "first," "second," "third," and so on may be used to describe separate components. Such terminology may include the words specifically mentioned above, derivatives thereof, and words of similar import.

FIG. 1 is a schematic diagram of a positive pressure respiratory therapy system in the form of a continuous positive airway pressure (CPAP) system 10 for providing a heated and humidified air stream to a user U through an interface 110 worn by the user, and which is connected to CPAP system 10 by a conduit or tube 12. A humidification chamber 14 has a heat conductive base in contact with a heater plate 16 of a humidifier 17 to humidify the air stream. The conduit 12 is connected to an outlet 13 of the humidification chamber 14 to convey humidified air to the user interface 110. The humidifier 17 comprises a controller 18, such as a microprocessor-based controller that executes computer software commands stored in an associated memory, for example but without limitation. The controller 18 receives input commands from multiple sources, including a user input interface 19 such as a dial or touch screen, which enables the setting of a predetermined value of humidity, temperature, or other characteristic of the humidified air supplied to the user U. The controller 18 also may receive input from one or more other sources, such as for example temperature and/or flow velocity sensors 20 and 21, which are connected through a connector 22 to communicate with the controller 18, and/or a heater plate temperature sensor 23. In response to the selected humidity or temperature value, the controller 19 determines when and/or to what level the heater plate 16 should be energized to suitably heat the water contained in the humidification chamber 14.

As the volume of water in the chamber is heated, water vapor begins to fill the volume of the chamber above a surface of the water. The water vapor passes out of the outlet 13 of the humidification chamber with a flow of air that is provided from a supply 25, such as a blower 27, and which enters the humidification chamber 30 through an inlet 26. The blower 27 can be a variable speed fan, or can include a variable pressure regulator. The blower 27 draws air through an inlet 28. The blower can be controlled by a controller 29 or by the controller 18, for example. The controller 18 or 29 may control blower speed, regulated pressure, or the like according to any suitable criteria. For example, the controller 29 may respond to inputs from controller 18 and a user set value (e.g., a preset value) of pressure and/or fan speed, which can be set with a user interface 30 (e.g., a dial).

The seal and interfaces of the disclosure can be used in such a CPAP system as described whether humidified or not, or alternatively in other forms of respiratory systems, such as for example VPAP (Variable Positive Airway Pressure) systems, BiPAP (Bi level Positive Airway Pressure) systems, or with a ventilator, and are described herein generally with reference to CPAP therapy by way of example only.

Figure 2A:
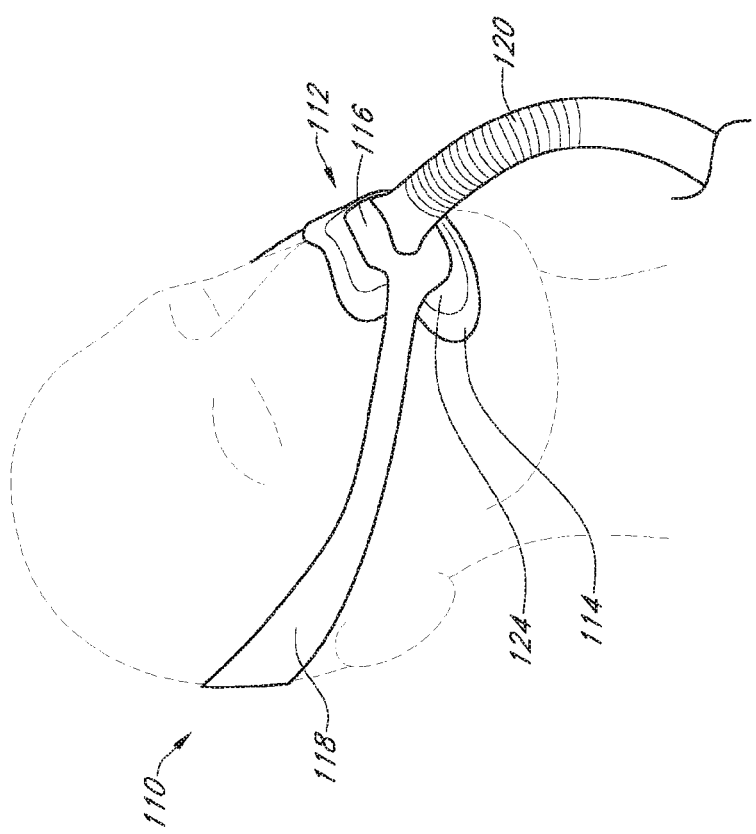
FIG. 2A is a perspective view of a user interface, comprising a mask and a headgear, which is suitable for use with the respiratory system of FIG. 1.
Figure 2B:
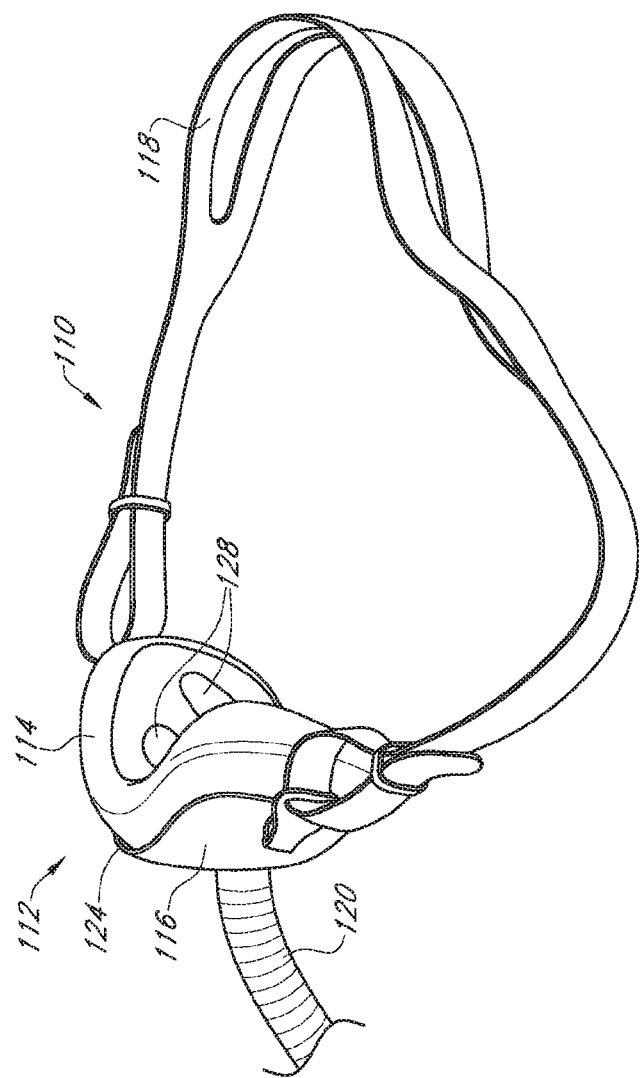
FIG. 2B is a side view of the user interface of FIG. 1.
Figure 3A:
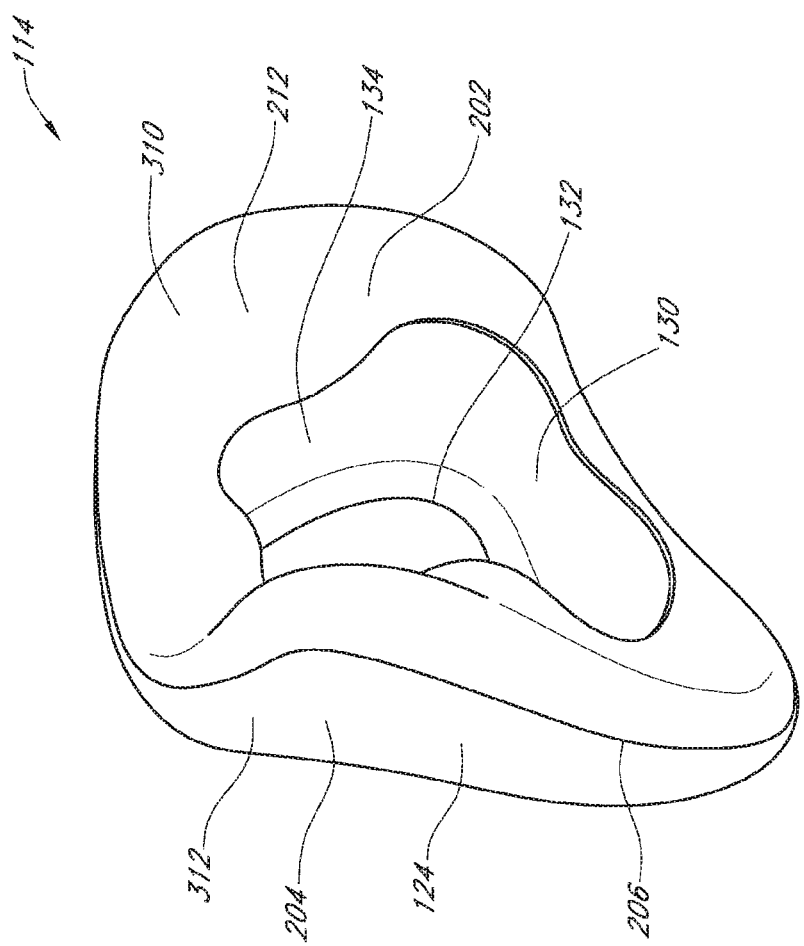
FIG. 3A is a perspective view of an exemplary cushion for use with the respiratory system of FIG. 1.
Figure 3B:
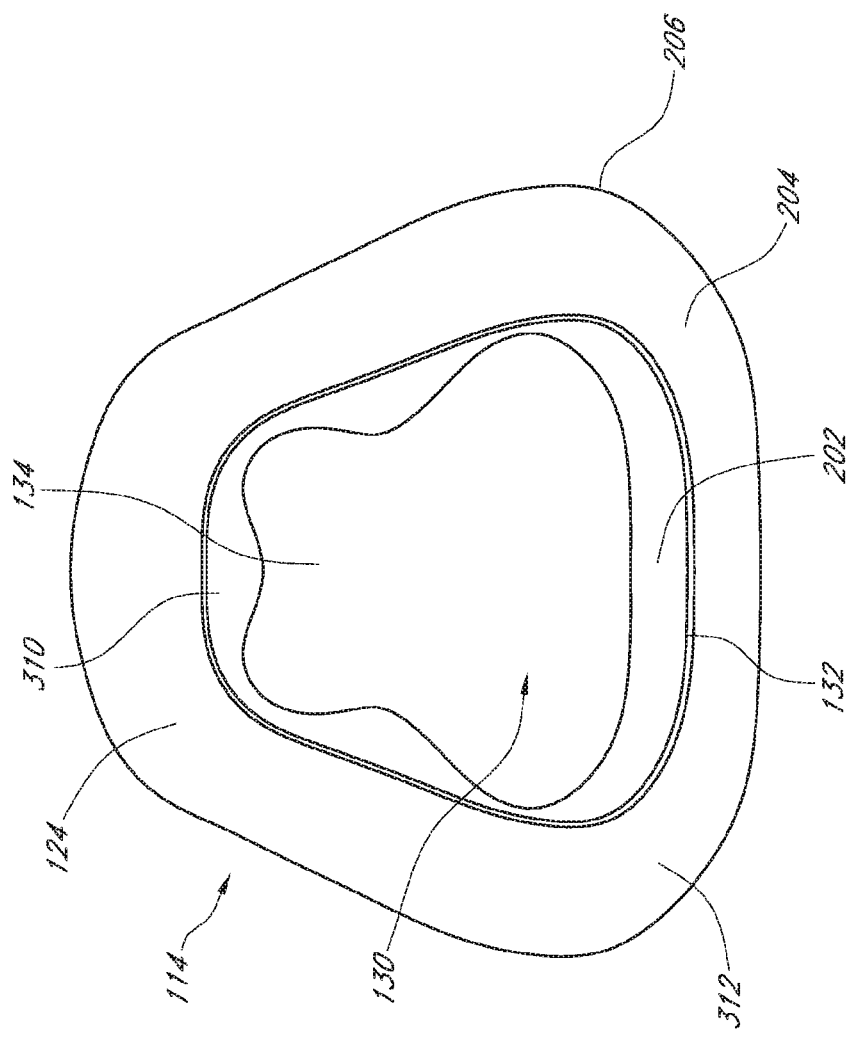
FIG. 3B is a front view of the cushion of FIG. 3A.
Figure 3C:
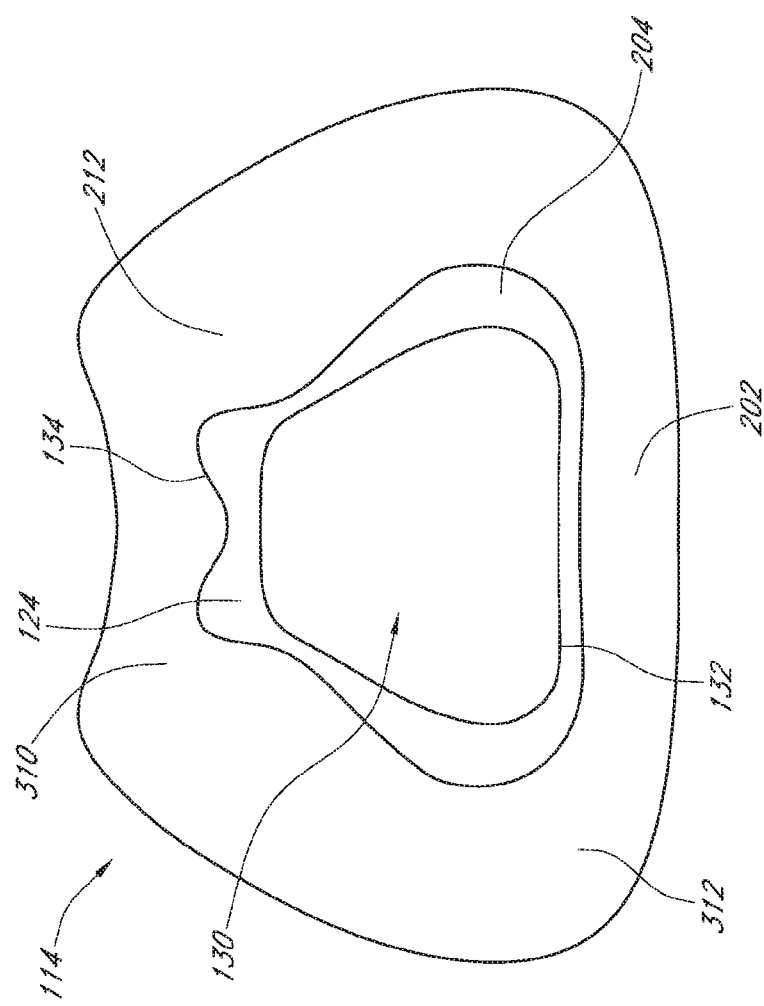
FIG. 3C is a rear view of the cushion of FIG. 3A.
Figure 3D:
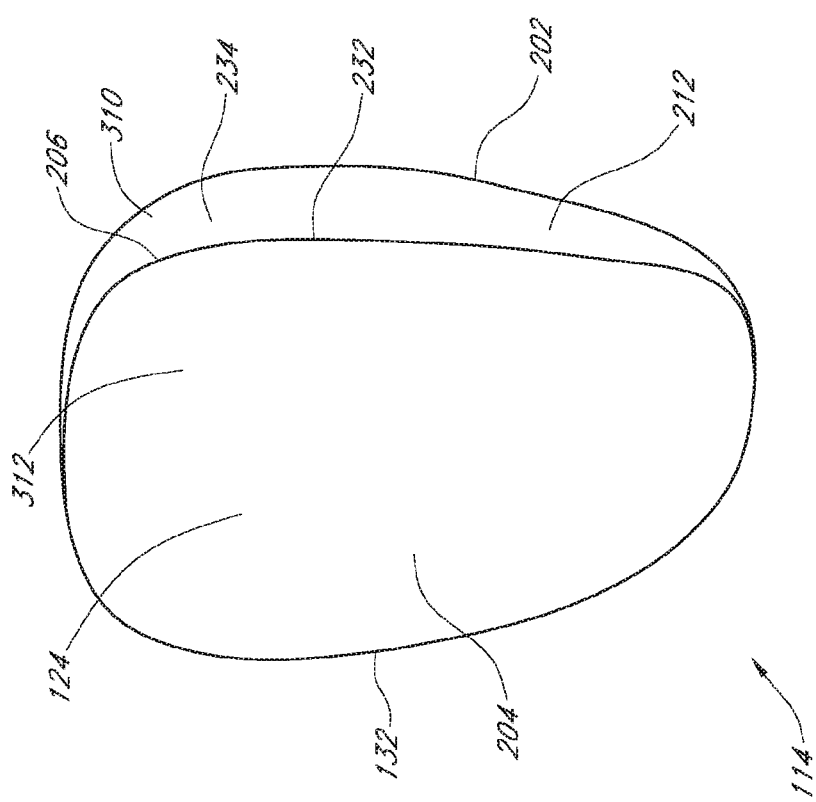
FIG. 3D is a side view of the cushion of FIG. 3A.
Figure 3E:
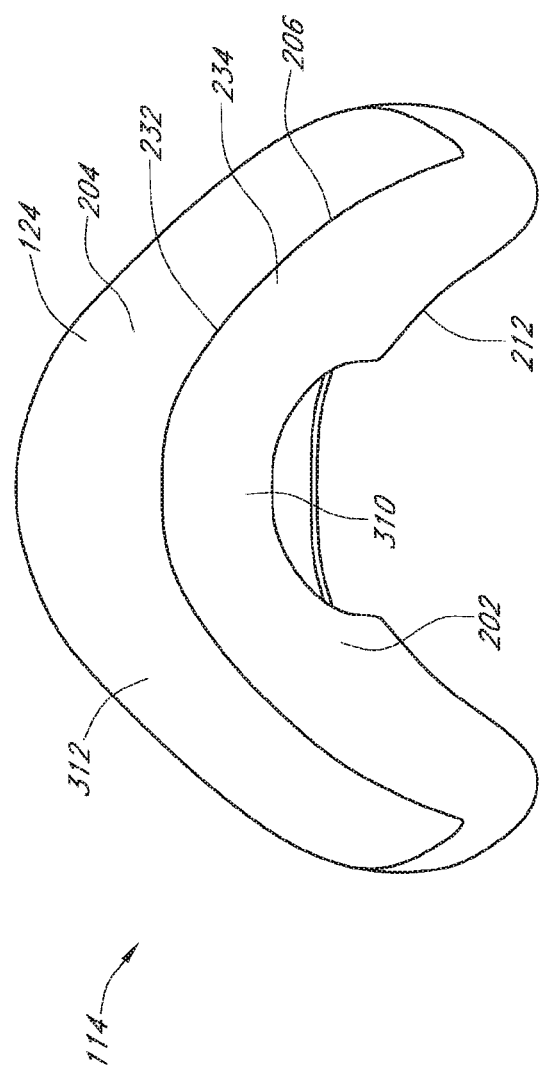
FIG. 3E is a top view of the cushion of FIG. 3A.
Figure 3F:
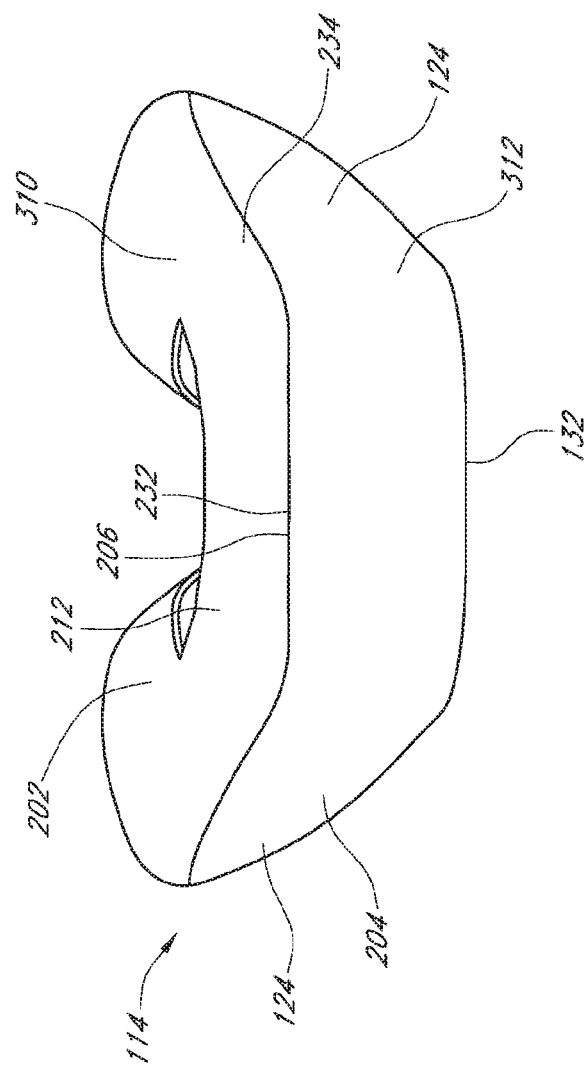
FIG. 3F is a bottom view of the cushion of FIG. 3A.

FIGS. 2A and 2B illustrate examples of the interface assembly or interface 110 of the system 10 of FIG. 1. The interface 110 comprises a full-face mask 112, which in some configurations includes a cushion 114 and a frame assembly or frame 116. The interface 110 also includes a headgear 118 for securing the mask 112 to the user. The full-face mask 112 is configured to seal around a user's mouth and on the lower surfaces of the user's nose. The features of the cushion embodiments, as described herein, can be applied to any mask configuration including and are not limited to full-face and nasal masks or direct nasal masks. Thus, the description of features specific to full-face masks is merely by way of example and such descriptions can be replaced with the suitable description of another mask or interface type. For example, references to an oro-nasal opening can be replaced with a reference to a nasal opening or nasal openings.

In some configurations, the interface 110 also comprises a short flexible supply conduit or tube 120 that extends from the mask 112, such as from a central connection at the front of the mask 112, which connects to the supply conduit 12 of the CPAP system 10 or other respiratory system. The conduit 120 is connected to the mask 112 either directly or via a suitable connector, such as a hollow elbow. In some configurations, the conduit 120 can swivel about one or more swivel axes relative to the mask 112 so that the path of the conduit 120 relative to the positioning of the mask 112 on the face of the user can adapt to the sleeping position of the user. The end of the conduit 120 opposite the 122 can comprise a suitable connector for connecting the conduit 120 to the supply conduit 12. In some configurations, the connector can be or comprise a swivel connector that allows relative rotation between the conduit 120 and the supply conduit 12.

As described above, the mask 112 can comprise a cushion 114 and a frame 116. In some configurations, the cushion 114 has a housing 124 that is coupled to the frame 116 such that the cushion 114 and the frame 116 together form an enclosure or breathing chamber having a gas flow inlet from the CPAP system 10 and an aperture(s) 128 through the cushion 114 to the user. In some configurations, the frame 116 can be stiffer than at least a portion of the cushion 114.

Foam and Silicone Impregnated Join

FIGS. 3A to 3F illustrate an exemplary configuration of the cushion 114 of the mask 112 for use with the CPAP system 10 of FIG. 1. As illustrated, the cushion 114 comprises a user face contacting portion 202 and a non-face contacting portion 204. The non-face contacting portion 204 forms a forward facing or relatively distal portion of the partially enclosed breathing chamber 130. The face contacting portion 204 forms a rearward facing or relatively proximal portion of the breathing chamber 130 and is configured to engage with and form a substantially airtight seal against a user's face. The face contacting portion 202 and the non-face contacting portion 204 are connected along their respective edges by an intermediate region 206.

The face contacting portion 202 contacts the face of the user to provide a seal that substantially encloses the nose and mouth of the user. That is, the face contacting portion 202 is configured to engage and form a substantially airtight seal with a user's face. The face contacting portion 202 has an oro-nasal opening 134 which receives the nose and mouth of the user. Pressurized gases supplied by the conduit 120 enters the breathing chamber 130 and are received by the user through the oro-nasal opening 134.

The face contacting portion 202 is formed from an open cell foam material. Preferably, the face contacting portion 202 is formed from an open cell foam material 310 such that the portion of the cushion 114 that contacts the user's face is soft in touch and appearance. That is, the open cell foam material 310 provides a soft touch that is comfortable against a user's face, and an appearance that is comforting and desirable in a bedroom environment. The open cell foam material 310 also provides structure and stability to the face contacting portion 202 whilst being conformable to adapt to differing facial geometries. The open cell foam material 310 provides a lightweight face contacting portion 202 that reduces the overall weight of the cushion 114. A lighter cushion requires lower headgear retention forces than a heavier cushion, which can improve user comfort. The open cell foam material 310 may also be breathable to enable the user's skin to breathe which improves the comfort of the cushion 114. In some embodiments, the open cell foam material 310 may be airtight or at least have some airtight regions. In other embodiments, the open cell foam material 310 can form a leak diffuser that diffuses the flow of gas leaks to prevent or inhibit jetting which makes the leak less noticeable and disruptive to a user.

In some configurations, the face contacting portion 202 may be formed from a thermoformed material, which contains an open cell foam material 310 such as Breath-o-prene®. The face contacting portion 202 may be thermoformed to have a three-dimensional geometry that is contoured to engage with and conform to the user's face. Preferably, the face contacting portion 202 has a relatively thin wall structure (i.e., thickness less than 5 mm). In some configurations, the face contacting portion 202 may have a thickness that is constant or variable along its length, width and depth.

The open cell foam material 310 of the face contacting portion 202 may have an outer surface 212 that contacts a user's face. The open cell foam material 310 is lightweight and provides a texture that is soft to the touch and in aesthetic appearance. The open cell foam in some embodiments has a textile covering that provides the outer surface 212. In some embodiments, the open cell foam material may be in the form of a laminate containing one or more textile sheet layers. In these embodiments, the textile may be brushed, flocked, or have a pile/napping or texture that can engage with facial hair on a user's face. That is, the outer surface 212 may comprise a textile that is flocked. For example, Breath-o-prene® is a textile and foam laminate material with textile outer layers In some configurations, the non-face contacting portion 204 defines the housing 124 of the cushion 114. The non-face contacting portion 204 has a frame connection opening 132 that engages the frame 116 (see FIGS. 2A and 2B). The frame connection opening 132 provides an inlet through which a supply of pressurized air enters the breathing chamber 130. In the illustrated arrangement, the non-face contacting portion 204 is formed from a resilient thermoplastic elastomeric material such as silicone rubber 312 to provide a support structure and to define the airtight breathing chamber 130 which allows the supply of air to the user's airways to be pressurized. Forming the non-face contacting portion 204 from silicone rubber 312 allows the cushion 114 to be lightweight, flexible and durable. Further, the resilient silicone structure can provide support to the face contacting portion 202 which improves ease of fitting the mask to the user.

The face contacting portion 202 is permanently bonded to the non-face contacting portion 204 along the intermediate region 206. That is, the intermediate region 206 is disposed between the face contacting portion 202 and the non-face contacting portion 204. In some configurations, the intermediate region 206 may be substantially defined by an outer perimeter and/or perimetric edge of at least one of the face contacting portion 202 and the non-face contacting portion 204. The face contacting portion 202, the non-face contacting portion 204 and the intermediate region 206 together form an enclosure or breathing chamber 130 having a gas flow inlet from the system 10. As will be discussed in greater detail below, the non-face contacting portion 204 is bonded to the face contacting portion 202 along the intermediate region 206 by an overmolding process. As illustrated, the intermediate region 206 extends around a periphery of the cushion 114. In some configurations, the intermediate region 206 extends at least partially or entirely around a periphery of the cushion 114. In some configurations, the periphery may be defined as an outer edge or extent of the cushion 114. For example, in some configurations, the intermediate region 206 may define an outermost circumferential edge of the cushion 114, as illustrated in the front view of the cushion 114 in FIG. 3B. The outermost circumferential edge of the cushion 114 is a perimetric edge between the forward-facing surface and a rearward-facing surface of the cushion 114. In other configurations, the intermediate region 206 may extend around a periphery of the cushion 114 that is radially inward of the outermost circumferential edge of the cushion 114. In some configurations, the intermediate region 206 may be positioned on a forward or rearward-facing surface of the cushion 114.

The intermediate region 206 comprises a seam 232 and a foam and fabric laminate material impregnated region 234. The seam 232 provides a butt joint between the open cell foam material 310 of the face contacting portion 202 and the silicone rubber 312 of the non-face contacting portion 204. The seam 232 is located on the forward-facing surfaces of the cushion 114 such that the seam 232 does not contact the user's face. The butt joint forms a smooth joint without sharp edges or steps (e.g., a flush surface) between the outer surfaces of the cushion 114. Further, raw edges of the open cell foam material 310 of the thermoformed face contacting portion 202 are sealed by the overmolded silicone rubber 312, which provides a tidy finish and prevents any fraying or degradation at the edges of the face contacting portion 202. The impregnated region 234 is formed by impregnating the face contacting portion 202 with silicone rubber 312 during the overmolding process such that the face contacting portion 202 and the non-face contacting portion 204 are integrally formed. Impregnating the face contacting portion 202 with silicone rubber 312 provides a strong mechanical bond between the open cell foam material 310 and the silicone rubber 312, which may provide support to the face contacting portion 202, improve durability of the cushion 114, etc.

The seam 232 extends along the edge thickness of the face contacting portion 202. In some configurations, the seam 232 extends around the largest perimeter of the cushion (when viewed from the front or rear of the cushion 114) such that the seam 232 defines the perimeter of the face contacting portion 202. In some configurations, the seam 232 may provide a smooth and seamless transition between the face contacting portion 202 and the non-face contacting portion 204. In other configurations, the face contacting portion 202 and the non-face contacting portion 204 may comprise a ridge or protruding portion that extends beyond the outer surfaces of the face contacting portion 202 and the non-face contacting portion 204. The seam 232 may have a constant or variable thickness along its length.

The intermediate region 206 is substantially formed from outer perimeter portions of both the face contacting portion 202 and the non-face contacting portion 204. The impregnated region 234 abuts the seam 232 and extends into the face contacting portion 202 from the seam 232. That is, an outer perimeter of the face contacting portion 202 may be impregnated with silicone rubber 312 along the impregnated region 234. The impregnated region 234 is formed by impregnating the open cell foam material 310 of the face contacting portion 202 with silicone rubber 312 during the overmolding process. That is, the impregnated region 234 is formed by permeating overmolded silicone into the structure of the open cell foam material 310. In some configurations, the open cells of the open cell foam material 310 are filled with silicone rubber 312. In some configurations, the fibers of the textile covering that provides the outer surface 212 are saturated by silicone rubber 312.

The impregnated region 234 extends from the forward facing side of the cushion 114 into the rearward facing side of the face contacting portion 202 from the seam 232. In some embodiments, an overmolding tool can determine the shape, size and geometry of the impregnated region 234. That is, the silicone rubber 312 may be allowed to extend further into the open cell foam material 310 in specified regions such that the impregnated region 234 is wider, deeper and/or thicker in the specified regions relative to other regions. Areas where the silicone rubber 312 extends a distance further into the open cell foam material 310 may be stiffer and less flexible than portions of the open cell foam material 310 where the silicone rubber 312 extends a smaller or shallower distance into the open cell foam material 310. The shape, size and depth of the impregnated region 234 can be tailored to control or provide intentional leak paths and/or provide increased structure in specified regions of the face contacting portion 202.

Manufacturing Process

FIGS. 4A to 4G illustrate the steps for forming the cushion 114 from the open cell foam material 310 and the liquid silicone rubber 312. That is, FIGS. 4A to 4G illustrate the steps for forming the face contacting portion 202 from a sheet of open cell foam material 310 and overmolding the non-face contacting portion 204 from liquid silicone rubber 312 onto the face contacting portion 202 to form the cushion 114 in FIGS. 3A to 3F.

Figure 4A:
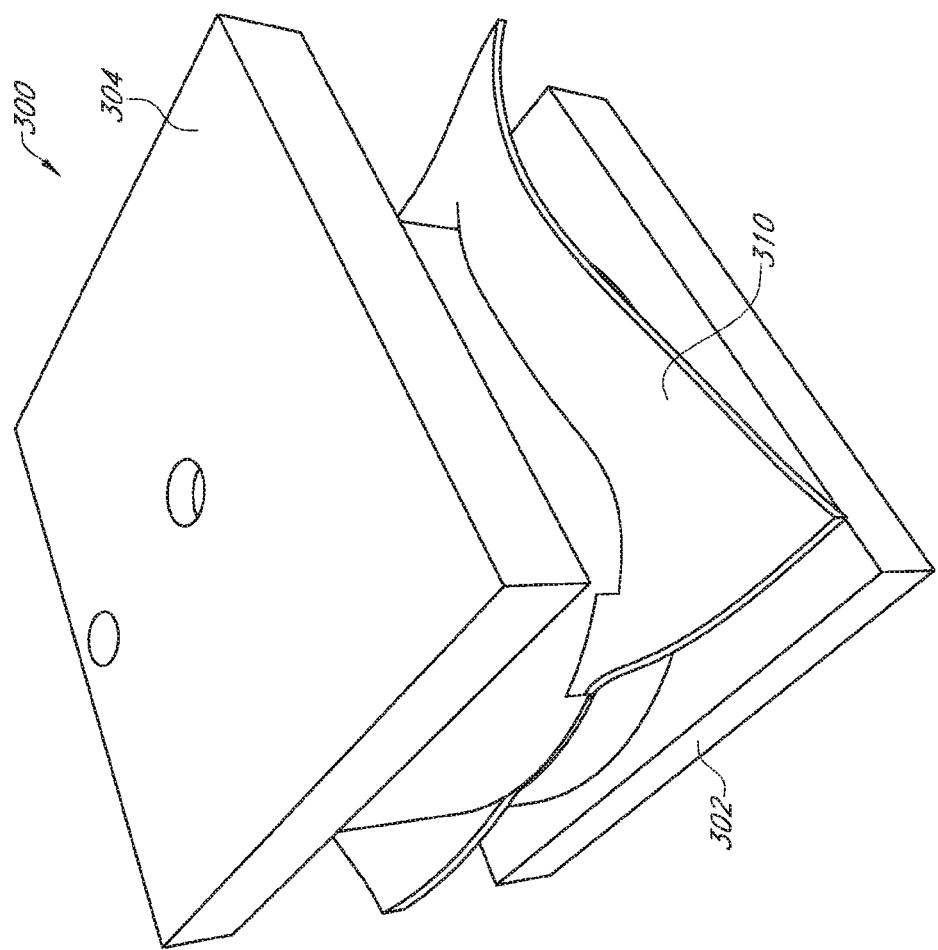
FIG. 4A is a perspective view of an exemplary thermoforming tool during a step in a forming process of the cushion of FIGS. 3A to 3F.

As shown in FIG. 4A, an open cell foam material 310 is placed between first and second thermoforming tool portions 302, 304 of a thermoforming tool 300. The open cell foam material 310 may be in the form of a laminate containing one or more textile sheet layers. The first and second thermoforming tool portions 302, 304 sandwich and compress the open cell foam material 310 such that the open cell foam material 310 conforms to the 3-dimensional contours of the first and second thermoforming tool portions 302, 304. In some configurations, a vacuum may be applied to the first and second thermoforming tool portions 302, 304 to apply a force that causes the open cell foam material 310 to conform to the 3-dimensional contours of the first and second thermoforming tool portions 302, 304 and/or to draw the open cell foam material 310 into the face contacting portion cavity 306 of the first and second thermoforming tool portions 302, 304. The open cell foam material 310 is heated to a forming temperature such that the open cell foam material 310 is plastically deformed according to the geometries of the first and second thermoforming tool portions 302, 304.

Figure 4B:
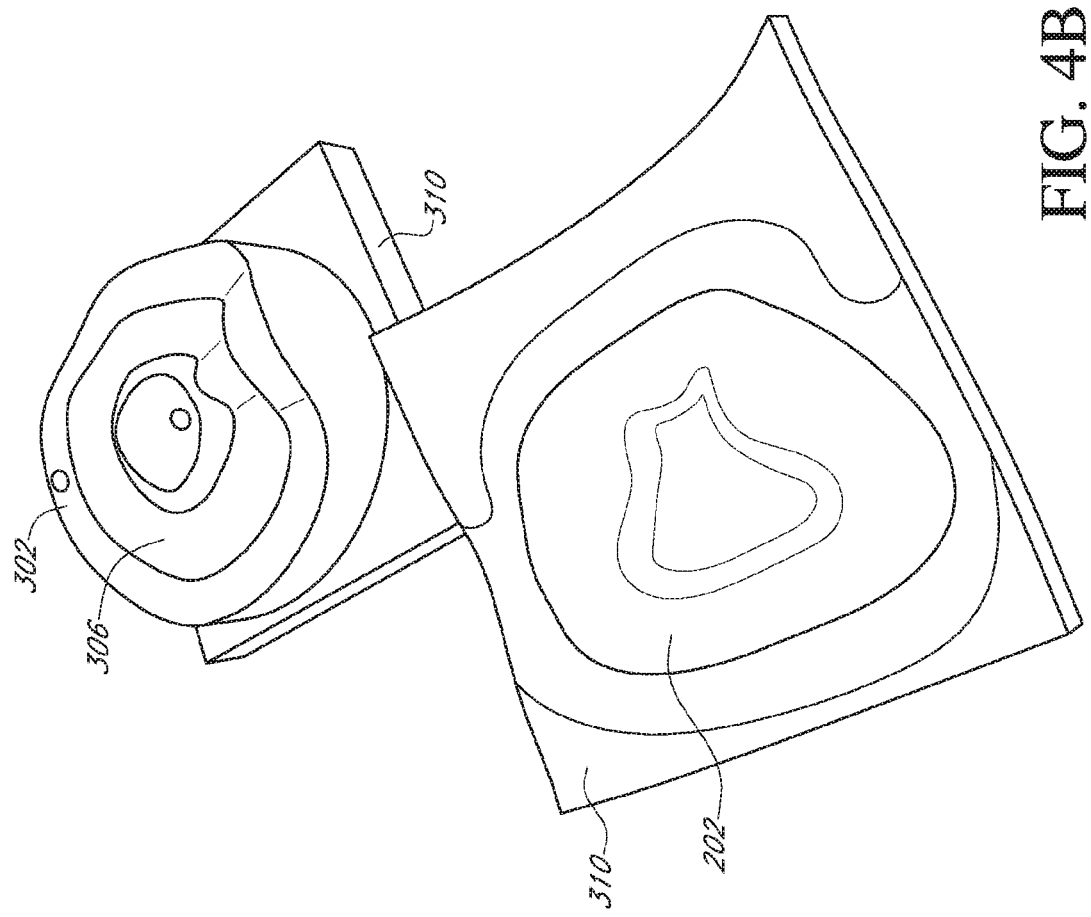
FIG. 4B is a perspective view of the exemplary thermoforming tool and workpiece following a step in the forming process of the cushion of FIGS. 3A to 3F.
Figure 4C:
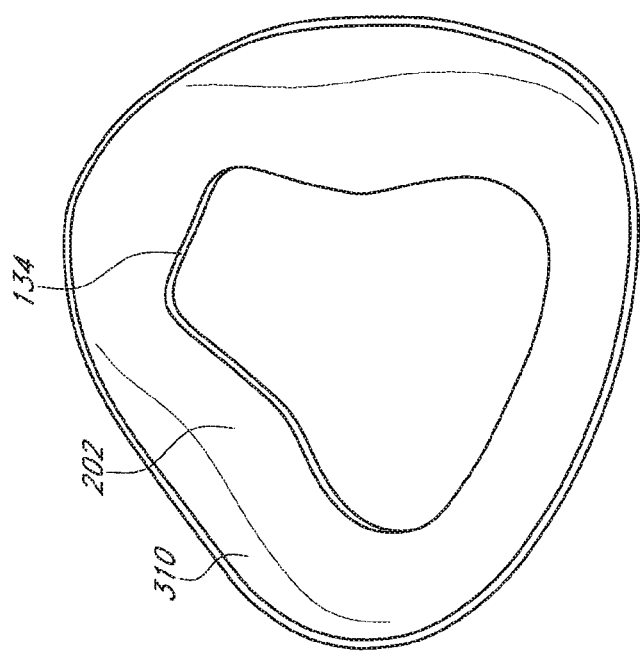
FIG. 4C is a perspective view of an exemplary overmolding tool and a portion of the cushion created from the workpiece following a step in the forming process of the cushion of FIGS. 3A to 3F.

As shown in FIG. 4B, the open cell foam material 310 is cooled and removed from the first and second thermoforming tool portions 302, 304. As shown, the open cell foam material 310 is thermoformed and retains a 3-dimensional contoured shape. As shown in FIG. 4C, the open cell foam material 310 is cut to size and shaped to form the face contacting portion 202 of the cushion 114. That is, the open cell foam material 310 is trimmed and finished to form the outer perimetric edge of the face contacting portion 202 and a hole is formed in the open cell foam material 310 to provide features of the face contacting portion 202, such as the oro-nasal opening 134. In some configurations, the open cell foam material 310 may be die cut, laser cut or the like.

Figure 4D:
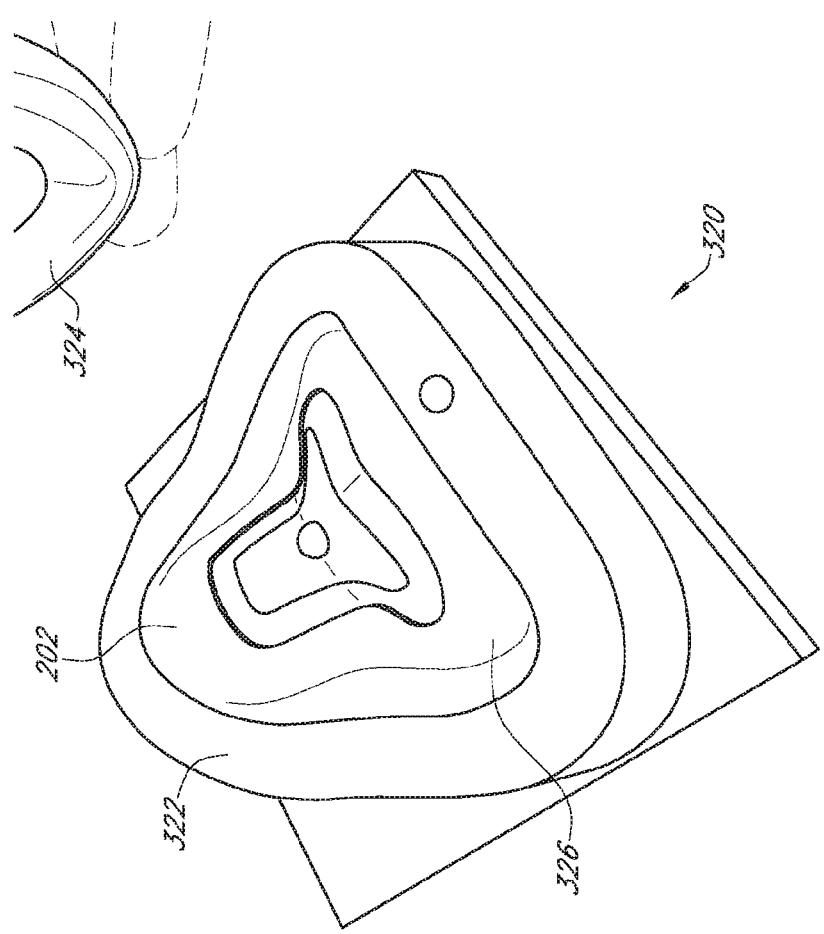
FIG. 4D is a perspective view of the exemplary overmolding tool and the portion of the cushion during a step in the forming process of the cushion of FIGS. 3A to 3F.
Figure 4E:
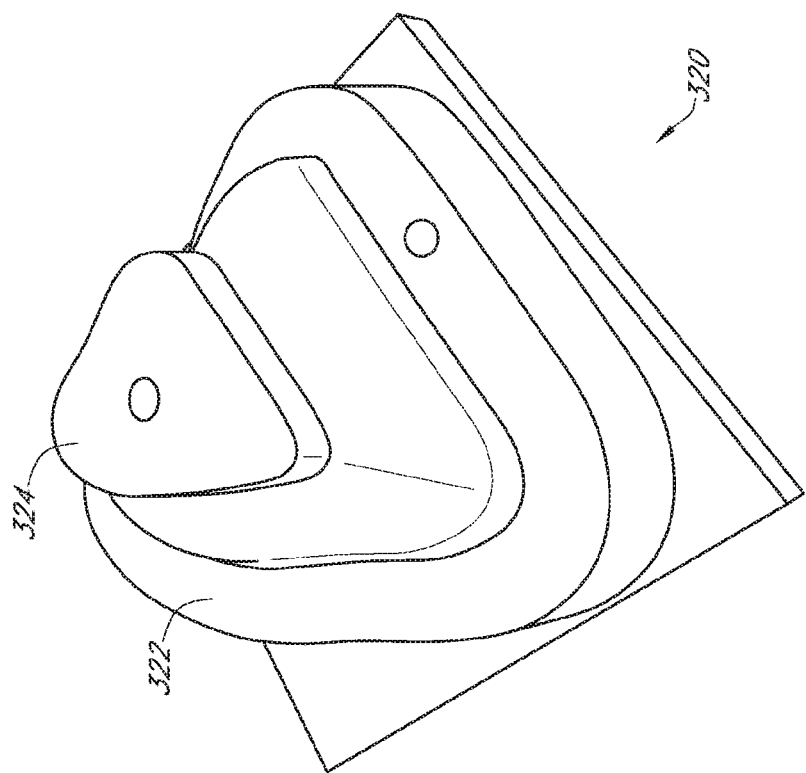
FIG. 4E is a perspective view of the exemplary overmolding tool during a step in the forming process of the cushion of FIGS. 3A to 3F.
Figure 4F:
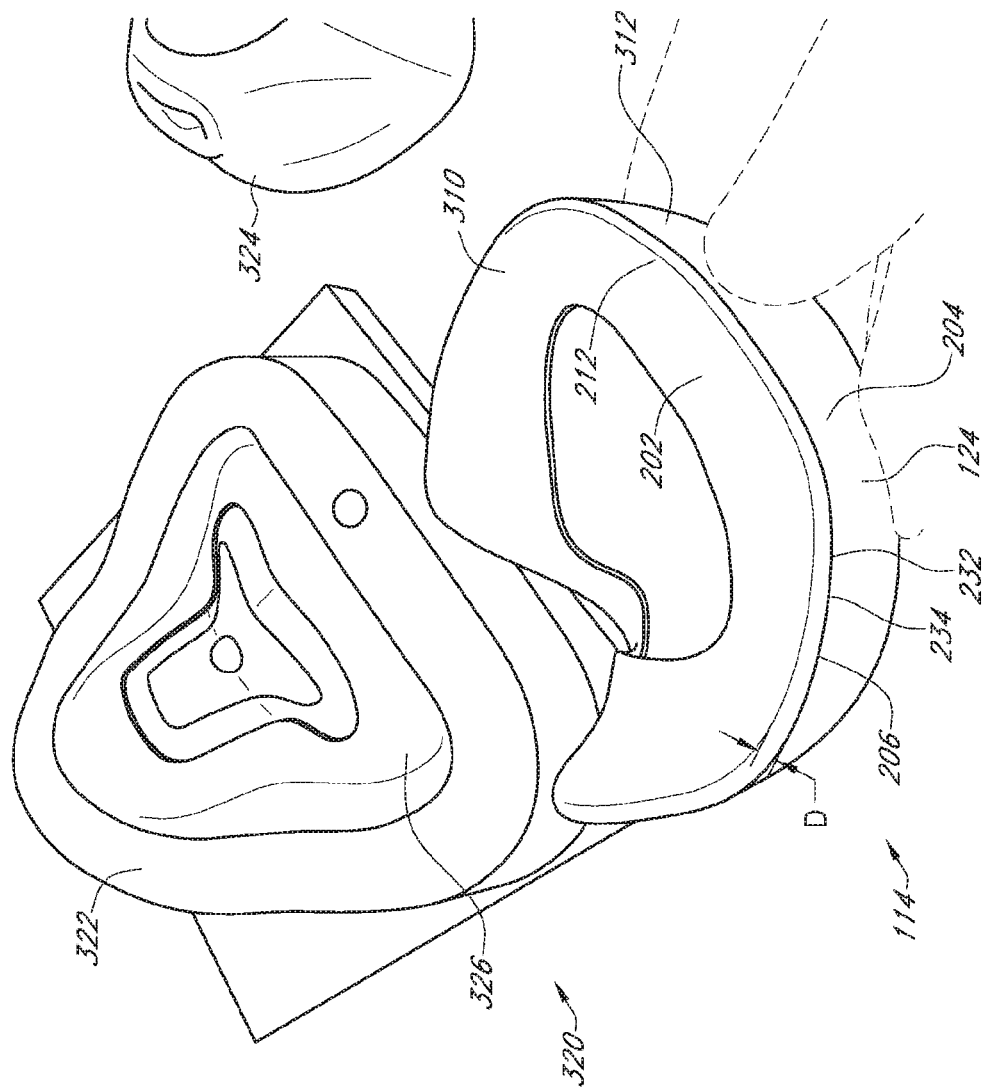
FIG. 4F is a perspective view of the exemplary overmolding tool following a step in the forming process of the cushion of FIGS. 3A to 3F.

As shown in FIG. 4D, the face contacting portion 202 is positioned within an overmolding tool 320. The face contacting portion 202 is inserted within a face contacting portion cavity 326 of a first molding tool portion 322 of the overmolding tool 320. As shown in FIG. 4E, a molding tool core 324 is positioned over the first molding tool portion 322 and enclosed by a second molding tool portion (not shown), and liquid silicone rubber 312 is injected under pressure into the overmolding tool 320 to form the non-face contacting portion 204 and also to join the face contacting portion 202 and the non-face contacting portion 204. The molding tool core 324 functions as an inner core around which the liquid silicone rubber 312 flows for forming the enclosed breathing chamber 130. In some configurations, the overmolding tool 320 may be injected with a thermoplastic material such as thermoplastic polyurethane (TPU), thermoplastic elastomer (TPE), thermoplastic vulcanizate (TPV), etc. After injection, the liquid silicone rubber 312 is cooled and solidified. As shown in FIG. 4F, the cushion 114 is removed from the overmolding tool 320.

During the injection of liquid silicone rubber 312 into the overmolding tool 320, the perimeter of the face contacting portion 202 is impregnated with liquid silicone rubber 312 which forms the intermediate region 206. That is, the liquid silicone rubber 312 is forced to flow into the open outer edges of the face contacting portion 202 such that that the face contacting portion 202 and the non-face contacting portion 204 are joined along their respective edges. The seam 232 is formed between the face contacting portion 202 and the non-face contacting portion 204 and the impregnated region 234 is formed by injecting liquid silicone rubber 312 into the open cell foam material 310 of the face contacting portion 202. The liquid silicone rubber 312 is driven into the open cell foam material 310 to form the impregnated region 234 which extends a distance D into the face contacting portion 202 from the open outer edges of the face contacting portion 202. That is, the distance D indicates the amount of silicone impregnation into the open cell foam material 310 of the face contacting portion 202.

The amount of silicone impregnation into the open cell foam material 310 may vary according to the injection pressure of the liquid silicone rubber 312, the duration of injection time, thickness of the face contacting portion 202 relative to the thickness of the non-face contacting portion 204, etc. In some configurations, the thickness of the face contacting portion 202 is substantially equal to the thickness of the non-face contacting portion 204 such that the liquid silicone rubber 312 does not flow onto the outer surface 212 of the face contacting portion 202. In some configurations, flow into regions of the face contacting portion 202 may be restricted via narrowing or clamping of the face contacting portion 202. For example, the molding tool portions and molding tool core of the overmolding tool 320 may include regions that clamp or narrow the thickness of the open cell foam material 310 of the face contacting portion 202 such that the liquid silicone rubber 312 is inhibited from flowing into the open cell foam material 310.

Partial Foam and Textile Material

Figure 5:
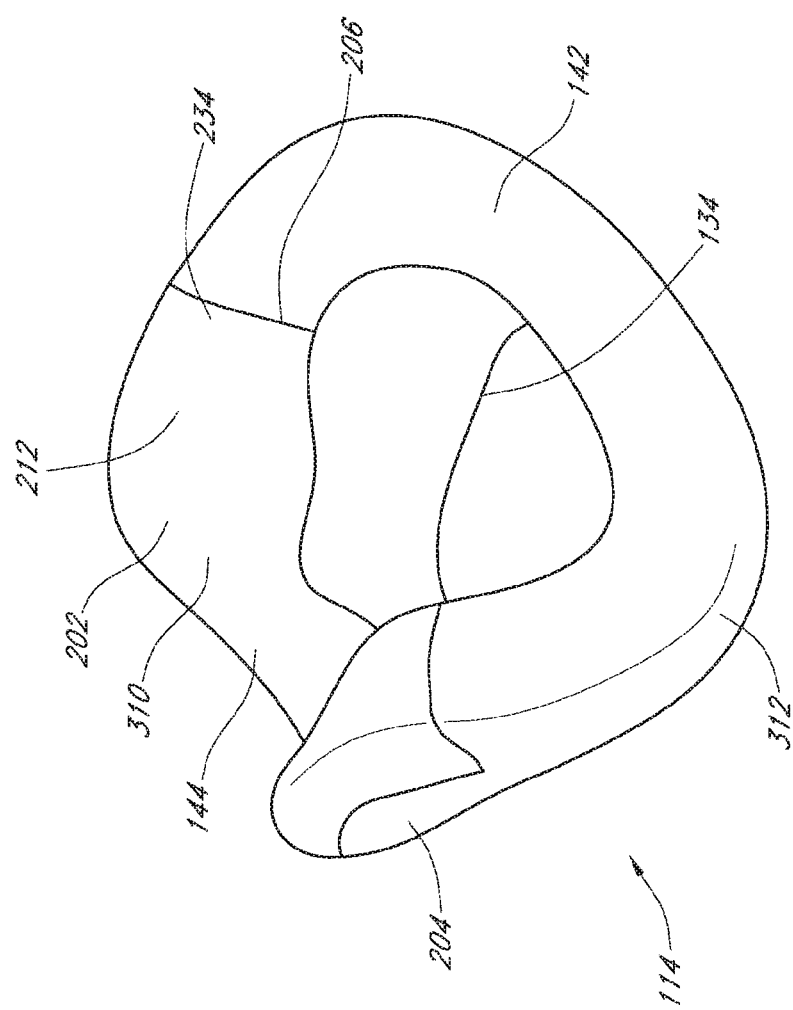
FIG. 5 is a perspective view of an alternative exemplary cushion having a portion of a face contacting portion formed from silicone.
Figure 6A:
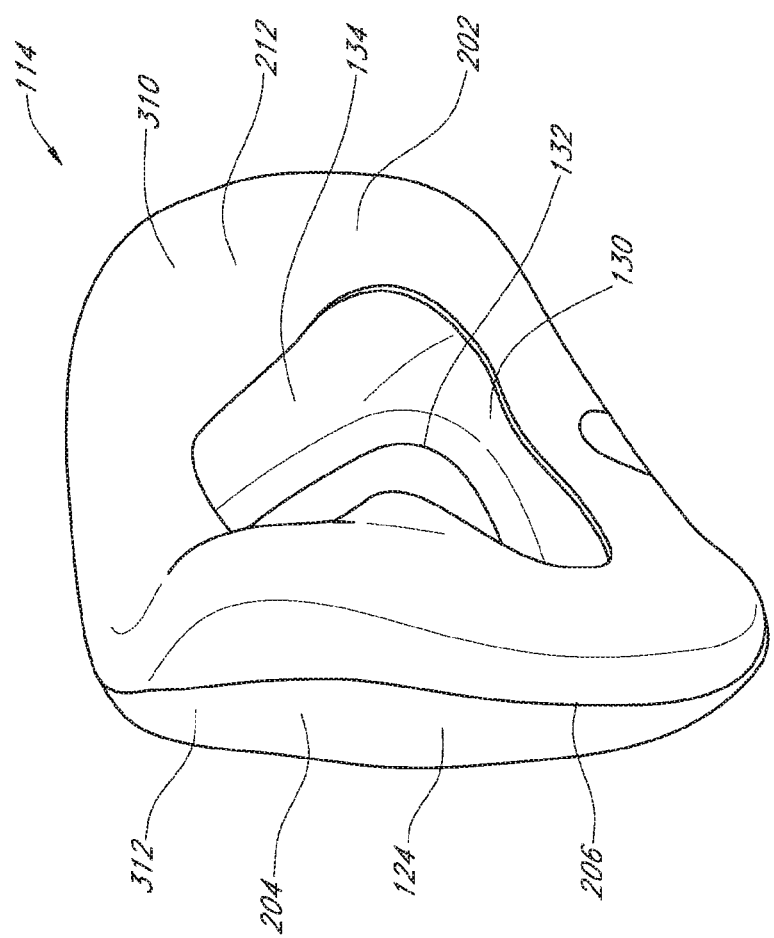
FIG. 6A is a perspective view of an alternative exemplary cushion having a face contacting portion having a textile layer fully impregnated with silicone.
Figure 6B:
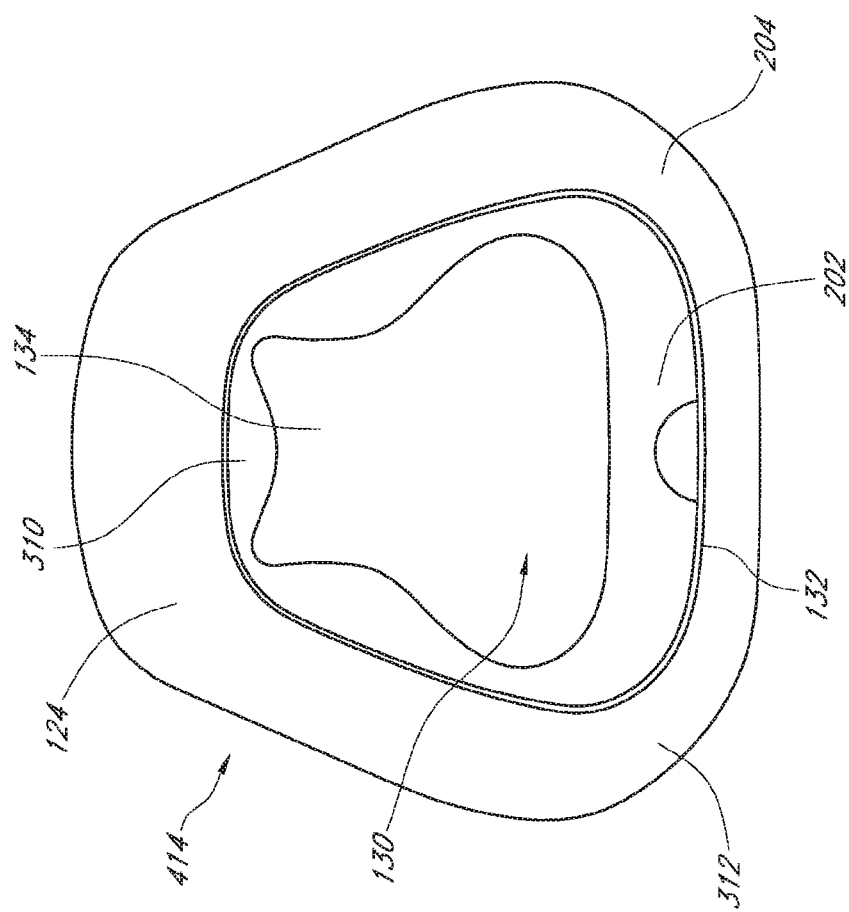
FIG. 6B is a front view of the cushion of FIG. 6A.
Figure 6C:
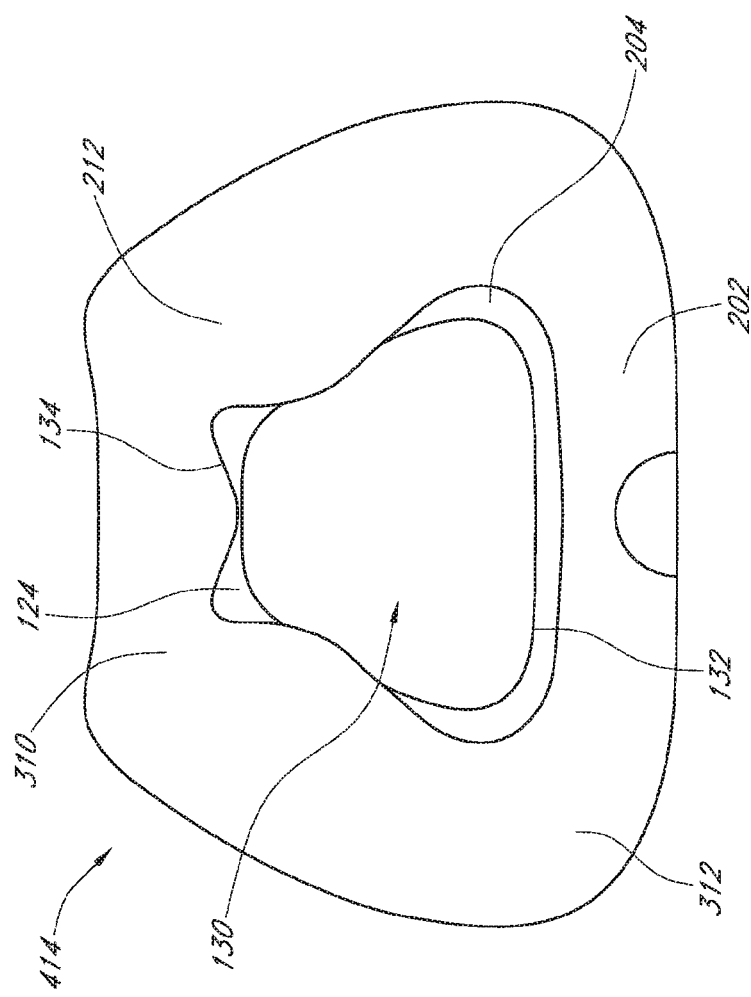
FIG. 6C is a rear view of the cushion of FIG. 6A.
Figure 6D:
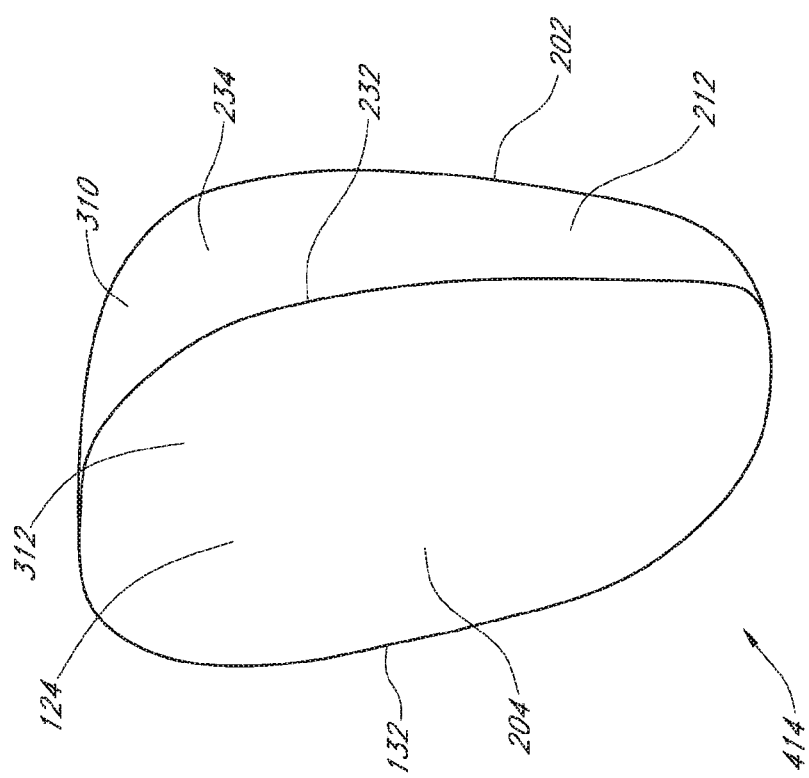
FIG. 6D is a side view of the cushion of FIG. 6A.
Figure 6E:
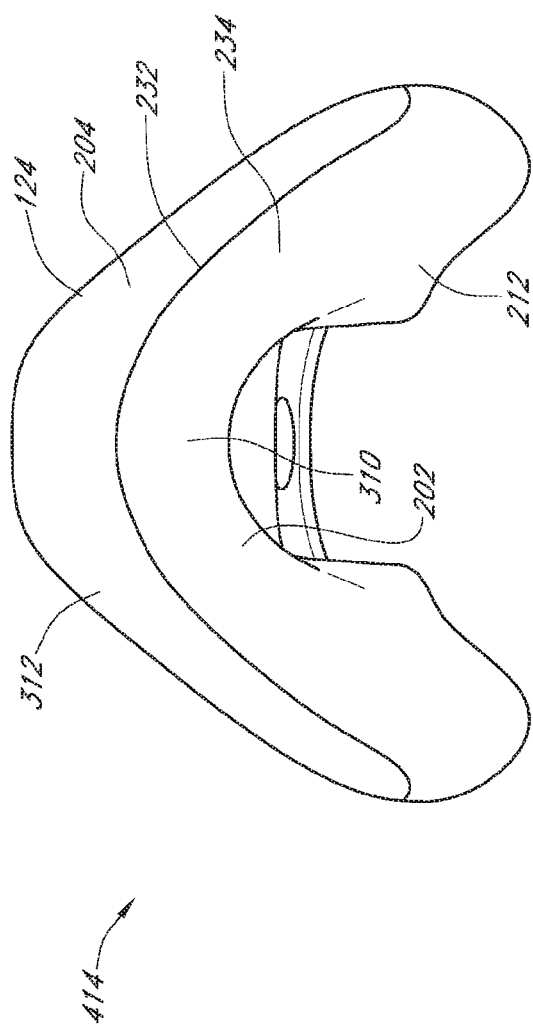
FIG. 6E is a top view of the cushion of FIG. 6A.
Figure 6F:
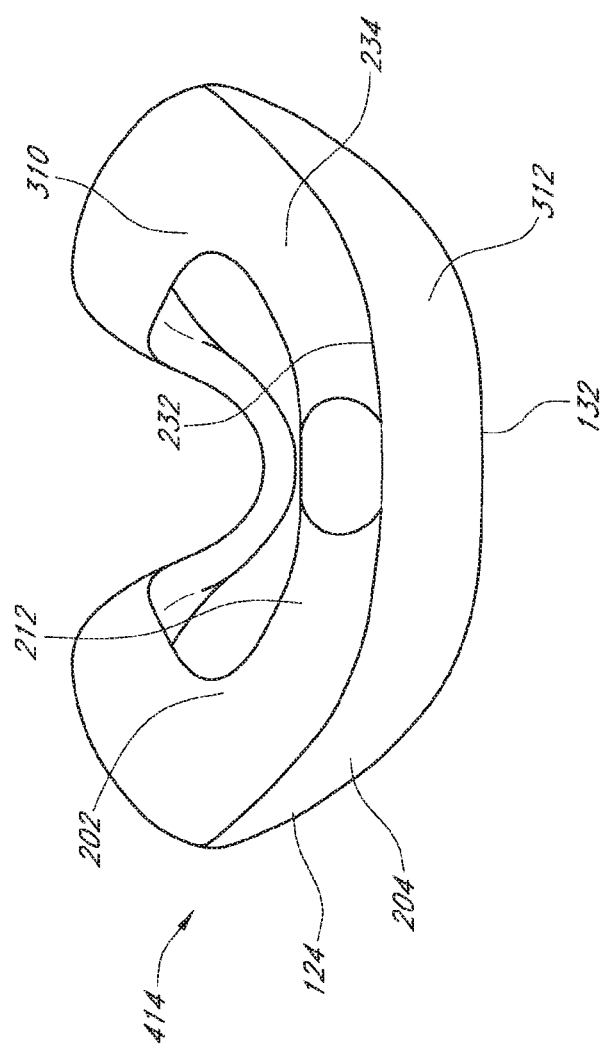
FIG. 6F is a bottom view of the cushion of FIG. 6A.

FIG. 5 illustrates an alternative configuration for a cushion 114 for use with the CPAP system 10 of FIG. 1. Description of certain similarities between the two configurations may be omitted herein for the sake of brevity and convenience, but such omission is not limiting. The cushion 114 is comprised of a face contacting portion 202 and a non-face contacting portion 204. The face contacting portion 202 is comprised of a mouth region 142 and a nasal region 144. The non-face contacting portion 204 is formed from silicone rubber 312. The face contacting portion 202 has regions of silicone rubber 312 and/or open cell foam material 310. More specifically, the nasal region 144 of the face contacting portion 202 is formed from open cell foam material 310 and the mouth region 142 is formed from silicone rubber 312. Forming the nasal region 144 from the open cell foam material 310 provides a soft texture in the user's nasal regions which are more sensitive to pressure, whilst providing a face contacting portion 202 that effectively seals around the user's mouth. In some configurations, the nasal region 144 may be formed from a textile material, a laminate material and/or a foam and fabric laminate material. Similar to cushion 114, the impregnated region 234 is formed by injecting liquid silicone rubber 312 into the open cell foam material 310 of the face contacting portion 202 which provides a strong mechanical bond between the open cell foam material 310 and the silicone rubber 312, which may improve durability of the cushion 114.

The cushion 114 includes an intermediate region 206 with an impregnated region 234 that extends about the perimeter of the open cell foam material 310. As shown in FIG. 5, the intermediate region 206 extends from an outer periphery of the face contacting portion 202 and across the face contacting portion 202 towards the oro-nasal opening 134. In some configurations, a portion of the intermediate region 206 may define a portion of the oro-nasal opening 134.

As illustrated, the cushion 114 has a face contacting portion 202 comprised of continuous portion or region of open cell foam material 310 and a continuous portion or region of silicone rubber 312. In some configurations, the mouth region 142 and the non-face contacting portion 204 are both unitarily formed from continuous silicone rubber 312. That is, the mouth region 142 and the non-face contacting portion 204 are formed from the same material. In other configurations, the mouth region 142 and the non-face contacting portion 204 are formed from different materials.

In some configurations, multiple continuous portions or regions of open cell foam material 310 and/or silicone rubber 312 may be positioned around the face contacting portion 202. For example, the face contacting portion 202 may include a second open cell foam material 310 positioned near a chin contacting portion of the face contacting portion 202. It should be understood to one of ordinary skill in the art that regions of the open cell foam material 310 and/or silicone rubber 312 may be positioned at various regions (i.e., circumferentially around, radially inward/outward, periodically, or any combination thereof, etc.) on the face contacting portion 202 to provide user comfort, breathability, sealability, flexibility, etc. That is, any portion of the open cell foam material 310 may be impregnated with silicone rubber 312.

Fully Impregnated Textile Material

FIGS. 6A to 6F illustrate an alternative configuration for a cushion 414 for use with the CPAP system 10 of FIG. 1. Description of certain similarities between the two configurations may be omitted herein for the sake of brevity and convenience, but such omission is not limiting. The cushion 414 is comprised of a face contacting portion 202 and a non-face contacting portion 204. The face contacting portion 202 comprises a composite material construction including a layer of textile material 310 that is overmolded with silicone rubber 312. In other words, the textile material 310 is fully impregnated by silicone rubber 312 such that the inner and outer surfaces of the face contacting portion are both formed from silicone rubber 312. That is, an entirety of the face contacting portion 202 is comprised of textile material 310 that is impregnated with silicone rubber 312.

The fully impregnated textile material 310 of the face contacting portion 202 provides properties of both the textile material 310 and the silicone rubber 312. The face contacting portion 202 has a textile appearance while providing a silicone rubber surface texture. The textile appearance may provide a softer aesthetic which may be comforting and desirable in a bedroom environment. The textile material 310 may also have a contrasting colour relative to the silicone rubber 312 which provides an aesthetically pleasing appearance. The contrasting colour may also provide visual indication to the user regarding locatability and fitment of the cushion 414 on the user's face. The silicone surface texture provides an airtight face contacting portion that seals easily against a user's face. The fully impregnated textile material 310 also provides support structure and an airtight breathing chamber that allows the supply of air to the user's airways to be pressurized. In some configurations, the airtight structure provided by the fully impregnated textile material 310 may be used in conjunction with porous and air-permeable regions such that airflow may be directed and/or diffused away from the user. The support structure also improves locatability and fitment of the cushion against the user's face. Further, the impregnating silicone rubber 312 provides a resilient structure that allows the face contacting portion 202 to conform to the facial geometries of a variety of users.

In some configurations, the non-face contacting portion 204 may have a greater wall thickness (i.e., thicker) than the face contacting portion 202. That is, the wall thickness of the silicone rubber 312 in the face contacting portion 202 may be thinner than the wall thickness of the silicone rubber 312 in the non-face contacting portion 204 such that the face contacting portion 202 may be more flexible than the non-face contacting portion 204. Thicker non-face contacting portion 204 also provides greater rigidity to the housing 124 and breathing chamber 130 of the cushion 414. In some configurations, the non-face contacting portion 204 may have a substantially equal wall thickness as the face contacting portion 202.

The cushion 414 is manufactured in an overmolding tool similar to the cushion 114. In some configurations, the textile material 310 of the face contacting portion 202 does not require thermoforming (as shown in FIG. 4A) and trimming (as shown in FIG. 4B) prior to being inserted in the overmolding tool 320. More specifically, the textile material 310 is stretched over the first molding tool portion 322 of the overmolding tool 320 prior to being overmolded and then excess is textile material 310 trimmed. In some configurations, the textile material 310 may be positioned within the first molding tool portion 322 and overmolded such that the grain of the textile material 310 follows the curvature of the face contacting portion 202. Orienting the direction of the grain of the textile material 310 relative to the non-face contacting portion 204 and/or the user may improve user comfort, sealability, locatability, aesthetics, etc.

Textile and Silicone Impregnated Join

FIGS. 7A to 7F illustrate an alternative configuration for a cushion 424 for use with the CPAP system 10 of FIG. 1. Description of certain similarities between the two configurations may be omitted herein for the sake of brevity and convenience, but such omission is not limiting. As illustrated, the cushion 424 comprises a user face contacting portion 202 and a non-face contacting portion 204. The non-face contacting portion 204 is formed from a thermoplastic elastomeric material such as silicone rubber 312. In some configurations, the non-face contacting portion 204 may have a greater wall thickness (i.e., thicker) than the face contacting portion 202. In other configurations, the non-face contacting portion 204 may have a substantially equal wall thickness as the face contacting portion 202.

The face contacting portion 202 is comprised of a locating region 242 and a sealing region 244. The sealing region 244 is formed from an elastomeric material such as silicone rubber 312 which provides a smooth and continuous surface that engages the user's face to form an airtight seal about the nose and mouth of the user. The sealing region 244 and the non-face contacting portion 204 may be formed from the same material. For example, both the sealing region 244 and the non-face contacting portion 204 may be formed from silicone rubber 312. In some configurations, the sealing region 244 and the non-face contacting portion 204 may be formed from different materials. The sealing region 244 extends about the perimeter of the locating region 242. That is, the sealing region 244 is positioned radially outward of the locating region 242 relative to the oro-nasal opening 134. In other words, the sealing region 244 surrounds the locating region 242. The sealing region 244 is integrally formed with the non-face contacting portion 204 and may be a portion of the non-face contacting portion 204 that is positioned on a rearward or user-facing side of the cushion 424.

The locating region 242 is formed from a dual-layer textile material 314. The textile layers of the locating region 242 are configured to conform to the user's facial geometry and locate (i.e., visually, tactily, etc.) the cushion on the user's face. In some embodiments, the dual-layer textile material 314 may comprise first and second layers that have different properties. For example, the dual-layer textile material 314 may comprise a laminate material having at least one layer that is air tight, so as to increase the sealing region 244 that contacts the user's face and improve the seal achieved. The dual-layer textile material 314 may also comprise at least one comfort layer, so as to increase the softness, cushioning, texture, breathability, etc. of the locating region 242. In some configurations, the locating region 242 may comprise a single layer or a plurality of layers.

Figure 7A:
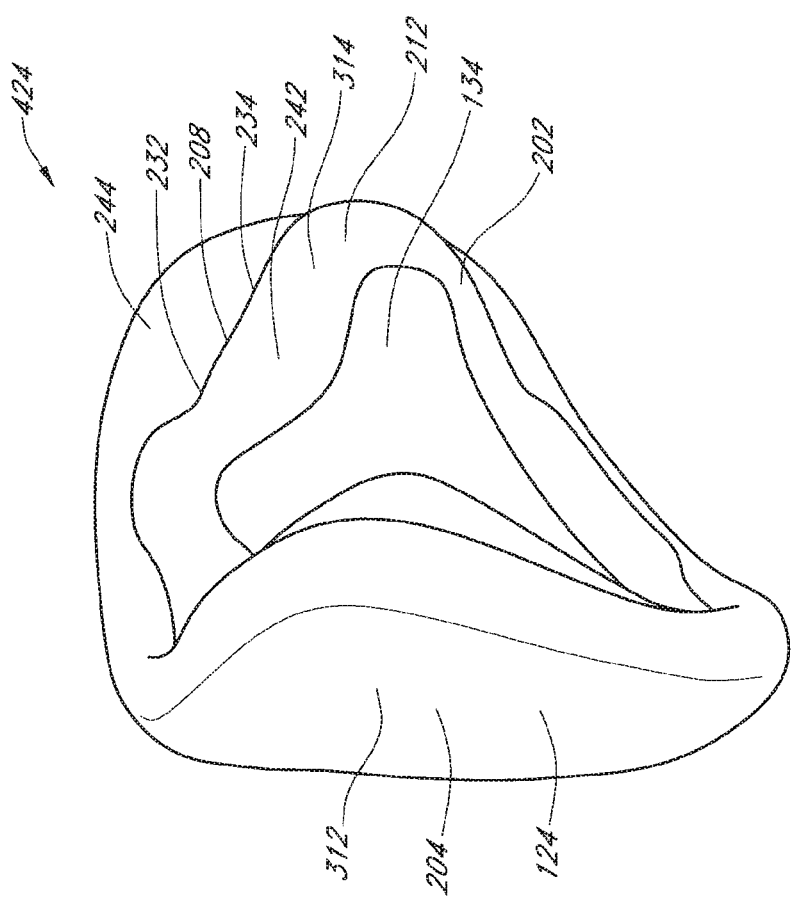
FIG. 7A is a perspective view of another alternative exemplary cushion having a face contacting portion with a sealing region formed from silicone and a locating region formed from a textile layer.
Figure 7B:
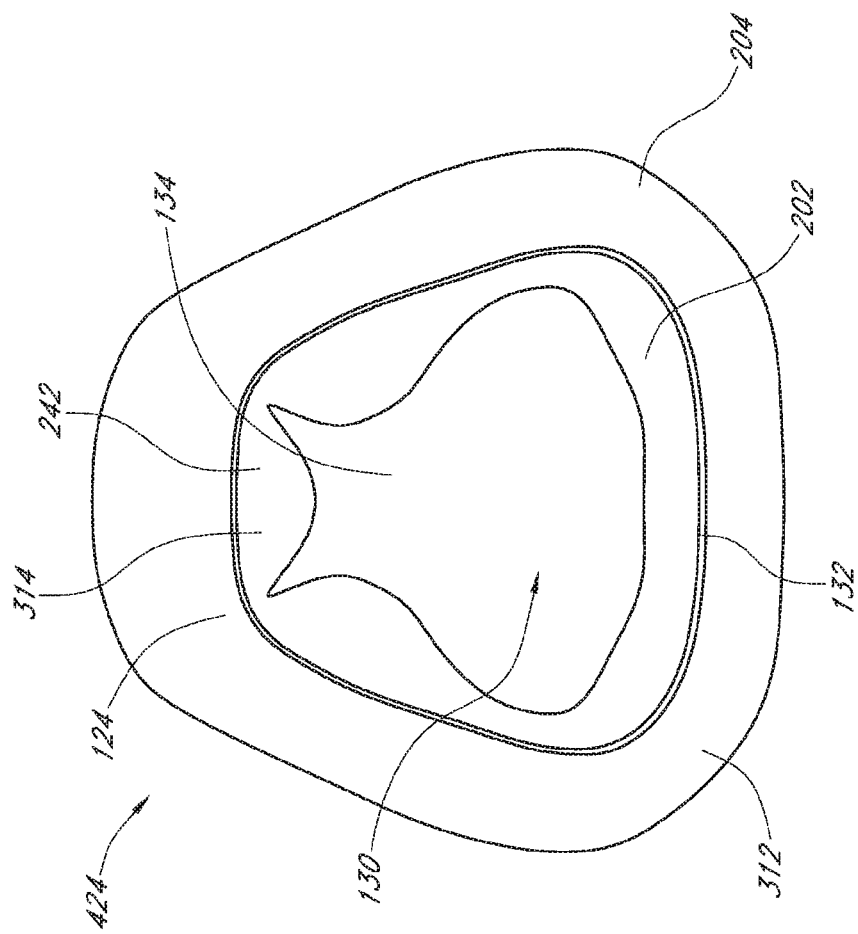
FIG. 7B is a front view of the cushion of FIG. 7A.
Figure 7C:
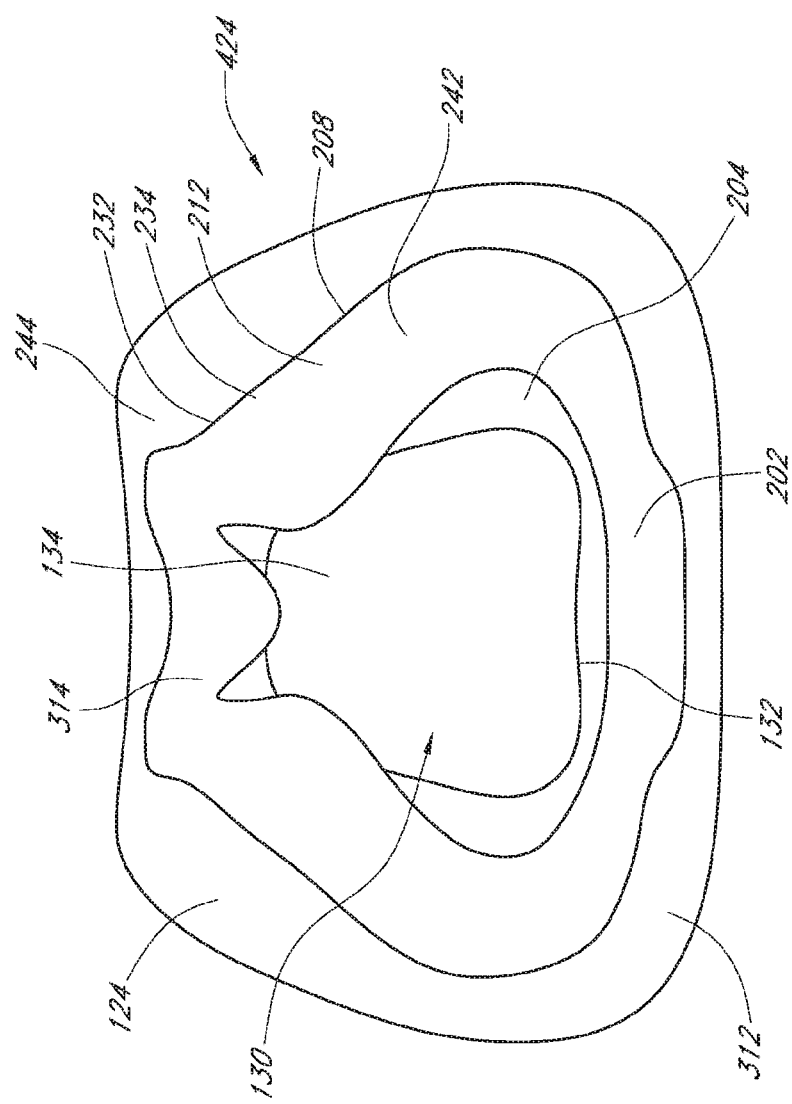
FIG. 7C is a rear view of the cushion of FIG. 7A.
Figure 7D:
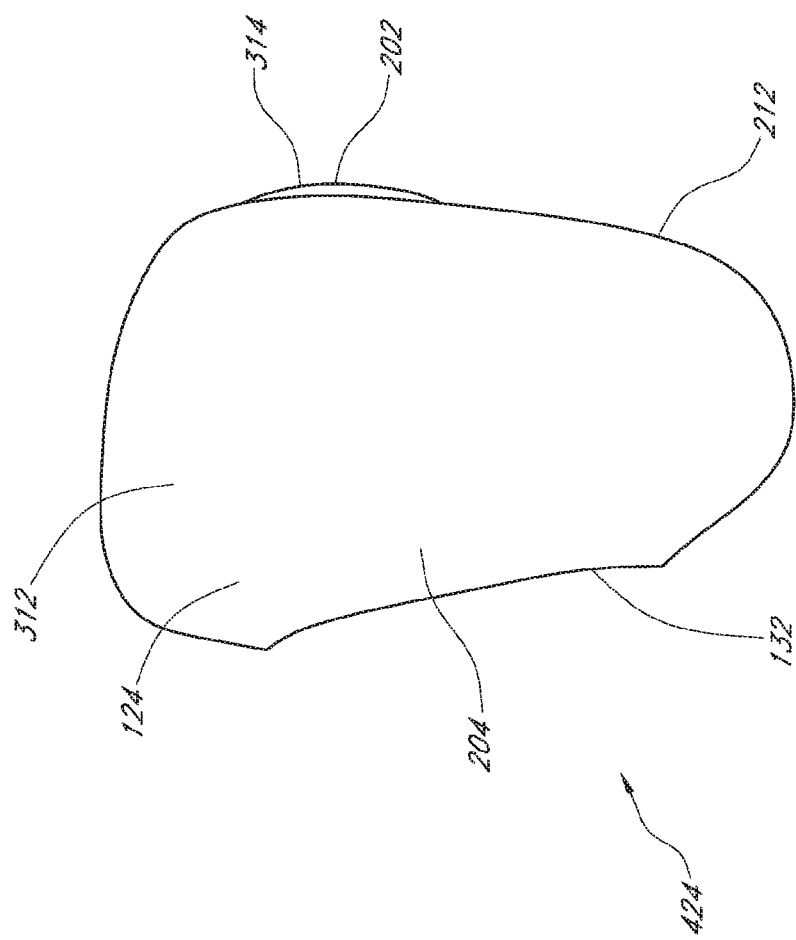
FIG. 7D is a side view of the cushion of FIG. 7A.
Figure 7E:
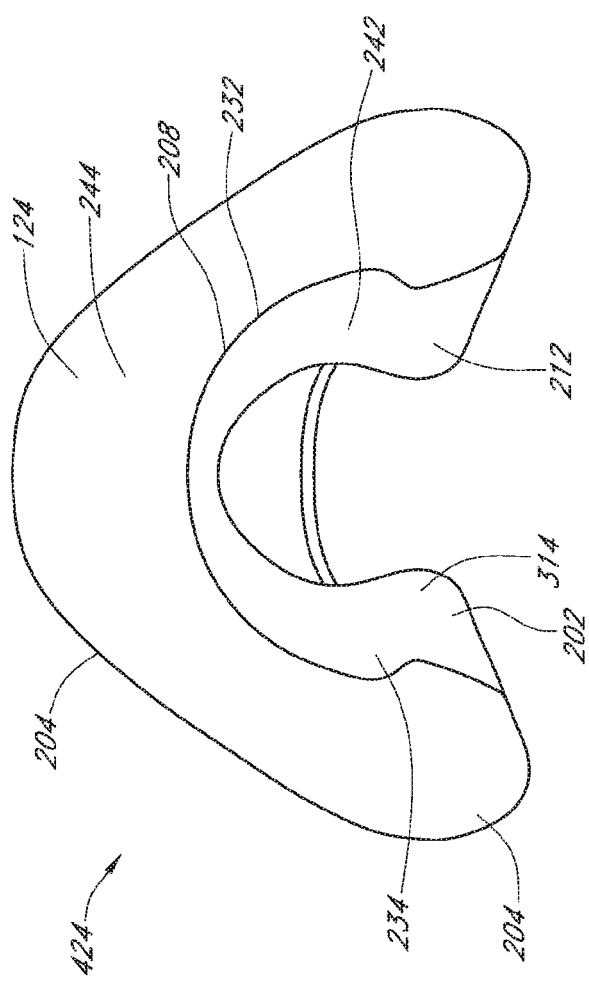
FIG. 7E is a top view of the cushion of FIG. 7A.
Figure 7F:
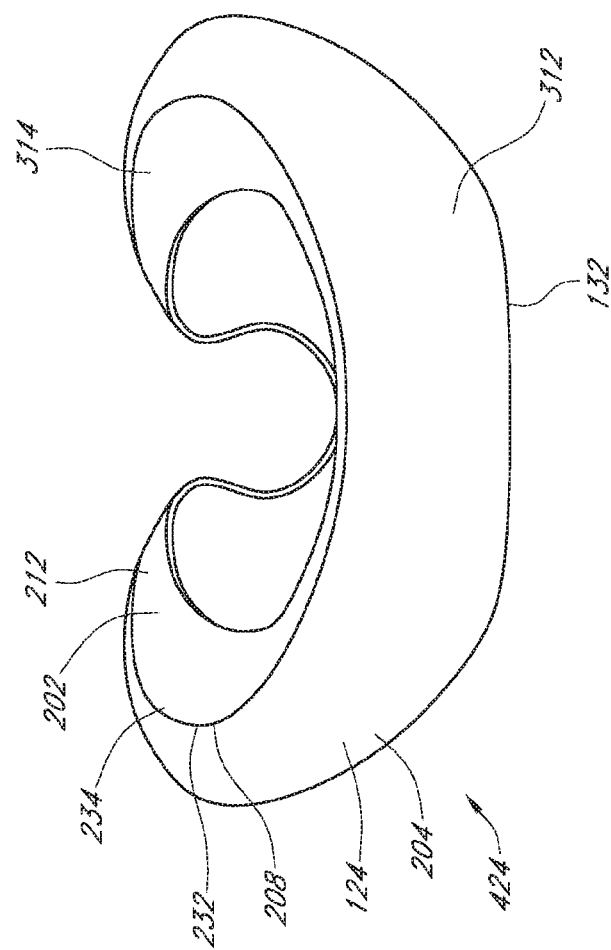
FIG. 7F is a bottom view of the cushion of FIG. 7A.

The dual-layer textile material 314 of the locating region 242 is integrally formed with the sealing region 244. That is, an outer perimeter of the dual-layer textile material 314 is overmolded to the sealing region 244. A transition region 208 is disposed and extends between the locating region 242 and the sealing region 244. As shown in FIGS. 7A and 7C, the transition region 208 may be a perimetric edge between the locating region 242 and the sealing region 244 that is positioned on a rearward- and user-facing surface of the cushion 114. In some configurations, the transition region 208 may be a perimetric edge between the forward-facing surface and a rearward-facing surface of the cushion 424.

The transition region 208 comprises a seam 232 and a textile impregnated region 234. The seam 232 is formed by a transition from the single-layer textile material 316 of the locating region 242 to the silicone rubber 312 of the sealing region 244. The impregnated region 234 is formed by impregnating the dual-layer textile material 314 of the locating region 242 with silicone rubber 312 during the overmolding process such that the locating region 242 and the sealing region 244 are integrally formed. Accordingly, the transition region 208 comprises a composite material of dual-layer textile material 314 and silicone rubber 312. The seam 232 extends around a perimeter of the textile impregnated region 234 and may provide a smooth and seamless transition between the locating region 242 and the sealing region 244. The impregnated region 234 extends about the outer radial perimeter of the dual-layer textile material 314, where the silicone rubber 312 permeates into the dual-layer textile material 314 from the seam 232. The transition region 208 and sealing region 244 are configured to form a substantially airtight seal against a user's face.

Similar to the impregnation process previously described, the impregnated region 234 is formed by impregnating the dual-layer textile material 314 with silicone rubber 312 using the overmolding tool 320. The overmolding tool 320 can determine the size and shape of the impregnated region 234. That is, the silicone rubber 312 may be allowed to permeate specific regions of the dual-layer textile material 314 to provide an impregnated region 234 with a shape that improves the seal with the user's face. Similarly, the silicone rubber 312 may also be restricted or inhibited from permeating specific regions of the dual-layer textile material 314 to provide an impregnated region 234 with a shape that permits airflow through the locating region 242. In some embodiments, the silicone rubber 312 of the impregnated region 234 can have a variable thickness (i.e. can be thicker in some regions than others).

The cushion 424 is manufactured in an overmolding tool similar to the cushion 114. In some configurations, the dual-layer textile material 314 of the face contacting portion 202 does not require thermoforming (as shown in FIG. 4A) and trimming (as shown in FIG. 4B) prior to being inserted in the overmolding tool 320. More specifically, the dual-layer textile material 314 is cut to size and positioned within the first molding tool portion 322 of the overmolding tool 320 prior to being overmolded.

The dual-layer textile material 314 of the locating region 242 provides a 3-dimensional geometry that is softer to the touch than a silicone rubber surface and provides a colour detail to the seal. Accordingly, the cushion 424 is more comfortable against a user's face and has an appearance that is comforting and desirable in a bedroom environment. The dual-layer textile material 314 of the locating region 242 also provides flexibility and conformance to the face contacting portion 202 as a result of the pliable nature of the dual-layer textile material 314. In some configuration, the dual-layer textile material 314 of the locating region 242 may be formed such that a portion of the dual-layer textile material 314 is under tension. That is, tension may be induced within the dual-layer textile material 314 during the overmolding process. The tension may provide some resilience to enable the cushion 424 to be positively located on the user's face.

Sub-Nasal Sling

Figure 8:
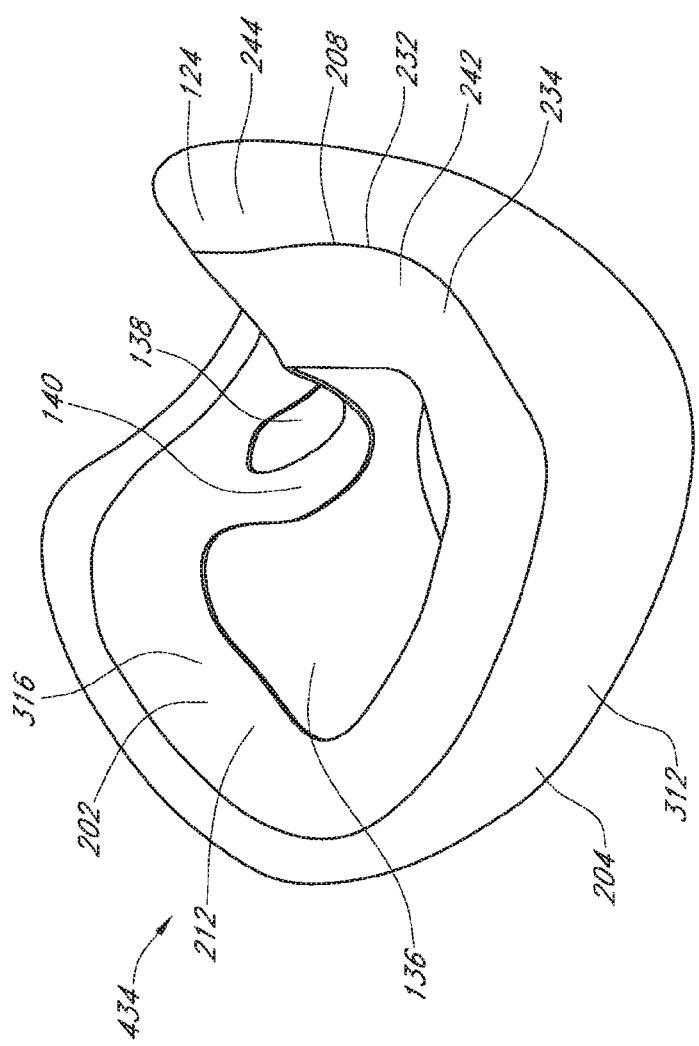
FIG. 8 is a perspective view of another alternative exemplary cushion having a face contacting portion with a sub-nasal sling.

FIG. 8 illustrates an alternative configuration for a cushion 434 for use with the CPAP system 10 of FIG. 1.

Description of certain similarities between the two configurations may be omitted herein for the sake of brevity and convenience, but such omission is not limiting. As illustrated, the cushion 434 comprises a face contacting portion 202 and a non-face contacting portion 204. The face contacting portion 202 is comprised of a locating region 242 and a sealing region 244. The locating region 242 of the face contacting portion 202 is comprised of a single-layer textile material 316 that is integrally formed with the sealing region 244. An outer perimeter of the single-layer textile region 316 is overmolded to the sealing region 244. In some configurations, the locating region 242 may comprise a textile material having multiple layers. In some configurations, the locating region 242 may comprise a continuous surface that is formed from a breathable material such that, in use, a supply of breathing gas can be provided to a user's airways through the locating region.

The locating region 242 includes two openings including an oral opening 136 and a nasal opening 138. The oral opening 136 is configured to encircle the user's mouth and the nasal opening 138 is configured to encircle the user's nares. That is, the oral opening 136 is configured to provide a supply of breathing gases to the user's mouth and the nasal opening 138 is configured to provide a supply of breathing gases to the user's nares. The oral and nasal openings 136, 138 form a sub-nasal sling 140 that is a strip of textile material that extends laterally across the face contacting portion 202. The sub-nasal sling 140 is configured to be located below the user's nose to help locate and prevent the cushion 434 from riding up the user's face. That is, the sub-nasal sling 140 inhibits improper fitment of the cushion 434 by preventing the user's nose from penetrating too deeply into the cushion 434. The sub-nasal sling 140 may be formed by cutting holes for the oral and nasal openings 136, 138 in the single-layer textile material 316. In some configurations, the sub-nasal sling 140 is defined by the oral and nasal openings 136, 138.

A transition region 208 is disposed between the locating region 242 and the sealing region 244. The transition region 208 comprises a seam 232 and a textile impregnated region 234. The seam 232 is formed by a transition from the single-layer textile material 316 of the locating region 242 to the silicone rubber 312 of the sealing region 244. The impregnated region 234 is formed by impregnating the single-layer textile material 316 of the locating region 242 with silicone rubber 312 during the overmolding process such that the locating region 242 and the sealing region 244 are integrally formed. Accordingly, the transition region 208 comprises a composite material of single-layer textile material 316 and silicone rubber 312. The seam 232 extends around a perimeter of the textile impregnated region 234 and may provide a smooth and seamless transition between the locating region 242 and the sealing region 244.

Textile and Silicone Impregnated Join

Figure 9A:
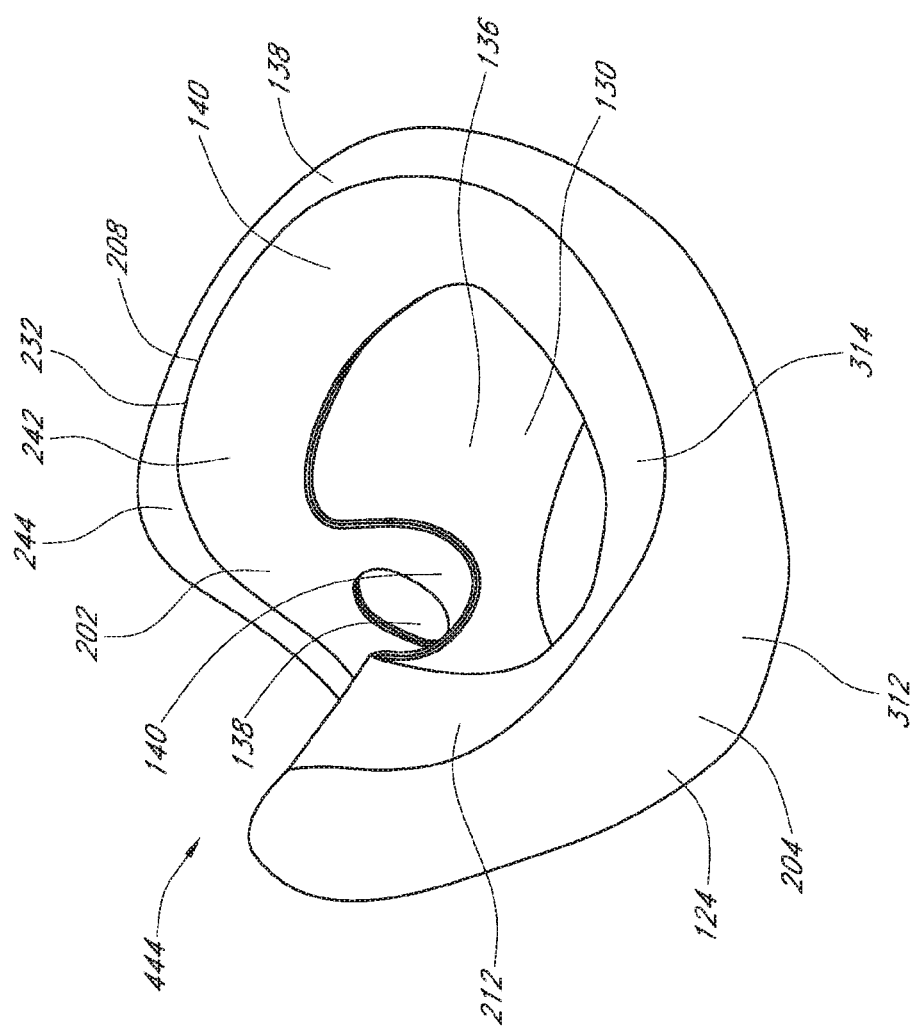
FIG. 9A is a perspective view of another alternative exemplary cushion having a face contacting portion with a raised bead on an internal surface.
Figure 9B:
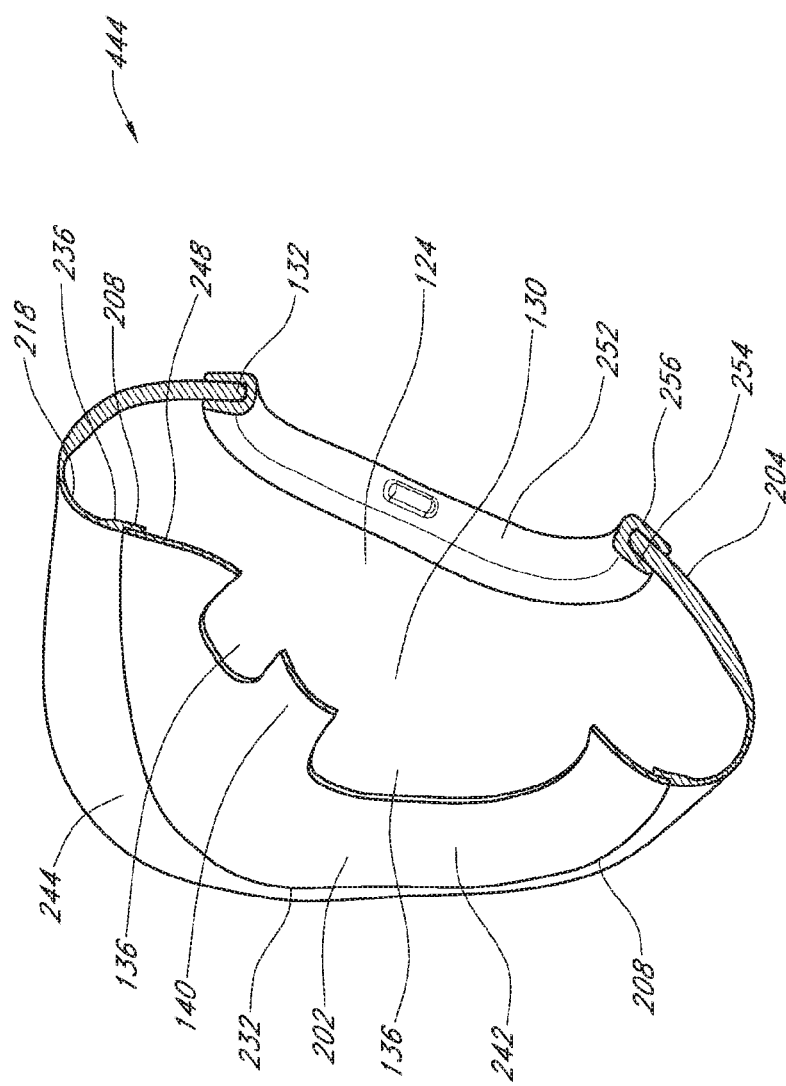
FIG. 9B is a side cross-sectional view of the cushion of FIG. 9A.
Figure 9C:
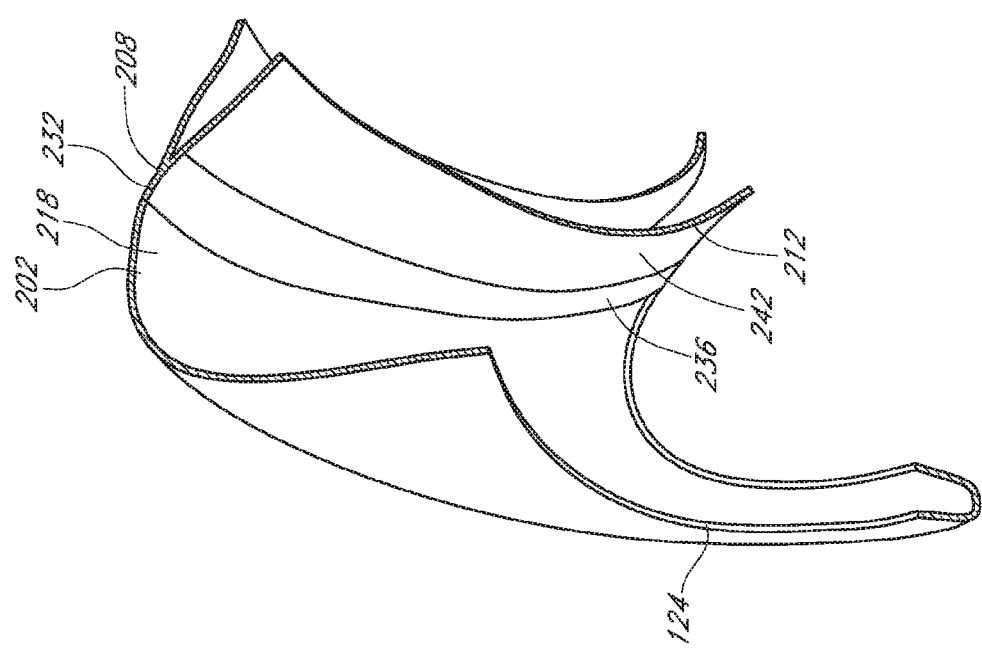
FIG. 9C is a side cross-sectional cutaway view of the cushion of FIG. 9A.

FIGS. 9A to 9C illustrate an alternative configuration for a cushion 444 for use with the CPAP system 10 of FIG. 1. Description of certain similarities between the two configurations may be omitted herein for the sake of brevity and convenience, but such omission is not limiting. Similar to the cushion 434 of FIG. 8, the cushion 444 is comprised of locating region 242 includes two openings including an oral opening 136 and a nasal opening 138 which define a sub-nasal sling 140.

In contrast to the cushion 434 of FIG. 8, the cushion 444 has a transition region 208 comprised of a seam 232 with a raised bead 236 on an internal surface 218 of the face contacting portion 202. The raised bead 236 is a portion of the face contacting portion 202 that extends inwards toward the enclosed breathing chamber 130. As such, the seam 232 has an increased thickness that extends from an interior surface of the transition region towards the interior of the cushion 444. The raised bead 236 extends around the seam 232 along the perimeter of the locating region 242. The raised bead 236 extends onto an internal or interior-facing surface 248 of the dual-layer textile material 314. FIG. 9B illustrates the raised bead 236 applied to a locating region 242 formed from a single-layer textile region 316. FIG. 9C illustrates the raised bead 236 applied to a locating region 242 formed from a dual-layer textile region 314. The raised bead 236 is configured to provide increased bonding and structural strength to the seam 232. The increased thickness of the raised bead 236 is provided on the internal surface 218 of the face contacting portion 202 so that the raised bead 236 does not interrupt the ability of the face contacting portion 202 to form a seal against the user's face. That is, the outer surface of the face contacting portion 204 is a smooth, continuous surface which provides increased bonding and structural strength while also providing a comfortable surface against the user's face and a substantially airtight seal.

Silicone Impregnated Textile Sealing Region without Opening

FIGS. 10A to 10F illustrate an alternative configuration for a cushion 454 for use with the CPAP system 10 of FIG. 1. Description of certain similarities between the two configurations may be omitted herein for the sake of brevity and convenience, but such omission is not limiting. Similar to the cushion 114 of FIG. 8, the cushion 454 comprises a user face contacting portion 202 and a non-face contacting portion 204. In contrast to the cushion 114, the cushion 454 lacks an oro-nasal opening. The face contacting portion 202 of cushion 454 comprises a continuous and uninterrupted sheet of stretchable textile material 318 without openings to receive the user's nose and/or mouth. The face contacting portion 202 comprises a breathable locating region 238 and a sealing region 244. The breathable locating region 238 is porous and air permeable such that pressurized gases within the breathing chamber 130 are received by the user through the stretchable textile material 318. In other words, the user is able to breathe through the breathable locating region 238. In some configurations, the sealing region 244 is formed from a composite material such as a silicone rubber impregnated open cell foam or textile material. In other configurations, the sealing region 244 is formed from silicone rubber 312. The sealing region 244 extends about the perimeter of the breathable locating region 238. That is, the sealing region 244 is positioned radially outward of the breathable locating region 238 relative to the oro-nasal opening 134. In other words, the sealing region 244 surrounds the breathable locating region 238.

Figure 10A:
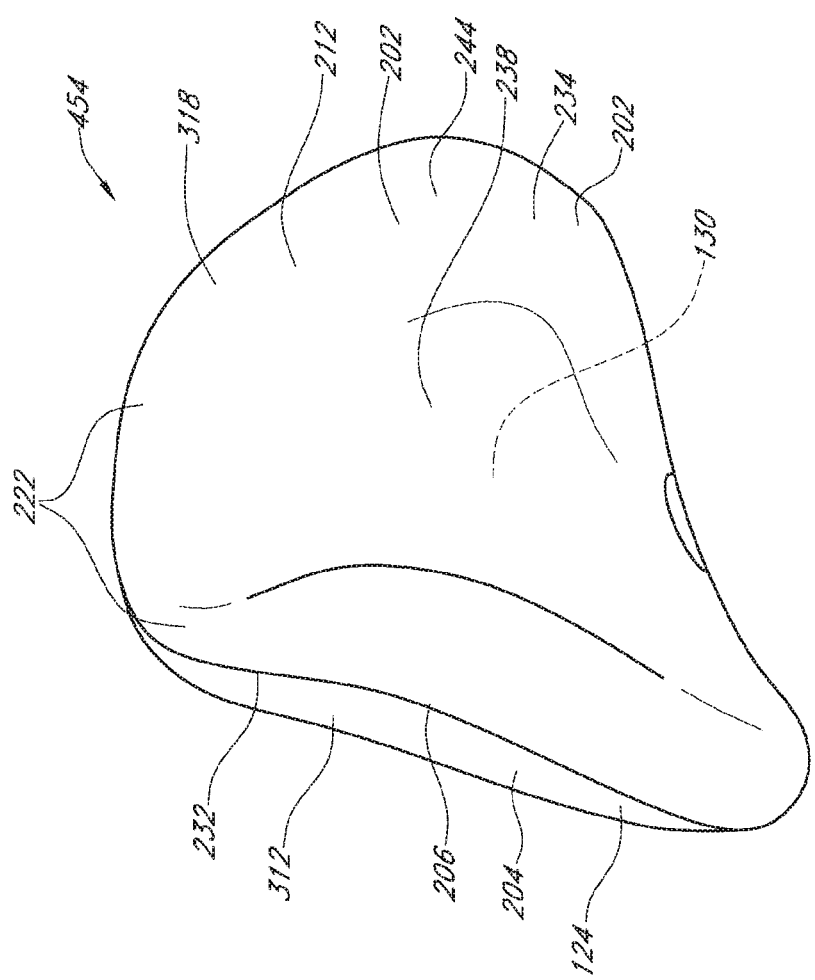
FIG. 10A is a perspective view of another alternative exemplary cushion having a face contacting portion comprising a breathable locating region formed from a continuous textile surface.
Figure 10B:
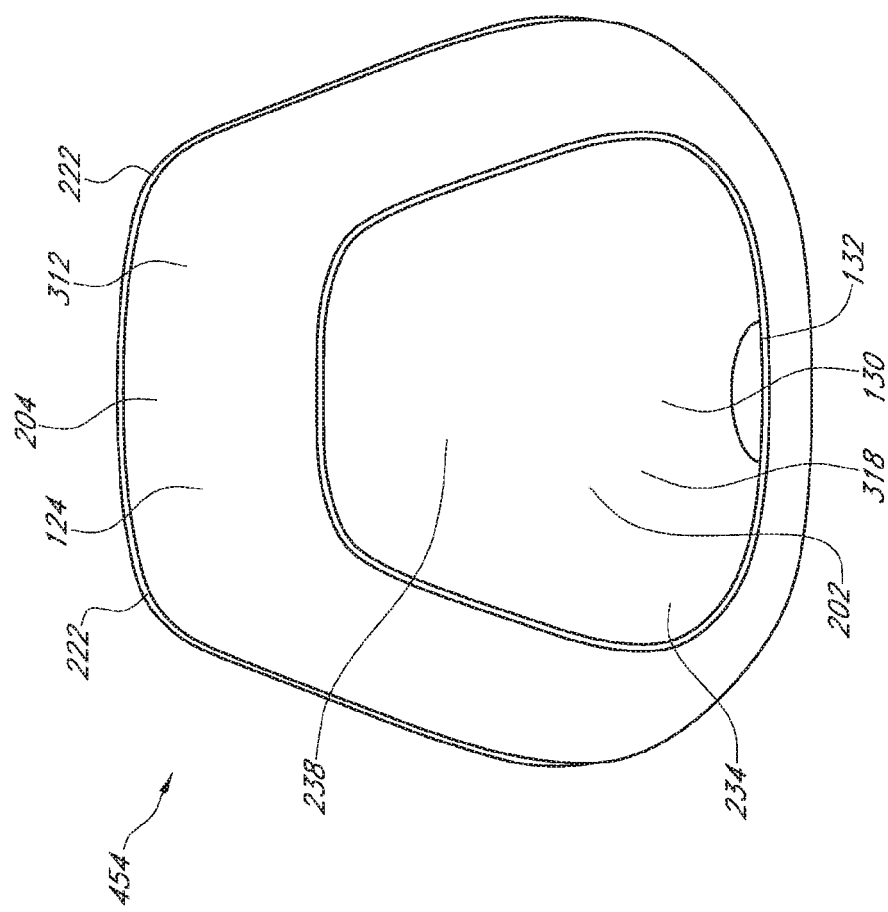
FIG. 10B is a front view of the cushion of FIG. 10A.
Figure 10C:
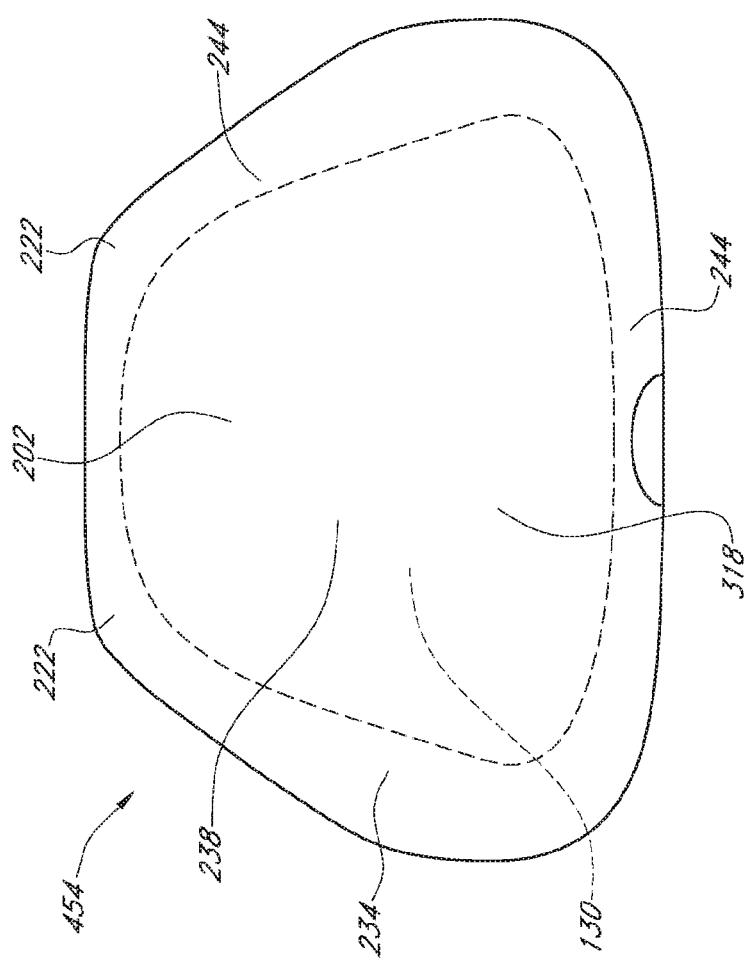
FIG. 10C is a rear view of the cushion of FIG. 10A.
Figure 10E:
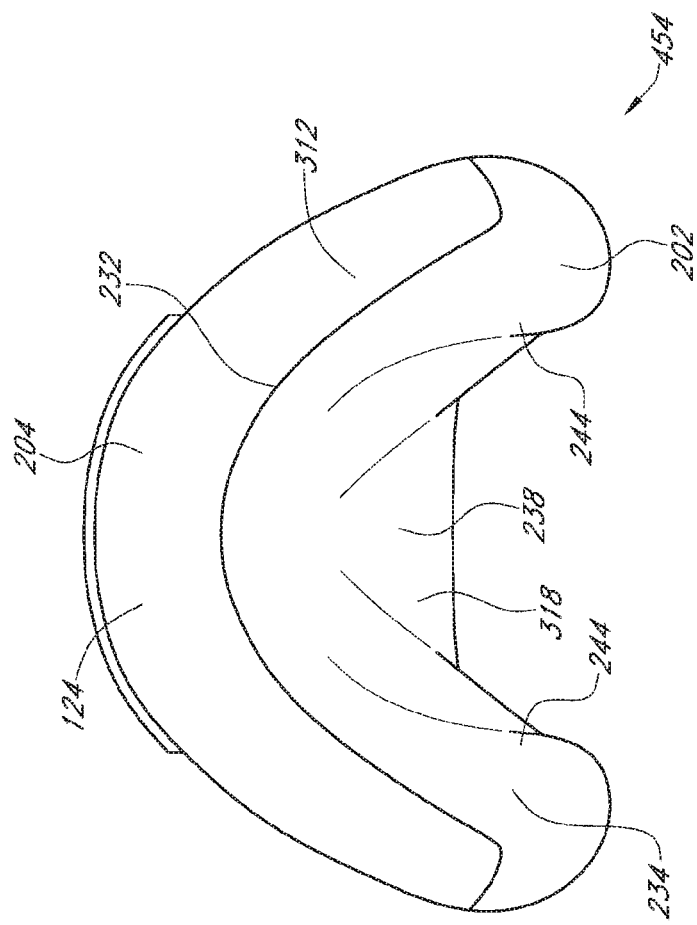
FIG. 10E is a top view of the cushion of FIG. 10A.
Figure 10F:
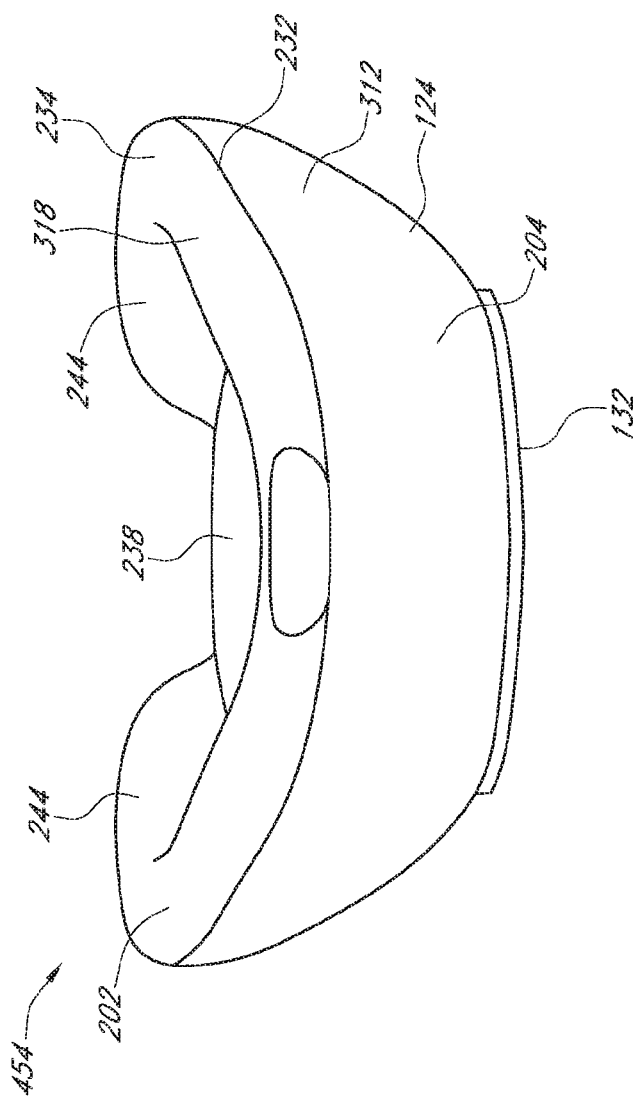
FIG. 10F is a bottom view of the cushion of FIG. 10A.

Similar to the cushion 114 of FIG. 8, the non-face contacting portion 204 is bonded to an outer perimeter of the face contacting portion 202 along the intermediate region 206 by an overmolding process. That is, the non-face contacting portion 204 includes an impregnated region 234 where the stretchable textile material 318 is impregnated with silicone rubber 312 along an outer perimeter of the stretchable textile material 318. The non-impregnated breathable locating region 238 of the stretchable textile material 318 is positioned radially inward of the impregnated region 234. That is, an outer perimeter of the face contacting portion 202 is impregnated with silicone rubber 312 and an interior region of the face contacting portion 202 is not impregnated with silicone rubber 312. An outer perimeter of the breathable locating region 238 is defined an inner perimeter of the impregnated region 234. As illustrated in FIG. 10C, the inner perimeter of the impregnated region 234 and the outer perimeter of the breathable locating region 238 are defined by a dashed line.

The stretchable textile material 318 of the breathable locating region 238 has a predetermined three-dimensional contour at least partially determined by the geometry of the sealing surface, when not in use. The stretchable textile material 318 is supported under tension by the sealing region 244 in order to form the predetermined three-dimensional contour. That is, portions of the stretchable textile material 318 may be under tension such that the breathable locating region 238 has a contoured shape when not in use and no forces are applied to the breathable locating region 238. The breathable locating region 238 may be formed from a material that is stretchable in a single axis, dual axis or multiple axes. Providing axes of stretching may dictate how the breathable locating region 238 stretches when donned by the user. In some configurations, the breathable locating region 238 may be formed from a non-stretchable textile, foam or laminate material.

Figure 11A:
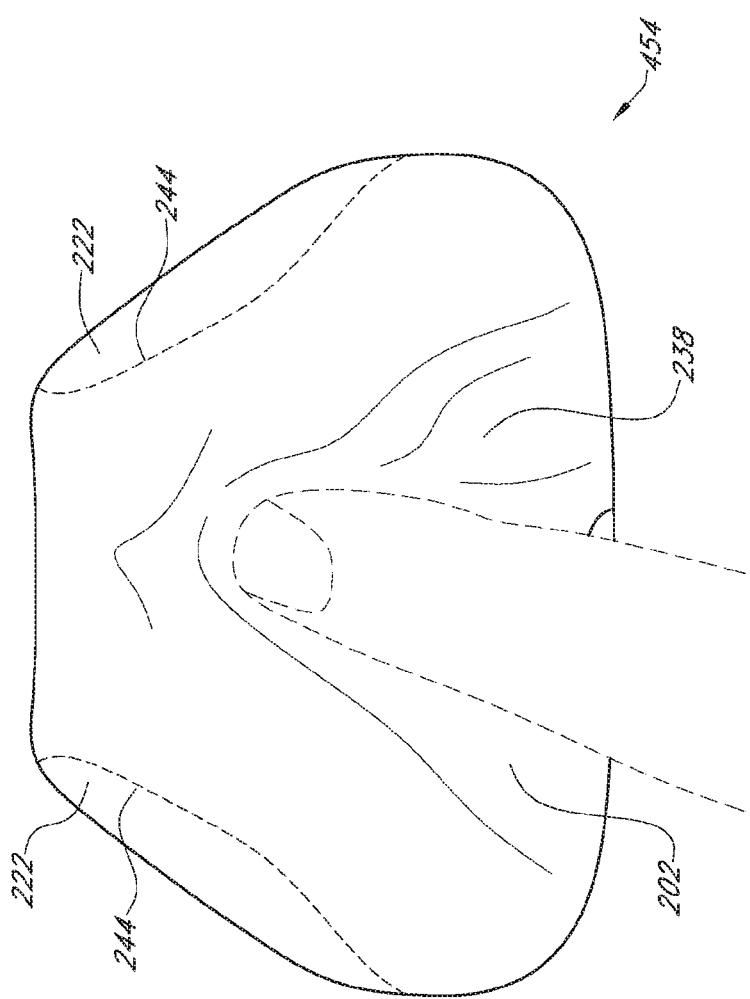
FIG. 11A is a rear view of the cushion of FIGS. 10A to 10F illustrating the cushion prior to a user's nose penetrating the breathable locating region.
Figure 11B:
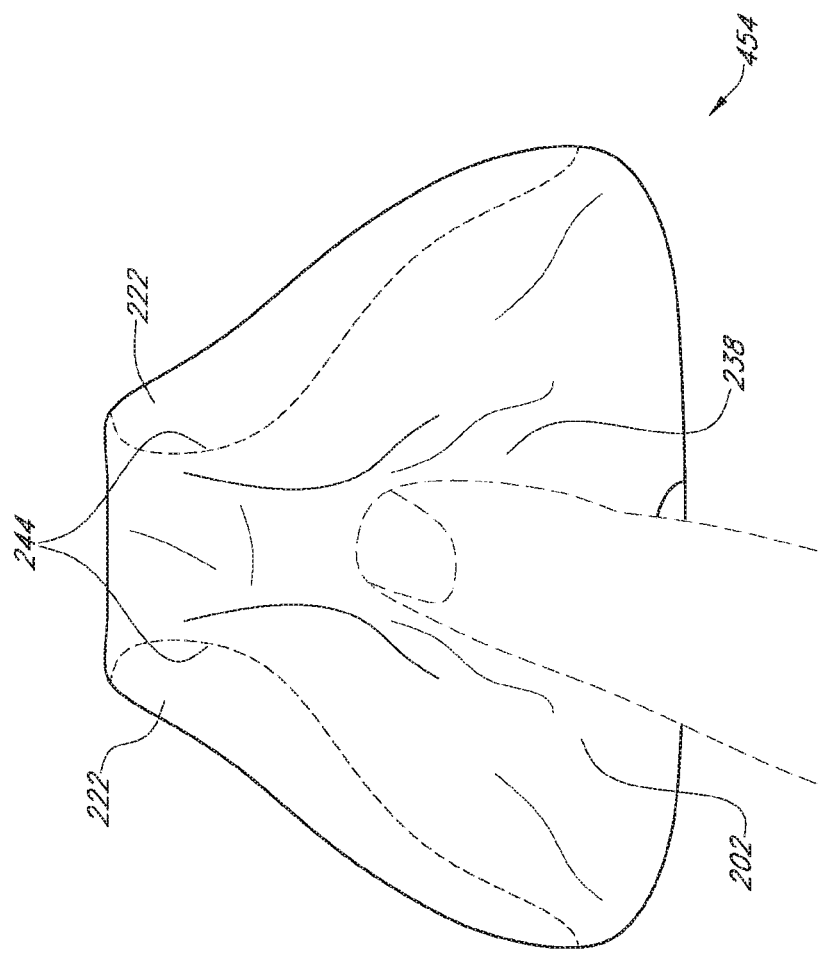
FIG. 11B is a rear view of the cushion of FIGS. 10A to 10F illustrating deformation of the cushion upon a user's nose penetrating a center portion of the breathable locating region.
Figure 11C:
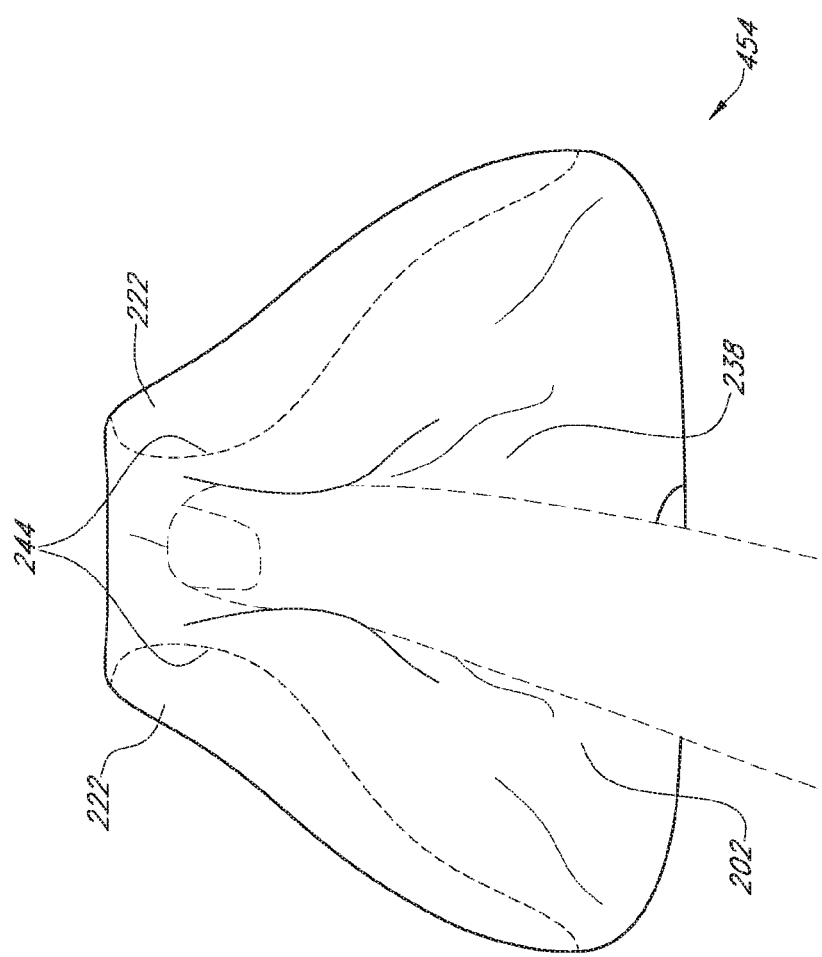
FIG. 11C is a rear view of the cushion of FIGS. 10A to 10F illustrating deformation of the cushion upon a user's nose penetrating an upper portion of the breathable locating region.

When donning the cushion 454, the user's nose is depressed against the breathable locating region 238 which is displaced toward the breathing chamber 130. As illustrated in FIG. 11A to 11C, the lack of an oro-nasal opening in the face contacting portion 202 encourages the upper corners 222 of the face contacting portion 202 to be pinched inwards towards the lateral sides of the user's nose when the user's nose is depressed against the breathable locating region 238. That is, as the user's nose protrudes into the face contacting portion 202, the stretchable textile material 318 is made taut and displaced into the breathing chamber 130 of the cushion 454. As a result of the stretchable textile material 318 being pushed into the breathing chamber 130 of the cushion 454, the stretchable textile material 318 pulls the upper corners 222 towards each other and into the breathing chamber 130. The upper corners 222 may deform and/or collapse radially inward as a result of being pulled towards each other. This results in the sealing region 244 of the face contacting portion 202 pinching the lateral sides of the user's nose and thus improving the seal between the cushion 454 and the user's face.

The breathable locating region 238 is configured to receive the user's nose and mouth. That is, the stretchable textile material 318 may be configured to stretch and conform to the shape of the user's nose. In some configurations, the breathable locating region 238 may have an amount of slack, sag or droop such that the breathable locating region 238 is loose and substantially without tension when the cushion 454 is not donned by the user. The slack reduces tension in the breathable locating region 238 which may decrease pressure against the user's nose. In some configurations, the stretchable textile material 318 may be formed with bellows or pleats that are shaped and configured to expand when the user's nose is depressed into the breathable locating region 238. In other configurations, the breathable locating region 238 may be formed from an elastic material such that the breathable locating region 238 stretches when the user's nose is depressed against the breathable locating region 238. In some embodiments, the stretchable textile material 318 may comprise a laminate material having at least one layer that is air tight in some regions, so as to increase the sealing region 244 that contacts the user's face and improve the sealability of the face contacting portion 202.

The cushion 414 is manufactured in an overmolding tool similar to the cushion 114. In some configurations, the stretchable textile material 318 of the face contacting portion 202 does not require thermoforming (as shown in FIG. 4A) and trimming (as shown in FIG. 4B) prior to being inserted in the overmolding tool 320. More specifically, the stretchable textile material 318 is a flexible sheet that is stretched over the first molding tool portion 322 of the overmolding tool 320 prior to being overmolded. In some configurations, a vacuum may be applied to the first and second thermoforming tool portions 302, 304 to maintain the stretchable textile material 318 in a stretched stated. Stretching the stretchable textile material 318 prior to overmolding allows the breathable locating region 238 to include an amount of slack, sag or droop such that the breathable locating region 238 is loose and substantially without tension when the cushion 454 is not donned by the user. Excess stretchable textile material 318 is trimmed at the seam 232, after the cushion 454 has been overmolded with silicone rubber 312. The overmolding tool 320 may include shut-off zones that define and limit how far into the stretchable textile material 318 the silicone rubber 312 can flow. The depths of penetration into the stretchable textile material 318 will define the shape of the sealing region 244.

Providing slack in the breathable locating region 238 reduces tension that may be applied to the tip of the user's nose when inserted into the cushion 414. If there was no slack, then the textile material 318 would have to stretch over the user's nose which may result in increased levels of tension being applied to the nose which may be uncomfortable.

Silicone Impregnated Textile Sealing Region with Silicone Stabilizing Layer

Figure 12A:
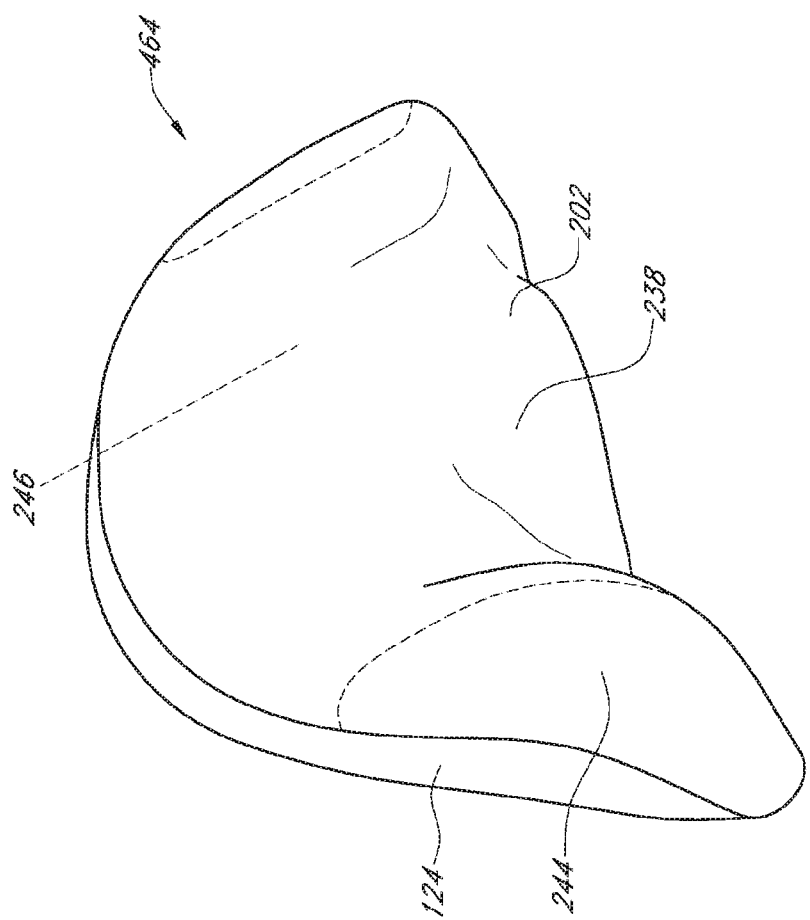
FIG. 12A is a perspective view of another alternative exemplary cushion having a breathable locating region formed from a continuous textile surface and a frame clip attached to a frame connection opening of the cushion.
Figure 12B:
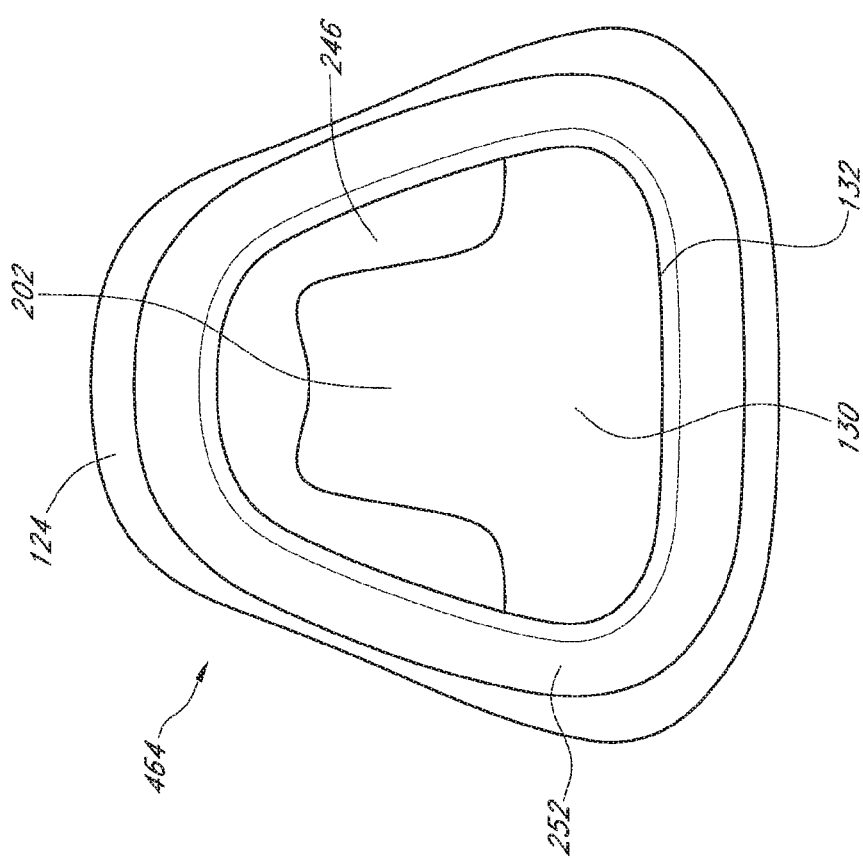
FIG. 12B is a front view of the cushion of FIG. 12A.
Figure 12C:
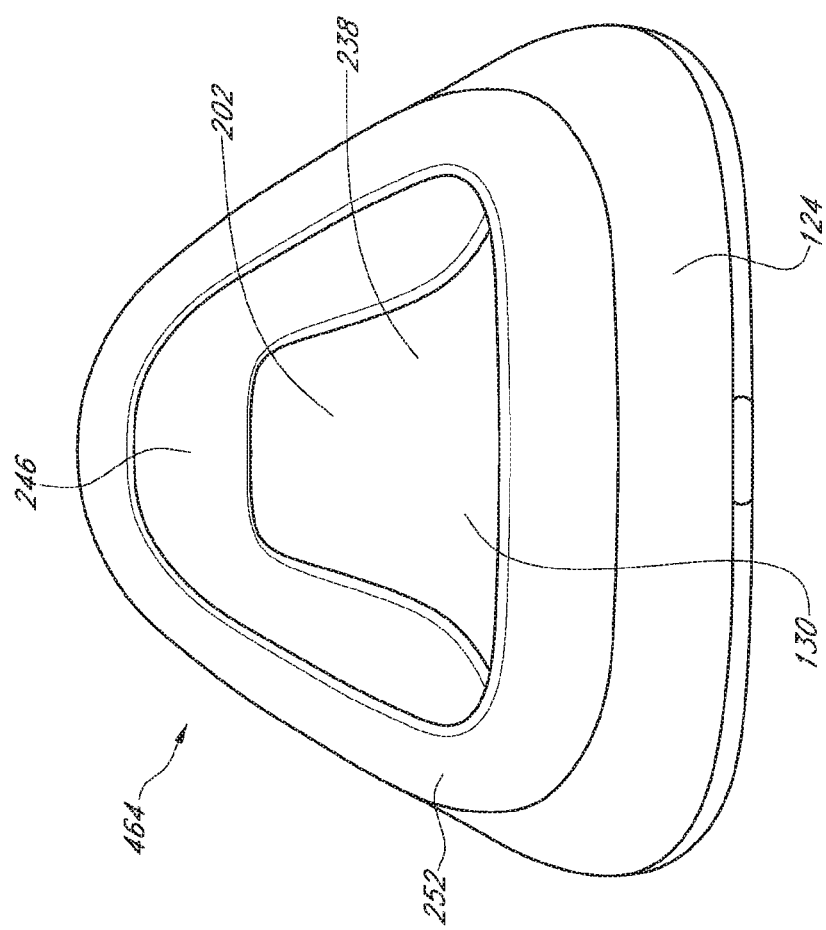
FIG. 12C is a view of the cushion of FIG. 12A showing the bottom and the front of the cushion.

FIGS. 12A to 12C illustrate an alternative configuration for a cushion 464 for use with the CPAP system 10 of FIG. 1. Description of certain similarities between the two configurations may be omitted herein for the sake of brevity and convenience, but such omission is not limiting. Similar to the cushion 454 of FIGS. 10A to 10F, the cushion 464 comprises a porous and air-permeable breathable locating region 238 through which the user receives pressurized gases from the breathing chamber 130. In contrast to the cushion 454, the cushion 464 includes a stabilizing layer 246 beneath the stretchable textile material 318 of the face contacting portion 202. That is, a stabilizing layer 246 is positioned between the breathing chamber 130 and the stretchable textile material 318 of the face contacting portion 202. The stabilizing layer 246 is positioned on an upper half of the face contacting portion 202, and is configured, in use, to apply a force to a patient's nose to stabilize the cushion on the patient's face.

As illustrated, the stabilizing layer 246 has an inverted U-shape that is configured to provide support to the stretchable textile material 318 of the face contacting portion 202 around the user's nasal bridge and cheek regions. That is, the stabilizing layer 246 may have a contoured arch shape that extends between a cheek region of the cushion 464, on each lateral side of the cushion 464 and over a nasal bridge region of the face contacting portion 202. The stabilizing layer 246 increases the stability of the cushion 464 on a user's face and prevents the housing 124 from digging into the user's nasal bridge as a result of the face contacting portion 202 collapsing due to over-tightening of the mask during fitting. Accordingly, the stabilizing layer 246 improves the sealability of the face contacting portion 202.

The stabilizing layer 246 is formed from silicone rubber 312 and may be formed independently or integrally with the non-face contacting portion 204. The stabilizing layer 246 is separate from and/or not attached to the stretchable textile material 318. The stabilizing layer 246 has an outer edge that is attached to an inner perimeter of the sealing region 244, and an inner edge that extends into the breathing chamber 130. That is, the stabilizing layer 246 may have a first end fixed to the sealing region 244 and second end that is free. The stabilizing layer 246 comprises a three-dimensional layer of silicone rubber that is positioned underneath the stretchable textile material 318 of the face contacting portion 202. The stabilizing layer 246 may have a thickness that is thicker, thinner or equal to the thickness of the non-face contacting portion 204. In some configurations, the stabilising layer 246 may replace or be in addition to the impregnated region 234 of the sealing region 244. In other configurations, a stabilising layer may be provided in other regions of the cushion, such as but not limited to a chin region or upper lip region (for a nasal interface). In some configurations, the stabilizing layer 246 may comprise multiple layers that are, in use, each positioned on respective sides of the user's nose. In some configurations, the stabilizing layer 246 may, in use, be positioned on respective sides of the user's nose but does not extend across the user's nasal bridge portion.

FIGS. 9B, 11B and 11C illustrate a frame clip 252 attached to the housing 124 of the cushion 444, 464. The frame clip 252 is a rigid ring formed from plastic that is permanently attached to the frame connection opening 132 of the housing 124. The frame clip 252 provides a detachable connection between the mask frame and the cushion. The frame clip 252 can comprise an inner portion 254 and an outer portion 256, that are permanently joined to each other by a snap-fit, friction-fit, welded joint or the like. The frame clip 252 provides a more reliable connection to the frame than connecting the silicone housing directly to the frame. That is, the increased rigidity of the frame clip 252 decreases a likelihood of leakage between the cushion 444, 464 and the conduit 120 due to bending or deformation of the cushion 444, 464.

Partially Impregnable Textile Material

Figure 13A:
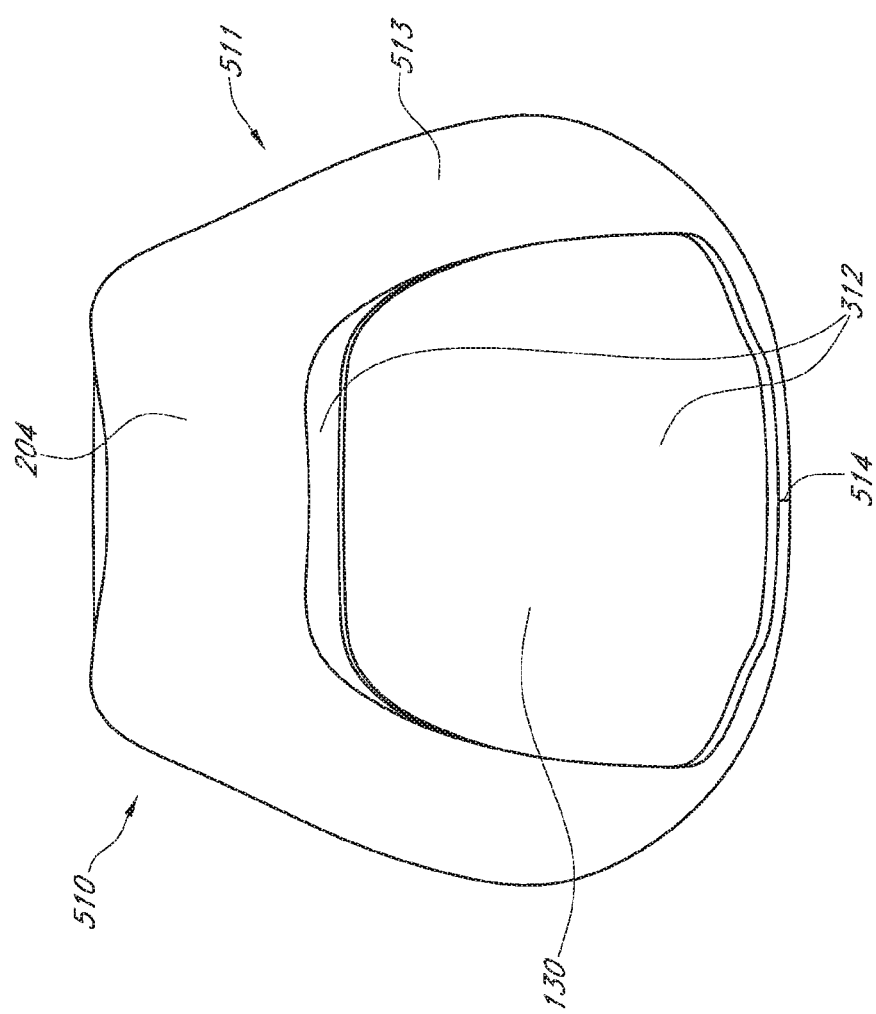
FIG. 13A is a front view of an alternative exemplary cushion having a non-stretch textile located about a non-face contacting portion of the cushion.
Figure 13B:
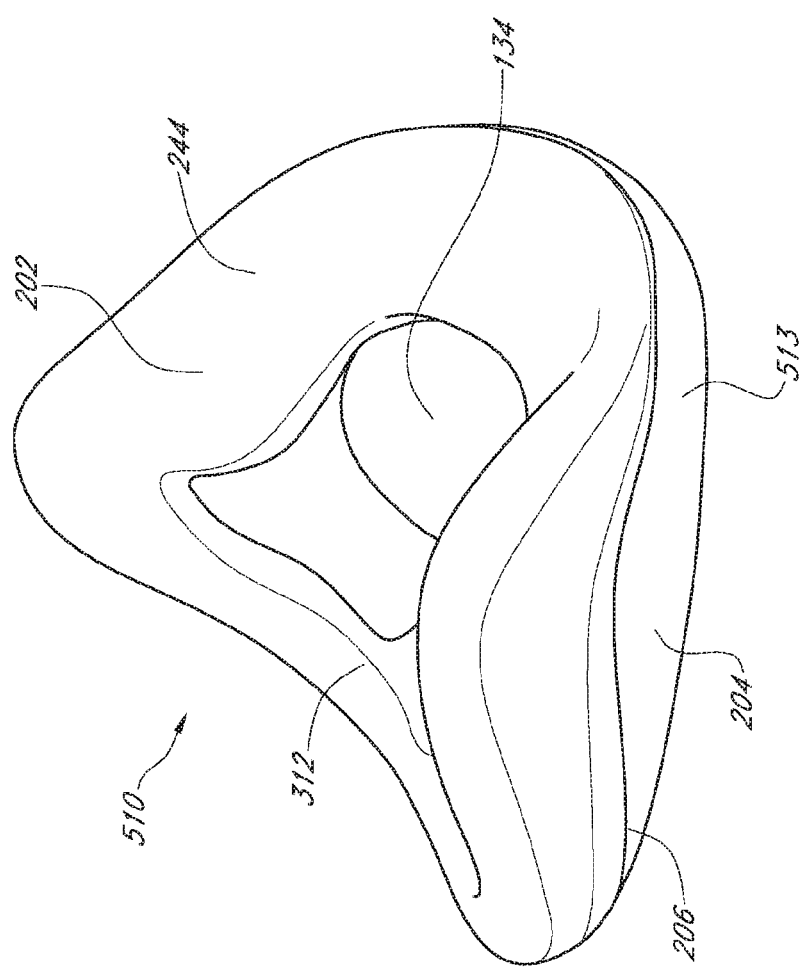
FIG. 13B is a rear perspective view of the cushion of FIG. 13A showing a face contacting portion and an oro-nasal opening of the cushion.
Figure 13C:
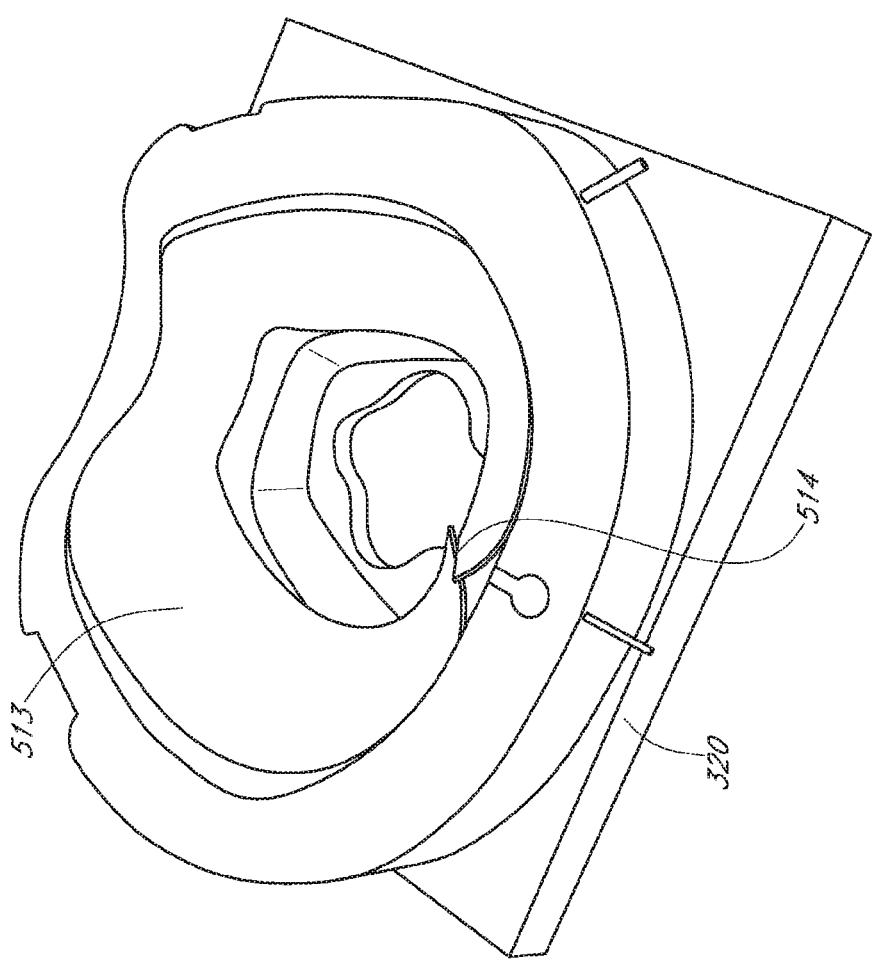
FIG. 13C is a perspective view of the exemplary overmolding tool during a step in the forming process of the cushion of FIGS. 13A and 13B.

FIGS. 13A to 13C illustrate an exemplary configuration of a cushion 510 for use with the CPAP system 10 of FIG. 1. The cushion 510 comprises a face contacting portion 202 and a non-face contacting portion 204. The non-face contacting portion 204 forms a forward facing or relatively distal portion of the partially enclosed breathing chamber 130, as described above. The face contacting portion 202 forms a rearward facing or relatively proximal portion of the breathing chamber 130 and is configured to engage with and form a substantially airtight seal against a user's face. An intermediate region 206 interconnects the face contacting portion 202 and the non-face contacting portion 204 along their respective edges.

The face contacting portion 202 contacts the face of the user to provide a seal that substantially encloses the nose and mouth of the user. That is, the face contacting portion 202 is configured to engage and form a substantially airtight seal with a user's face. The face contacting portion 202 has an oro-nasal opening 134 which receives the nose and mouth of the user. Pressurized gases supplied by the conduit 120 enters the breathing chamber 130 and are received by the user through the oro-nasal opening 134.

The face contacting portion 202 may comprise a sealing region 244. As illustrated, both the face contacting portion 202 and the sealing region 244 may be formed from an elastomeric material such as silicone rubber 312 which provides a smooth and continuous surface that engages the user's face to form an airtight seal about the nose and mouth of the user (i.e., an airtight seal around the oro-nasal opening 134). The non-face contacting portion 204 may also be formed of silicone rubber 312. Silicone rubber 312 may be positioned continuously around the face contacting portion 202 or at various regions on the face contacting portion 202 to provide user comfort, sealability, flexibility, etc. In other embodiments, the face contacting portion 202 and non-face contacting portion 204 may be formed from or include different materials, such as TPE materials.

The non-face contacting portion 204 may have a dual-layer construction that comprises a bottom or inner layer and a top or outer layer. The bottom layer may be formed of the same silicone rubber 312 or elastomeric material as the face contacting portion 202. The top layer may be formed of a textile, such as a non-stretch textile 513, although the top layer may be formed of a stretchable textile in some configurations. In other configurations, the top layer may be formed of a textile 513 having a blend of two or more fibers. In such configurations, the textile 513 may comprise a blend of between about 70-90% Nylon and 10-30% polyester woven microfiber. For example, the textile may comprise a blend having about 70% Nylon and about 30% polyester woven microfiber, or about 80% Nylon and about 20% polyester woven microfiber, or about 90% Nylon and about 10% polyester woven microfiber, although other percentage compositions and other suitable textile materials may be used. A suitable non-stretch textile 513 or stretch textile 513 will tolerate (i.e., not melt under) the high temperatures of the tooling used during the curing process of liquid silicone rubber 312. The non-stretch textile 513 may be positioned continuously around the non-face contacting portion 204, such that the non-face contacting portion 204 is substantially covered by the non-stretch textile 513. As illustrated in FIG. 13A, in some configurations, the non-stretch microfiber textile 513 may be positioned a spaced distance from the edge of the oro-nasal opening 134. Accordingly, a portion of the bottom layer of the non-face contacting portion 204 may be exposed between the non-stretch microfiber textile 513 and the oro-nasal opening 134.

The non-stretch textile 513 comprises a textile formed of high-density fibers, such as a non-stretch microfiber textile 513. Microfiber textiles such as the non-stretch microfiber textile 513 generally have a fiber diameter that is less than 1 denier (i.e., less than about 10 micrometer). During manufacturing of the cushion 510, the non-stretch textile 513 is placed in a cavity of the overmolding tool 320 and liquid silicone rubber 312 is injected into the overmolding tool 320 to join the non-stretch textile 513 with a portion of the injected silicone rubber 312 and form the non-face contacting portion 204 of the cushion 510. The liquid silicone rubber 312 is partially driven into the fiber structure on the user-facing side or inside of the non-stretch textile 513. In contrast to the fully impregnated textile material of FIGS. 6A to 6F, the high-density fiber structure of the non-stretch textile 513 is at least partially impregnable to the flow of the liquid silicone rubber 312. Instead, during attachment of the non-stretch textile 513 to the bottom layer of the non-face contacting portion 204, silicone rubber 312 can penetrate only a portion of the thickness of the user-facing side of the non-stretch textile 513. Accordingly, the non-stretch textile 513 is secured to the bottom layer of the non-face contacting portion 204 but forms a textile forward facing surface 511 that is not saturated by the silicone rubber 312 on the exposed side of the non-stretch textile 513. In some configurations, materials other than non-stretch microfiber textile 513 may be used to form the textile forward facing surface 511, such as the such as the Breath-o-prene® material described above. In further configurations, Breath-o-prene® material forms all or part of the non-face contacting portion 204.

As described above, the non-face contacting portion 204 of the cushion 510 comprises the textile forward facing surface 511 that retains the texture, appearance, and other characteristics of the non-stretch textile 513. The non-face contacting portion 204 is often the most visible or apparent aspect of the cushion 511 when it is donned by the user. Advantageously, including the textile forward facing surface 511 that retains the soft touch of the non-stretch textile 513 while providing a textile aesthetic that is more comforting and visually appealing in a bedroom environment. In some configurations, the non-stretch textile 513 may also have a contrasting colour relative to the silicone rubber 312 which provides an aesthetically pleasing appearance. The contrasting colour may also provide visual indication to the user regarding locatability and fitment of the cushion 510 on the user's face. This contrasting colour may also provide visual assembly indicators or cues for assembling the cushion 510 with other components of the CPAP mask system 10. The textile forward facing surface 511 also protects the underlying silicone rubber structure of the cushion 510 from abrasion and wear caused by the user's hand when donning or doffing the cushion 510.

The continuous curvature of the non-face contacting portion 204 and the non-stretch nature of the non-stretch textile 513 increase the difficulty of securing the non-stretch textile 513 to the non-face contacting portion 204 while obtaining the smooth (e.g., wrinkle-free) surface finish illustrated in FIG. 13A. As illustrated in FIG. 13C, the non-stretch textile 513 may include one or more splits 514 that allow the substantially two-dimensional non-stretch textile 513 to conform to the three-dimensional geometry of the overmolding tool 320 and ultimately, the cushion 510. Each split 514 provides additional degrees of freedom that enable the non-stretch textile 513 to more closely conform to the three-dimensional geometry of the cushion 510. Each of the one or more splits 514 may extend from an outer periphery of the non-stretch textile 513 to an inner periphery of the non-stretch textile 513. Accordingly, the split 514 may extend from the outer periphery of the non-stretch textile 513 to the outer perimeter of the oro-nasal opening 134. In some configurations, the split 514 may not extend the entirety of the distance between the outer and inner periphery of the non-stretch textile 513. In further configurations, the non-stretch textile 513 may include a split 514 that is positioned on the bottom of the cushion 510 (e.g., near the chin region of the user) to provide a cleaner aesthetic to the portions of the cushion 510 that are visible to the user in use.

Textile and Silicone Impregnated Join

Figure 14A:
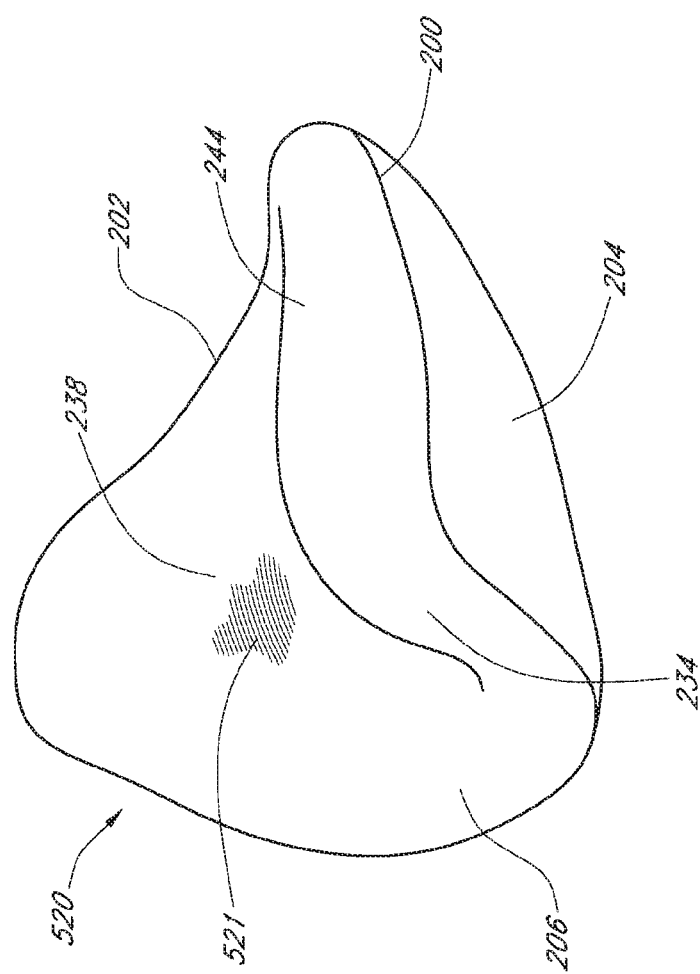
FIG. 14A is a rear perspective view of an alternative exemplary cushion having a face contacting portion with a breathable locating region constructed of a three-dimensional knitted textile material.
Figure 14B:
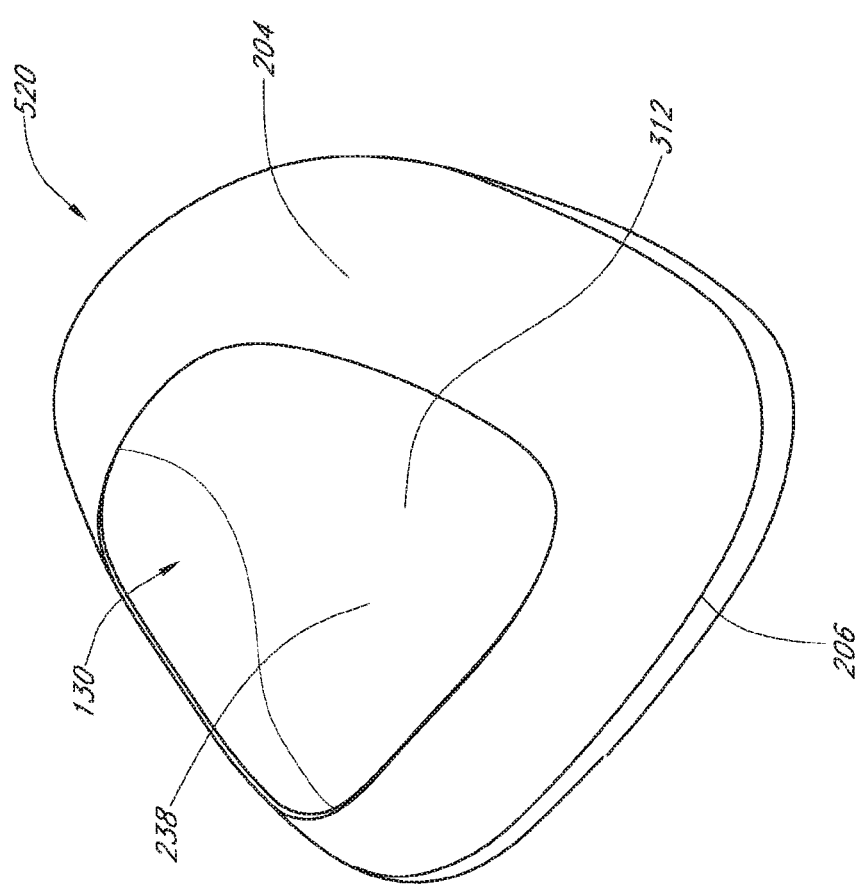
FIG. 14B is a front perspective view of the cushion of FIG. 14A showing a non-face contacting portion of the cushion.

FIGS. 14A and 14B illustrate a configuration for a cushion 520 for use with the CPAP system 10 of FIG. 1. Similar to the cushion 454 of FIGS. 10A to 10F, the cushion 520 comprises a user face contacting portion 202 and a non-face contacting portion 204. The face contacting portion 202 of the cushion 520 does not include an oro-nasal opening 134 but instead comprises a continuous and uninterrupted three-dimensional knitted textile material 521 to receive the user's nose and/or mouth. The face contacting portion 202 comprises a breathable locating region 238 and a sealing region 244. The breathable locating region 238 is porous and air permeable such that pressurized gases within the breathing chamber 130 are received by the user through the stretchable textile material 521. The breathable locating region 238 is centrally located on the face contact portion 202 to engage with and/or cover the nose and/or mouth of the user. In some configurations, the sealing region 244 is formed from a composite material such as a silicone rubber 312 that is impregnated within the three-dimensional knitted textile material 521 to provide a comfortable surface against the user's face and a substantially airtight seal. In other configurations, the sealing region 244 is formed of silicone rubber 312 alone. The sealing region 244 extends about a portion or an entirety of the perimeter of the breathable locating region 238. That is, the sealing region 244 is positioned radially outward of the breathable locating region 238 relative to the centroid of the cushion 520. In other words, the sealing region 244 partially or completely surrounds the breathable locating region 238.

Similar to the cushion 454 of FIGS. 10A to 10F, the non-face contacting portion 204 is formed along an outer perimeter of the face contacting portion 202 along the intermediate region 206 by an overmolding process. That is, the cushion 520 includes an impregnated region 234 where the three-dimensional knitted textile material 521 is impregnated with silicone rubber 312 within a portion or an entirety of the non-face contacting portion 204 and along an outer perimeter of the intermediate region 206 and/or the face contacting portion 202. Accordingly, the three-dimensional knitted textile material 521 and the impregnated region 234 extend only partly onto (i.e., does not completely cover) the non-face contacting portion 204. The non-impregnated breathable locating region 238 of the three-dimensional knitted textile material 521 is positioned radially inward of the impregnated region 234. That is, at least part of an outer perimeter of the face contacting portion 202 is impregnated with silicone rubber 312 and at least part of an interior region of the face contacting portion 202 is not impregnated with silicone rubber 312. In some configurations, the outer perimeter of the breathable locating region 238 defines the inner perimeter of the impregnated region 234.

In contrast to the cushion 454 of FIGS. 10A to 10F, the face contacting portion 202 of the cushion 520 comprises a three-dimensional knitted textile material 521 rather than a substantially two-dimensional sheet of stretchable textile material 318. A two-dimensional sheet of stretchable textile material 318 may be limited to having a predetermined three-dimensional contour that is determined by the geometry of the sealing region 244 when not in use. In some configurations, the three-dimensional knitted textile material 521 comprises such a three-dimensional contour that substantially matches the seal geometry. Advantageously, in other configurations, the three-dimensional knit of the three-dimensional knitted textile material 521 allows the three-dimensional knitted textile material 521 to comprise a shape, contour, or form that is independent of the geometry of the sealing region 244. Accordingly, in some configurations, the three-dimensional knitted textile material 521 may comprise a sock, a dome, an enclosed tube, or various concave three-dimensional geometries. In further configurations, the three-dimensional knitted textile material 521 may be customized to accommodate the specific facial features of a particular user to enhance the comfort and sealability of the cushion 520.

When donning the cushion 520, the user's nose is depressed against the breathable locating region 238 which is displaced toward the breathing chamber 130. The breathable locating region 238 is configured to receive the user's nose and mouth. That is, the three-dimensional knitted textile material 521 may be configured to stretch and conform to the shape of the user's nose. In some configurations, the grain direction of the three-dimensional knitted textile material 521 is tailored to create both high-stretch and low-stretch regions throughout the three-dimensional knitted textile material 521 of the face contacting portion 202. In further configurations, a high-stretch region may be positioned near the center of the breathable locating region 238 to provide increased adaptability for users having differently sized noses. In such configurations, the centrally located high-stretch region improves user comfort by reducing the pressure of the breathable locating region 238 on the user's nose. Advantageously, the superior adaptability (e.g., textile shape independent of the sealing geometry, high- and low-stretch regions) offered by the three-dimensional knitted textile material 521 allows the three-dimensional knitted textile material 521 to readily conform from the face contacting portion 202, around the outer perimeter of the cushion 520, and onto part of the non-face contacting portion 204. Accordingly, the three-dimensional knitted textile material 521 helps to minimize wrinkles (i.e., caused by excess material) in the textile that would otherwise occur on the outer perimeter or part of the non-face contacting portion 204 as a result of the overmolding process.

FIGS. 15A to 15D illustrate an alternative configuration for a cushion 520 for use with the CPAP system 10 of FIG. 1. Description of certain similarities between the two configurations may be omitted herein for the sake of brevity and convenience, but such omission is not limiting. Similar to the cushion 520 of FIGS. 14A and 14B, the cushion 520 comprises a user face contacting portion 202 and a non-face contacting portion 204 interconnected by an intermediate region 206. The face contacting portion 202 comprises a three-dimensional knitted textile material 521, a breathable locating region 238, a sealing region 244, and an outer perimeter, as described above. The non-face contacting portion 204 comprises an impregnated region 234.

Figure 15A:
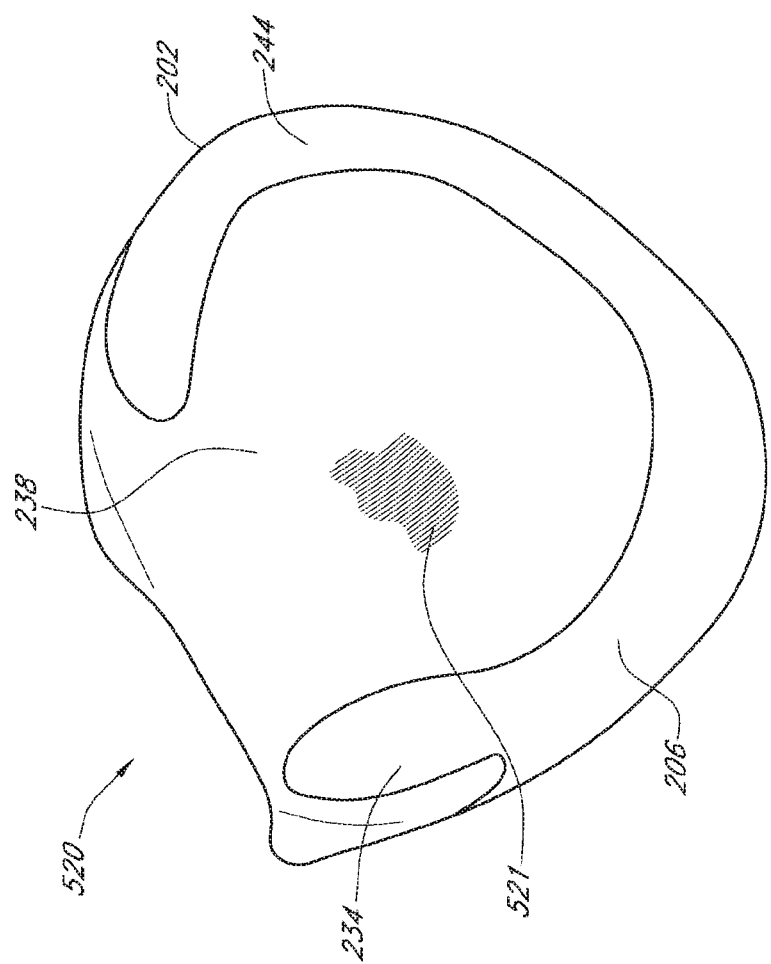
FIG. 15A is a rear perspective view of another alternative exemplary cushion having a face contacting portion with a breathable locating region constructed of a three-dimensional knitted textile material.
Figure 15B:
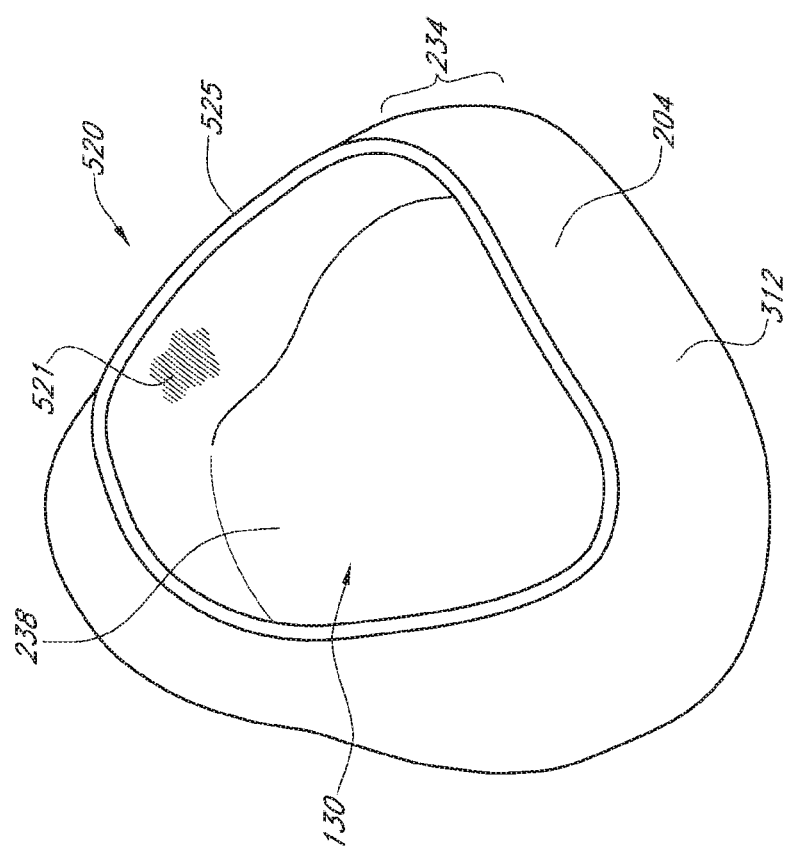
FIG. 15B is a front perspective view of the cushion of FIG. 15A showing a non-face contacting portion of the cushion in which the three-dimensional knitted textile material extends to an opening on the non-face contacting portion of the cushion.

In contrast to the cushion 520 of FIGS. 14A and 14B, in the present configuration the three-dimensional knitted material 521 extends from the face contacting portion 202 to the non-face contacting portion 204 and completely covers the non-face contacting portion 204 of the cushion 520, as illustrated in FIG. 15B. Correspondingly, in such a configuration, the impregnated region 234, in which the three-dimensional knitted textile material 521 is impregnated with silicone rubber 312, completely covers the non-face contacting portion 204. As shown in FIGS. 15B and 15D, the three-dimensional knitted textile material 521 extends from the face contacting portion 202 to the non-face contacting portion 204 to define the breathing chamber 130. The three-dimensional knitted textile material 521 of the non-face contacting portion 204 is overmolded with silicone rubber 312 such that the three-dimensional knitted textile material 521 of the non-face contacting portion 204 is fully impregnated by, and thus encased in, silicone rubber 312. Accordingly, the outermost and innermost layers of the non-face contacting portion are formed of silicone rubber 312 with the three-dimensional knitted textile material 521 embedded therein. The silicone rubber 312 of the present configuration is transparent, although some configurations may utilize semi-transparent or opaque silicone rubber 312. The non-face contacting portion 204 thus retains a textile appearance while providing a durable silicone rubber surface texture. In such an embodiment, the silicone rubber outer surface of the non-face contacting portion 204 provides a support structure and an airtight breathing chamber 130 that allows the supply of air to the user's airways to be pressurized. The impregnated region 234 may have a thickness that is thicker, thinner or equal to the thickness of the intermediate region 206 to allow the non-face contacting portion 204 to provide support to the face contacting portion 202. Accordingly, in the present configuration, the face-contacting portion 202 retains the comfort and adaptability of the breathable locating region 238 that is formed of the three-dimensional knitted textile material 521 while the non-face contacting portion 204 retains a textile aesthetic and provides a silicone rubber support structure for the cushion 520.

Figure 15C:
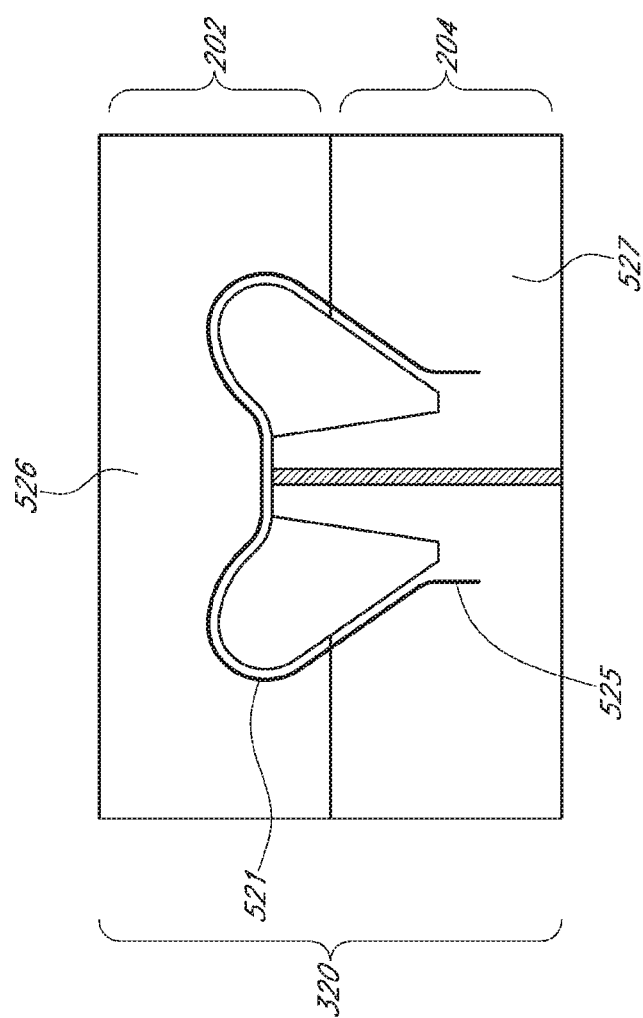
FIG. 15C is a cross-sectional view of an overmolding tool during a step in the forming process of the cushion of FIGS. 15A, 15B, and 15D.
Figure 15D:
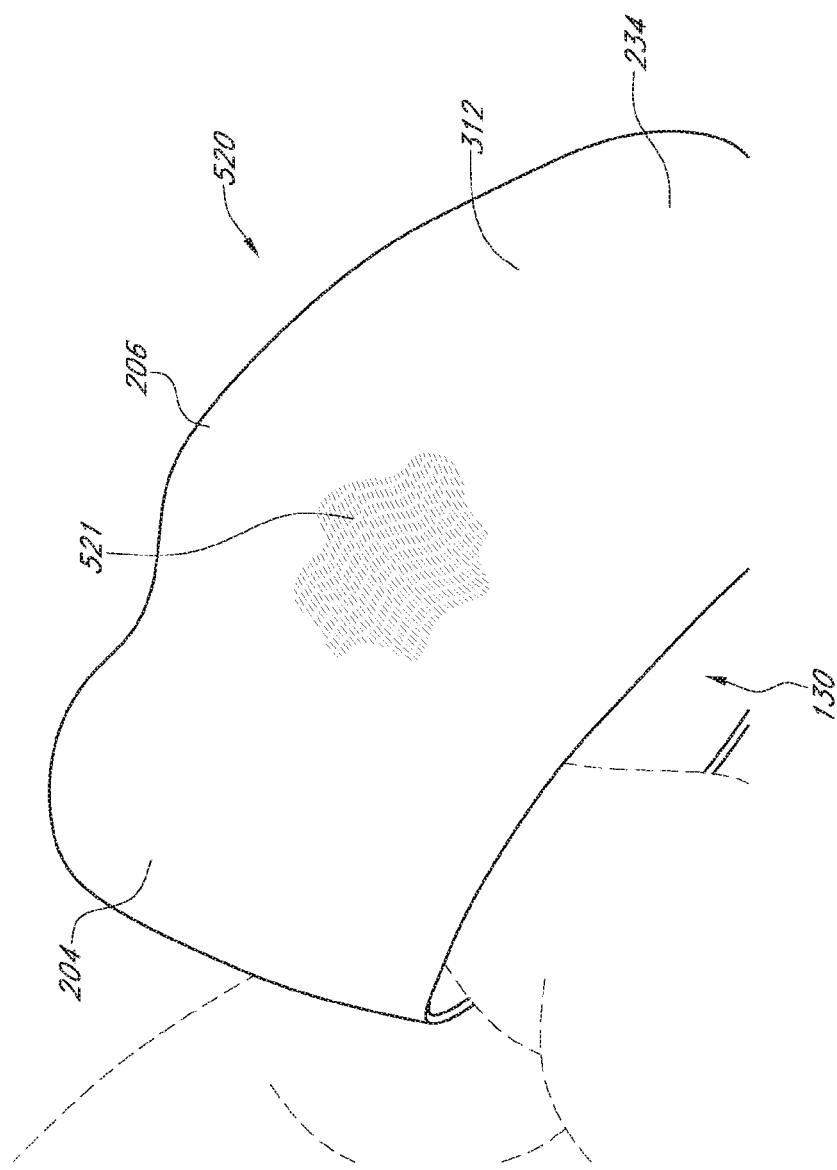
FIG. 15D a front perspective view of part of the non-face contacting portion of the cushion of FIGS. 15A and 15B.

In some configurations, the three-dimensional knitted textile material 521 extends at least slightly beyond the impregnated region 234 such that non-face contacting portion 204 includes an unsaturated, exposed periphery 525 of the three-dimensional knitted textile material 521 around the opening of to the breathing chamber 130, as illustrated in FIGS. 15B and 15C. This exposed periphery 525 of the three-dimensional knitted textile material 521 may be secured in place by the overmolding tool 320 to prevent the three-dimensional knitted textile material 521 from bunching up (e.g., wrinkling) during the overmolding process. After the overmolding process is complete, the exposed periphery 525 may be trimmed or otherwise removed. The cushion 520 also provides a textile appearance throughout that provides a softer aesthetic which may be comforting and desirable in a bedroom environment. Further, the lack of visible seams or joins on the cushion 520 provides a visually refined appearance that avoids rough edges which may be uncomfortable if brought into contact with the user's face.

FIG. 15C illustrates a cross-section of an alternative configuration of the overmolding tool 320 for forming the cushion 520 from the three-dimensional knitted textile material 521 and the liquid silicone rubber 312. That is, FIG. 15C illustrates the overmolding tool 320 and corresponding process for forming the face contacting portion 202 and non-face contacting portion 204 from the three-dimensional knitted textile material 521 and overmolding liquid silicone rubber 312 onto the sealing region 244, intermediate region 206, and non-face contacting portion 206. A sheet of the three-dimensional knitted textile material 521 is placed on a core 528 and retained by (e.g., clamped by) the first and second portions 526, 527 of the overmolding tool 320, which may be an open-shut style tool. The three-dimensional knitted textile material 521 conforms to the core 528 due to its three-dimensional knit and high- and low-stretch regions. The first tool portion 526 defines the face contacting portion 202 and a portion of the breathing chamber 130, and the second tool portion 527 defines the non-face contacting portion 204, an opening for the breathing chamber 130, and at least part of the breathing chamber 130. In some configurations, the second molding tool portion 527 secures the exposed periphery 525 of the three-dimensional knitted textile material 521 in place to prevent the textile from being bunched up during the molding process.

Once the three-dimensional knitted textile material 521 is secured within the overmolding tool 320, the liquid silicone rubber 312 is injected into overmolding tool 320, such as through the core 528 and into a space between the core 528 and the textile the three-dimensional knitted textile material 521. As such, the liquid silicone rubber 312 is injected into the interior surface of the three-dimensional knitted textile material 521. During the injection of liquid silicone rubber 312 into the overmolding tool 320, the sealing region 244, the intermediate portion 206, and the impregnated region 234 of the three-dimensional knitted textile material 521 are impregnated with liquid silicone rubber 312 to arrive at the cushion 520 illustrated in FIGS. 15A, 15B, and 15D. That is, liquid silicone rubber 312 may be allowed to permeate specific regions of the three-dimensional knitted textile material 521 to improve the seal of the face contacting portion 202 with the user's face while also being restricted or inhibited from permeating the area defining the breathable locating region 238. In some configurations, the location region 238 is clamped between the core 528 and the first tool portion 526 to prevent silicone rubber 312 from flowing into the three-dimensional knitted textile material 521. In some configurations, another suitable thermoplastic elastomer (e.g., TPE) may be injected into the overmolding tool in place of liquid silicone rubber 312. TPE increases in density as it cools, and in some configurations, this density increasing aspect of TPE can inhibit or prevent the elastomer from fully impregnating the three-dimensional knitted textile material 521. As described above, partially impregnated textile material is an advantageous construction as it retains the feel, appearance, and other aspects of the textile that may be lost when the textile is fully saturated with liquid silicone rubber 312.

Textile-to-Textile Join

Figure 16B:
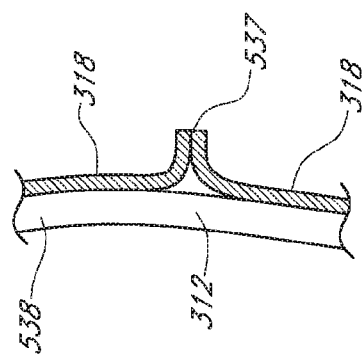
FIG. 16B is a cross-sectional view of a part of the cushion of FIG. 16C.
Figure 16C:
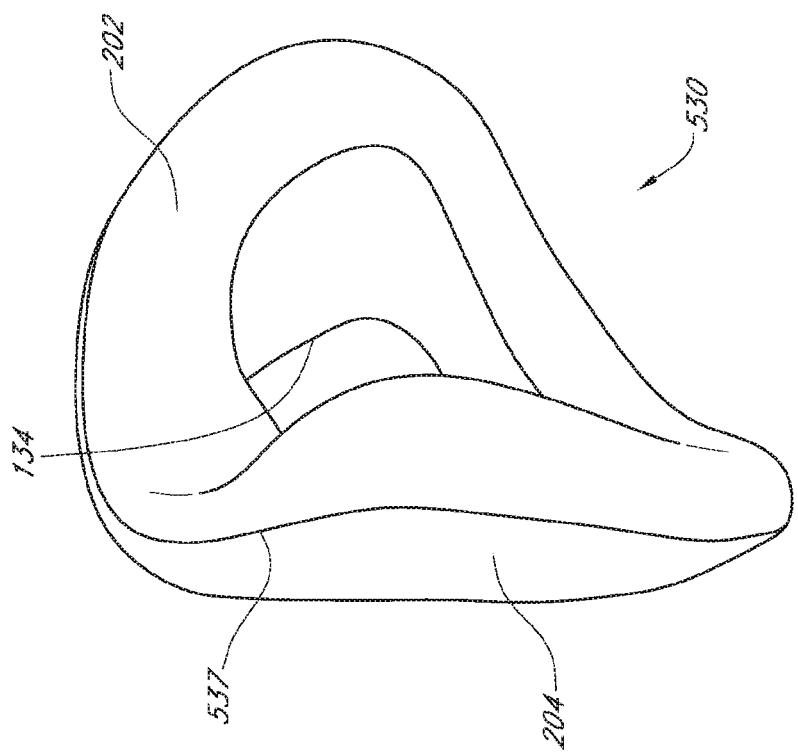
FIG. 16C is a rear perspective view of an alternative exemplary cushion having a textile face contacting portion and a textile non-face contacting portion.

FIGS. 16A to 16C illustrate the steps for forming a cushion 530 that comprises a face contacting portion 202 with a textile outer surface and a non-face contacting portion 204 with a textile outer surface. As shown in FIG. 16A, a first sheet of stretchable textile material 318 is placed between the first portion 535 and the core 534 of the overmolding tool 533. A second sheet of stretchable textile material 318 is placed between the core 534 and the second portion 536 of the overmolding tool 533. The core 534 defines the breathing chamber 130 of the cushion 530. In some configurations, one or both sheets of the stretchable textile material 318 may be in the form of a laminate containing one or more textile sheet layers. In some configurations, the stretchable textile material 318 may comprise three-dimensional knitted textile material 521 like the cushion 520. In other configurations, the stretchable textile material 318 may have a preformed three-dimensional shape. The first portion 535 defines the face contacting portion 202 of the cushion 530 while the second portion 536 defines the non-face contacting portion 204. In some configurations, the face contacting portion 202 defines an oro-nasal opening 134, as shown in FIG. 16C. In other configurations, the face contacting portion 202 lacks an oro-nasal opening 134 but instead includes a breathable locating region 238 similar to the cushion 520 of FIGS. 14A and 14B FIGS. 15A to 15D.

The first and second sheets of stretchable textile material 318 are stretched (i.e., held in tension) as the first and second portions 535, 536 of the overmolding tool 533 are clamped together around the core 534. The clamping together of the first and second portions 535, 536 of the overmolding tool 533 against the core 534 clamps the first and second sheets of stretchable textile material 318 together at their respective edges to form a seam 537, as illustrated in FIG. 16B. Liquid silicone rubber 312 or TPE is injected into a space between the core 534 and the first and second sheets of stretchable textile material 318, such as through the core 534, which does not fully permeate to the outer surface of the stretchable textile material 318 but impregnates the breathing chamber side of the stretchable textile material 318 with an elastomeric layer 538 that extends continuously between the face and non-face contacting portions 202, 204 and joins the first and second sheets of stretchable textile material 318 together at the seam 537. In some configurations, TPE is injected into the overmolding tool 533 to improve control over the manufacturing process of the cushion 520 by decreasing the likelihood of fully impregnating the stretchable textile material 318. Any excess stretchable textile material 318 at the seam 537 is trimmed or removed from the cushion 530 after the overmolding process to obtain the clean seam illustrated in FIG. 16C.

Similar to the molding process described with reference to FIG. 4, the amount of silicone impregnation into the stretchable textile material 318 may vary according to the injection pressure of the liquid silicone rubber 312, the duration of the injection, the thickness of the face contacting portion 202 relative to the thickness of the non-face contacting portion 204, the density of the stretchable textile material 318, etc. Accordingly, the elastomeric layer 538 can extend from any portion of non-face contacting portion 204 to the oro-nasal opening 134 on the face contacting portion 202. In some configurations where the cushion 530 lacks an oro-nasal opening 134, the elastomeric layer 538 can extend to a periphery of the face contacting portion 202 that defines the breathable locating region 238.

Figure 17A:
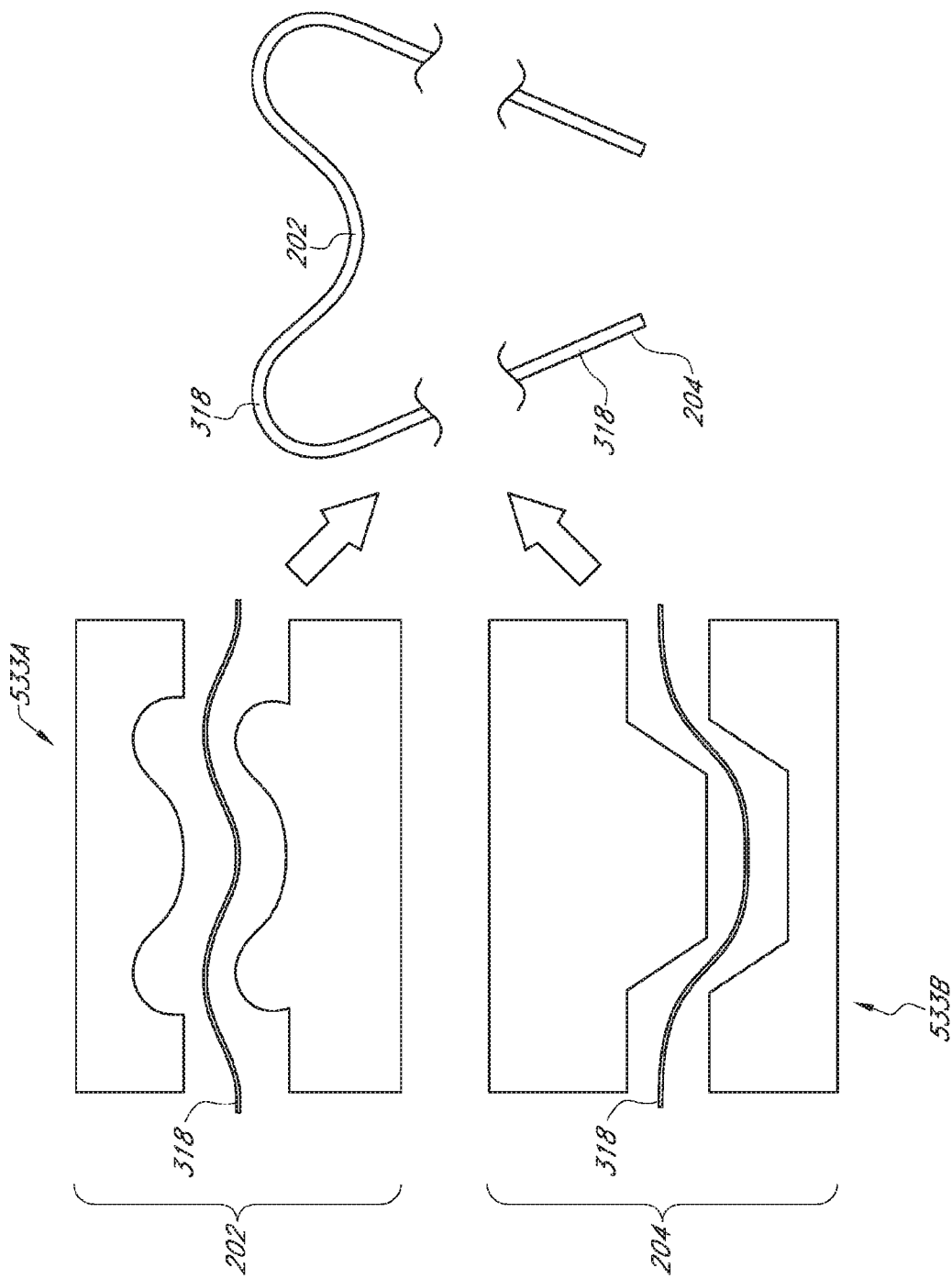
FIG. 17A is a cross-sectional view of a forming tool during a step in the forming process of the cushion of FIGS. 17B and 17C.
Figure 17B:
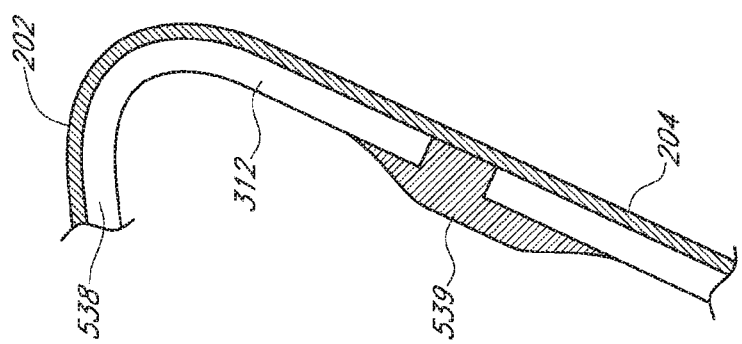
FIG. 17B is a cross-sectional view of a part of the cushion of FIG. 17C.
Figure 17C:
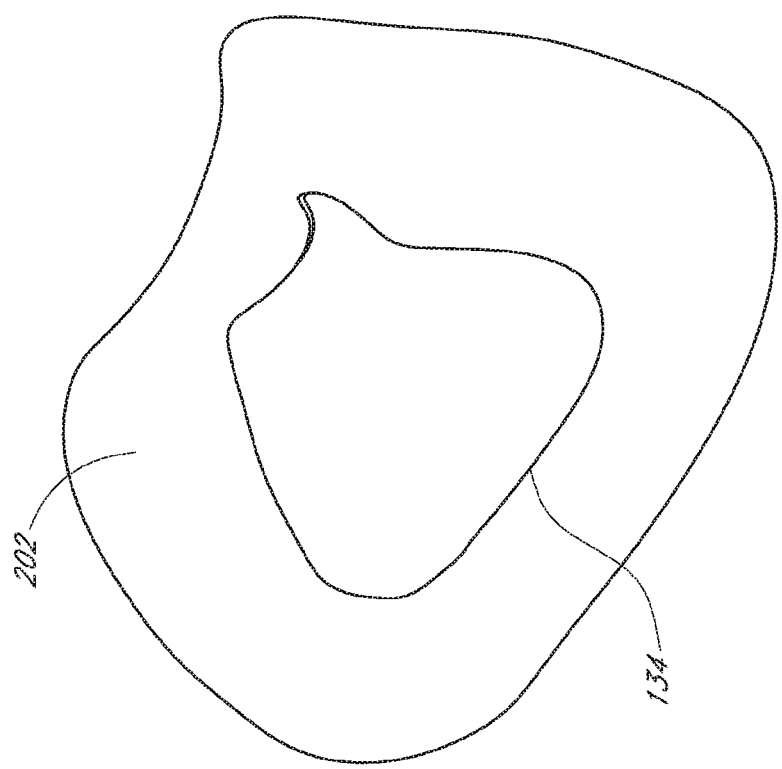
FIG. 17C is a rear perspective view of another alternative exemplary cushion having a textile face contacting portion and a textile non-face contacting portion

FIGS. 17A to 17C illustrate the steps for forming an alternative configuration of a cushion 530. Description of certain similarities between the two processes may be omitted herein for the sake of brevity and convenience, but such omission is not limiting. Similar to the cushion 530 of FIGS. 16A to 16C, the cushion 530 of the present embodiment comprises a face contacting portion 202 with a textile outer surface and a non-face contacting portion 204 with a textile outer surface that is formed in an overmolding process in which liquid silicone rubber 312 or other suitable elastomeric material is injected into a tool. As described above, the flow of liquid silicone rubber 312 or other elastomer is more readily controlled during the overmolding process when the textile material covers a smaller portion of the cushion 530.

As shown in FIG. 17A, a first sheet of stretchable textile material 318 is placed between the first and second portions of a first forming tool 533A. A second sheet of stretchable textile material 318 is placed between the first and second portions of a second forming tool 533B. The portions of the first forming tool 533A are pressed or clamped together and the liquid silicone rubber 312 or other suitable elastomeric material is injected to form the first sheet of stretchable textile material 318 into the face contacting portion 202. The portions of the second forming tool 533B are pressed or clamped together and the liquid silicone rubber 312 or other suitable elastomeric material injected to form the second sheet of stretchable textile material 318 into the non-face contacting portion 204. As illustrated in FIG. 17B, the overmolding process impregnates preferably the interior side of each sheet of stretchable textile material 318 as desired with an elastomeric layer 538. In a further step, the face contacting portion 202 and the non-face contacting portion 204 are aligned such that the edges of the portions 202, 204 abut one another in a flush manner, as illustrated in FIG. 17B. Bonding material 539 is then applied to the interior side of the face and non-face contacting portions 202, 204 to interconnect the portions 202, 204, thereby forming the cushion 530 as illustrated in FIG. 17C. The bonding material 539 may be liquid silicone rubber 312, another suitable elastomeric material or any suitable bonding agent and may be applied by any suitable process.

In some configurations, the face contacting portion 202 and non-face contacting portion 204 are connected to one another by an overmolding process after being removed from the respective tools 533A, 533B. During the overmolding process, the face contacting portion 202 and non-face contacting portion 204 are aligned such that the edges of the portions 202, 204 abut one another in a flush manner within an overmolding tool and silicone rubber 312 or other elastomer is then introduced to at least the interior side of at least regions of the face and non-face contacting portions 202, 204 adjacent the joining edges to interconnect the portions 202, 204 and form the cushion 530.

The processes described above achieve a cushion 530 that retains a textile feel and appearance on an outer surface of the face contacting portion 202 and the non-face contacting portion 204, thereby providing a softer aesthetic that may be comforting and desirable in a bedroom environment. In addition, the smaller the textile component, the easier it is to control the flow of liquid silicone rubber 312 or other elastomer during the overmolding process. In this respect, the process illustrated in FIGS. 16A to 16C is advantageous because it involves the overmolding of two textile components (e.g., the face and non-face contacting portions 202, 204) instead of a single, larger textile component. The process illustrated in FIGS. 17A to 17C is further advantageous in this respect because it involves separately overmolding the face and non-face contacting portions which allows greater control over the flow of the liquid silicone rubber 312 or other elastomer. The process of FIGS. 17A to 17C also provides a smooth external joint between the portions 202, 204 that may be less noticeable, more visually appealing, and more comfortable to the user due to the lack of abrupt or rough edges at the joint. In some configurations, the cushion 530 may comprise a face contacting portion 202 and a non-face contacting portion formed of different textile materials. Accordingly, the face contacting portion 202 may comprise a color, material, and/or surface finish that is different from that of the non-face contacting portion 204. In other configurations, stretchable or non-stretch textile materials 318 may be used to form either of the portions 202, 204. In configurations comprising a breathable locating region 238, the face contacting portion 202 may comprise the three-dimensional knitted textile material 521 described above.

Textile Cover

Figure 18A:
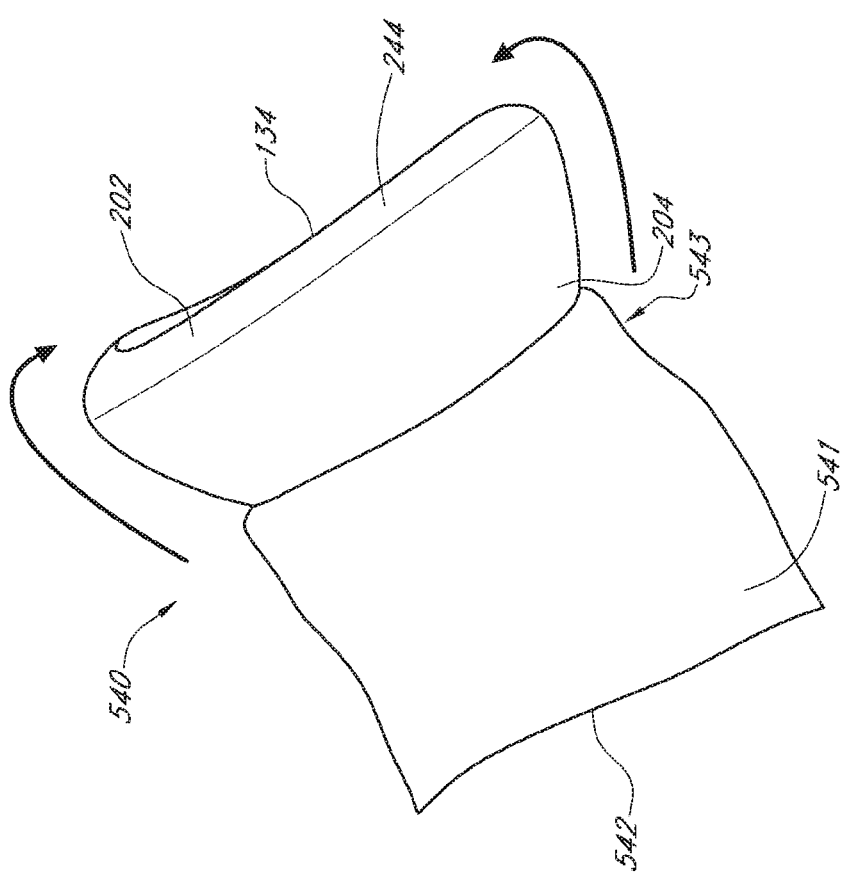
FIG. 18A is a side view of an alternative exemplary cushion having a face contacting portion, a non-face contacting portion, and a textile cover in an uncovered state.
Figure 18B:
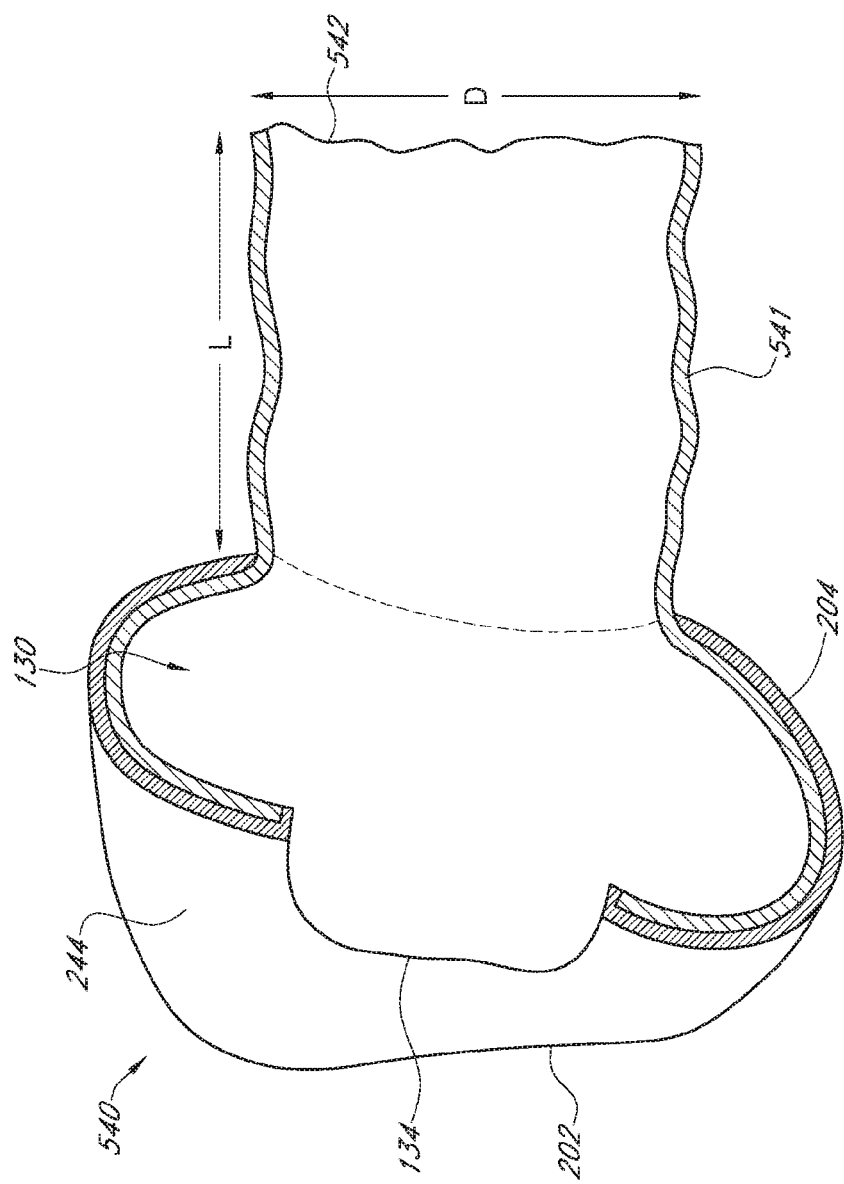
FIG. 18B is a cross-sectional view of the cushion of FIG. 18A with the textile cover in an uncovered state.

FIGS. 18A to 18D illustrate a configuration for a cushion 540 for use with the CPAP system 10 of FIG. 1. Description of certain similarities between the cushion 540 and cushions described previously may be omitted herein for the sake of brevity and convenience, but such omission is not limiting. Similar to the cushion 510, the cushion 540 comprises a face contacting portion 202 and a non-face contacting portion 204. The face contacting portion 202 may be attached to (e.g. via overmolding as previously described) or formed integral with the non-face contacting portion 204. A breathing chamber 130 is defined within the interior space defined by the face and non-face contacting portions 202, 204. In some configurations, the face contacting portion 202 comprises an oro-nasal opening 134 which receives the nose and/or mouth of the user, as illustrated in FIGS. 18A and 18B. Pressurized gases supplied by the conduit 120 enter the breathing chamber 130 and are received by the user through the oro-nasal opening 134. In other configurations, the face contacting portion 202 comprises a sheet of textile material having a breathable locating region 238 through which pressurized gases are supplied to the breathing chamber 130.

In contrast to the cushions described previously, the cushion 540 comprises a textile cover 541. The textile cover 541 may be tubular or cylindrical knit tube comprising a fixed end 543 that is secured to the cushion 540 and a free end 542. The textile cover 541 may be permanently secured to the non-face contacting portion 204, as illustrated in FIGS. 18A and 18B. In some configurations, the textile cover 541 may be removably secured to the non-face contacting portion, such that the textile cover 541 may be replaceable or interchangeable relative to the other portions of the cushion 540. In other configurations, the textile cover 541 may be disposed along the entirety or a substantial entirety of the breathing chamber 130 of the cushion 540, as illustrated in FIG. 18B. In some configurations, the textile cover 541 is disposed along at least 90% of the inner surface area of the breathing chamber 130 and/or all but a rim portion surrounding an opening (e.g., opening 134 or the inlet opening) of the cushion 540. The fixed end 543 of the textile cover 541 may be overmolded to the interior (e.g. breathing chamber-facing) side of the cushion 540 using an overmolding process similar to those described above. In further configurations, the textile cover 541 may comprise a stretchable material, such as the stretchable textile material 318 described previously.

Figure 18D:
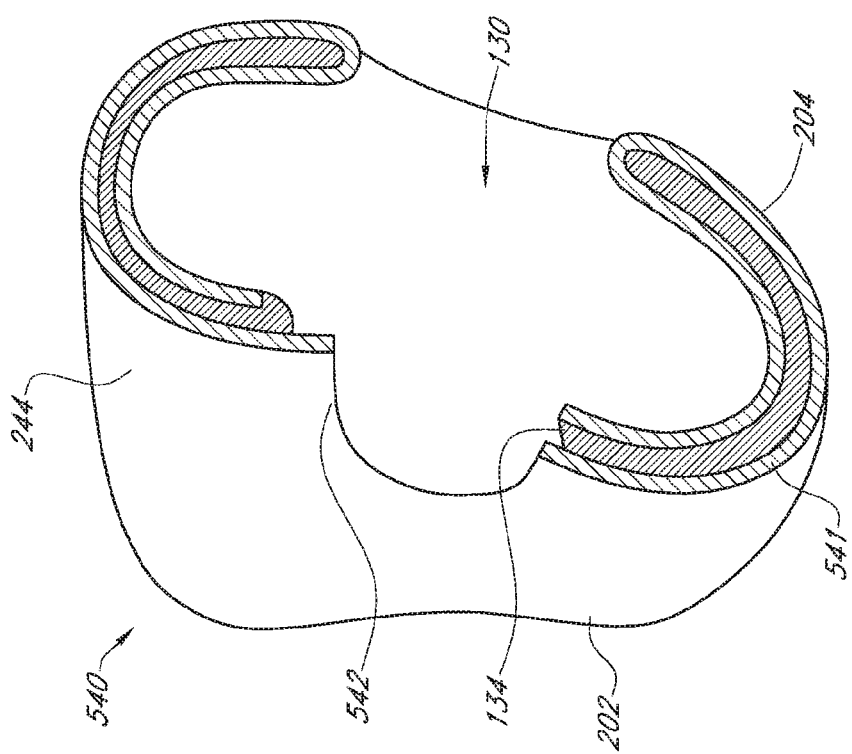
FIG. 18D is a cross-sectional view of the cushion of FIG. 18A with the textile cover in a covered state.

The textile cover 541 is selectively movable by the user between the uncovered state of FIGS. 18A and 18B and the covered state of FIGS. 18C and 18D. In the uncovered state, the free end 542 is removed from the face contacting portion 202 and moved toward or to the non-face contacting portion 204, thereby exposing the face contacting portion 202, the sealing region 244, and the non-face contacting portion 204, as shown in FIGS. 18A and 18B. Advantageously, in the uncovered state, the sealing region 244 can be easily cleaned independently from the textile cover 541. In some embodiments, the face and/or non-face contacting portions 202, 204 comprise a transparent elastomer such as silicone rubber 312 that allows the portions 202, 204 to retain the textile appearance of the fixed end 543 that covers the entirety of the breathing chamber 130 of the cushion 540.

As illustrated in FIG. 18B, the textile cover 541 has a length L and a diameter D. The diameter D is less than the height and/or width of the face contacting portion 202. Accordingly, in the covered state, the free end 542 of the textile cover 541 must be stretched to fit over the non-face contacting portion 204, the sealing region 244, and the face contacting portion 202. When stretched over the face contacting portion 202, the free end 542 of the stretchable textile cover 541 attempts to return to its diameter D, which retains the free end 542 in the covered state. The description of the diameter D assumes a substantially cylindrical shape having a circular cross-section. With other cross-sectional shapes, the free end 542 of the stretchable textile cover 541 preferably has a height and/or width that is smaller than corresponding dimensions of the face contacting portion 202. In the uncovered state, the length L of the textile cover 541 extends outwardly away from the breathing chamber 130 and non-face contacting portion 204, as illustrated in FIG. 18B. The length L may be equal to the distance necessary to allow the textile cover 541 to completely cover the sealing region 244 and either overhang or overlap an edge or perimeter of the oro-nasal opening 134 when in the covered state, to thereby provide a softer sealing surface. Accordingly, in the covered state, the textile cover 541 extends radially inward into the oro-nasal opening 134 to form a textile lip that rests on or is secured to the oro-nasal opening 134. In some configurations of the covered state, the free end 542 of the textile cover 541 is pulled over the sealing region 244 and secured to the face contacting portion 202, as illustrated in FIG. 18D. In the covered state of other configurations, the free end 542 is pulled over and secured around the oro-nasal opening 134, as illustrated in FIG. 18C. In further configurations, the fixed end 543 of the textile cover 541 is secured to the oro-nasal opening 134 and is stretched over and retained upon the non-face contacting portion 204 in the covered state. Regardless of the configuration, in the covered state, the cushion 540 provides the sealability of the sealing region 244 with the soft touch and appearance of the textile cover 541 that has an aesthetic more fitting for a bedroom environment.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavor in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

The invention claimed is:

1. A cushion for a respiratory mask, the cushion comprising:
    a face contacting portion comprising a locating region for locating a user's face relative to the mask and a sealing region for providing a seal against the user's face; and
    a non-face contacting portion,
    wherein the sealing region surrounds and is positioned radially outward of the locating region,
    wherein an outer perimeter of the locating region is attached to an inner perimeter of the sealing region; and
    wherein the locating region comprises a breathable textile material.

2. The cushion according to claim 1, wherein the sealing region comprises an elastomeric material.

3. The cushion according to claim 2, wherein the cushion comprises a transition region that extends between the sealing region and the locating region.

4. The cushion according to claim 3, wherein the transition region comprises a composite material.

5. The cushion according to claim 4, wherein the transition region has a greater thickness than the locating region.

6. The cushion according to claim 5, wherein the transition region protrudes in a thickness direction towards an interior of the cushion.

7. The cushion according to claim 5, wherein the transition region protrudes from an inner surface of the face contacting portion, and wherein an outer surface of the face contacting portion is a smooth continuous surface.

8. The cushion according to claim 3, wherein the transition region comprises a textile material that is impregnated with the elastomeric material of the sealing region.

9. The cushion according to claim 3, wherein, in use, the transition region and sealing region are configured to form a seal against the user's face.

10. The cushion according to claim 1, wherein the non-face contacting portion and the sealing region comprise the same material.

11. The cushion according to claim 1, wherein the non-face contacting material comprises a silicone material.

12. The cushion according to claim 1, wherein the locating region comprises a continuous surface that is breathable such that, in use, a supply of breathing gas can be provided to a user's airways through the locating region.

13. The cushion according to claim 1, wherein the locating region comprises a first opening configured, in use, to supply a breathing gas to at least a user's nose.

14. The cushion according to claim 13, wherein the first opening is a nasal opening configured to deliver a supply of breathing gas to a user's nose.

15. The cushion according to claim 14, wherein the locating region further comprises an oral opening located, in use, below the nasal opening.

16. The cushion according to claim 13, wherein the first opening is an oro-nasal opening configured to deliver a supply of breathing gas to a user's mouth and nose.

17. The cushion according to claim 1, wherein the textile material of the locating region comprises more than one layer.

* * * * *